United States Patent
De Haro Garcia et al.

(10) Patent No.: US 10,766,906 B2
(45) Date of Patent: Sep. 8, 2020

(54) FUSED HEXACYCLIC IMIDAZOLE DERIVATIVES AS MODULATORS OF TNF ACTIVITY

(71) Applicants: UCB Biopharma SRL, Brussels (BE); Sanofi, Paris (FR)

(72) Inventors: Teresa De Haro Garcia, Slough (GB); Michael Louis Robert Deligny, Brussels (BE); Jag Paul Heer, Slough (GB); Helen Tracey Horsley, Slough (GB); Sophie Jadot, Brussels (BE); Jean Keyaerts, Brussels (BE)

(73) Assignee: UCB Biopharma SRL, Brussels (BE)

( * ) Notice: Subject to any disclaimer, the term of this patent is extended or adjusted under 35 U.S.C. 154(b) by 0 days.

(21) Appl. No.: 16/086,414

(22) PCT Filed: Mar. 31, 2017

(86) PCT No.: PCT/EP2017/057768
§ 371 (c)(1),
(2) Date: Sep. 19, 2018

(87) PCT Pub. No.: WO2017/167995
PCT Pub. Date: Oct. 5, 2017

(65) Prior Publication Data
US 2019/0100526 A1    Apr. 4, 2019

(30) Foreign Application Priority Data
Apr. 1, 2016 (EP) .................................. 16163577

(51) Int. Cl.
*C07D 487/22* (2006.01)
*C07D 487/18* (2006.01)
*C07D 487/04* (2006.01)

(52) U.S. Cl.
CPC ......... *C07D 487/22* (2013.01); *C07D 487/04* (2013.01); *C07D 487/18* (2013.01)

(58) Field of Classification Search
CPC ................................................. C07D 487/22
See application file for complete search history.

(56) References Cited

U.S. PATENT DOCUMENTS

| | | | |
|---|---|---|---|
| 2015/0152065 A1 | 6/2015 | Brookings et al. | |
| 2020/0046723 A1* | 2/2020 | Brookings | A61P 25/00 |

FOREIGN PATENT DOCUMENTS

| | | |
|---|---|---|
| WO | WO 2004/087720 | 10/2004 |
| WO | WO 2009/156091 | 12/2009 |
| WO | WO 2012/135082 | 10/2012 |
| WO | WO 2012/177707 | 12/2012 |
| WO | WO 2013/186229 | 12/2013 |
| WO | WO 2014/009295 | 1/2014 |
| WO | WO 2014/009296 | 1/2014 |
| WO | WO 2015/086525 | 6/2015 |
| WO | WO 2015/086526 | 6/2015 |
| WO | WO 2016/050975 | 4/2016 |

OTHER PUBLICATIONS

Tansey & Szymkowski, Drug Discovery Today, 2009, 14, 1082-1088.
Carneiro et al., J. Secual Medicine, 2010, 7, 3823-3834.
Wu et al., JAMA, 2013, 309, 2043-2044.
Hauwemeiren et al., J. Clin, Invest., 2013, 123, 2590-2603.
Hilpert et al., Journal of medicinal Chemistry, 2013, 56(10), 3980-3995.
Armstrong et al., J. Org. Chem., 2013, 78, 10534.
Nagib & McMillan, Nature, 2011, 480, 224.
Bentley et al., Organic Process Research & Development, 2002, 6(2) 109-112.
Nam et al., Bio-org. Med. Chem., 2004, 12, 6255.
Lacko et al., Current Medicinal Chemistry, 2012, 19, 4699.

* cited by examiner

*Primary Examiner* — Emily A Bernhardt
(74) *Attorney, Agent, or Firm* — McDonnell Boehnen Hulbert & Berghoff LLP

(57) ABSTRACT

Disclosed are substituted fused hexacyclic benzimidazole derivatives of Formula (I)

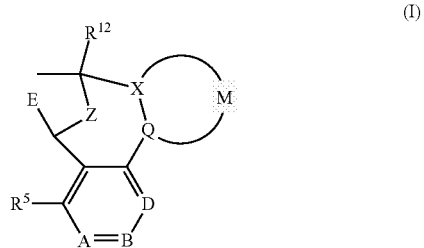

wherein the variables A, B, D, X, M, Q, n, p, q, Z, E, $R^5$, and $R^{12}$ are defined herein. These compounds are potent modulators of human TNFα activity and of benefit in the treatment and/or prevention of various human ailments, including autoimmune and inflammatory disorders; neurological and neurodegenerative disorders; pain and nociceptive disorders; cardiovascular disorders; metabolic disorders; ocular disorders; and oncological disorders.

5 Claims, No Drawings

FUSED HEXACYCLIC IMIDAZOLE DERIVATIVES AS MODULATORS OF TNF ACTIVITY

This application is a US national stage application under 35 U.S.C. § 371 of International Application No. PCT/EP2017/057768, filed Mar. 31, 2017, which claims priority to European Application No. 16163577.6, filed Apr. 1, 2016.

The present invention relates to a class of fused hexacyclic imidazole derivatives, and to their use in therapy. More particularly, this invention is concerned with pharmacologically active substituted fused hexacyclic benzimidazole derivatives and analogues thereof. These compounds are modulators of the signalling of TNFα, and are accordingly of benefit as pharmaceutical agents, especially in the treatment of adverse inflammatory and autoimmune disorders, neurological and neurodegenerative disorders, pain and nociceptive disorders, cardiovascular disorders, metabolic disorders, ocular disorders, and oncological disorders.

TNFα is the prototypical member of the Tumour Necrosis Factor (TNF) superfamily of proteins that share a primary function of regulating cell survival and cell death. One structural feature common to all known members of the TNF superfamily is the formation of trimeric complexes that bind to, and activate, specific TNF superfamily receptors. By way of example, TNFα exists in soluble and transmembrane forms and signals through two receptors, known as TNFR1 and TNFR2, with distinct functional endpoints.

Various products capable of modulating TNFα activity are already commercially available. All are approved for the treatment of inflammatory and autoimmune disorders such as rheumatoid arthritis and Crohn's disease. All currently approved products are macromolecular and act by inhibiting the binding of human TNFα to its receptor. Typical macromolecular TNFα inhibitors include anti-TNFα antibodies; and soluble TNFα receptor fusion proteins. Examples of commercially available anti-TNFα antibodies include fully human antibodies such as adalimumab (Humira®) and golimumab (Simponi®), chimeric antibodies such as infliximab (Remicade®), and pegylated Fab' fragments such as certolizumab pegol (Cimzia®). An example of a commercially available soluble TNFα receptor fusion protein is etanercept (Enbrel®).

TNF superfamily members, including TNFα itself, are implicated in a variety of physiological and pathological functions that are believed to play a part in a range of conditions of significant medical importance (see, for example, M. G. Tansey & D. E. Szymkowski, *Drug Discovery Today*, 2009, 14, 1082-1088; and F. S. Carneiro et al., *J. Sexual Medicine*, 2010, 7, 3823-3834).

The compounds in accordance with the present invention, being potent modulators of human TNFα activity, are therefore beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

In addition, the compounds in accordance with the present invention may be beneficial as pharmacological standards for use in the development of new biological tests and in the search for new pharmacological agents. Thus, in one embodiment, the compounds of this invention may be useful as radioligands in assays for detecting pharmacologically active compounds. In an alternative embodiment, certain compounds of this invention may be useful for coupling to a fluorophore to provide fluorescent conjugates that can be utilised in assays (e.g. a fluorescence polarisation assay) for detecting pharmacologically active compounds.

WO 2013/186229, WO 2014/009295 and WO 2014/009296 relate to fused bicyclic imidazole derivatives which are modulators of the signalling of TNFα.

WO 2015/086525 and WO 2015/086526 relate to fused tricyclic imidazole derivatives which are modulators of the signalling of TNFα.

Co-pending international patent application PCT/EP2015/072868 (published on 7 Apr. 2016 as WO 2016/050975) relates to fused pentacyclic imidazole derivatives which are modulators of the signalling of TNFα.

None of the prior art available to date, however, discloses or suggests the precise structural class of fused hexacyclic imidazole derivatives as provided by the present invention.

The present invention provides a compound of formula (I) or an N-oxide thereof, or a pharmaceutically acceptable salt thereof:

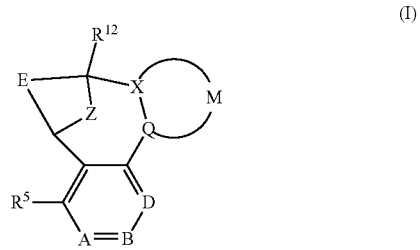

wherein
A represents N or C—R$^6$;
B represents N or C—R$^7$;
D represents N or C—R$^8$;
—(X-M-Q)- represents an optionally substituted five-membered heteroaromatic ring selected from furyl, thienyl, pyrrolyl, pyrazolyl, oxazolyl, isoxazolyl, thiazolyl, isothiazolyl, imidazolyl, oxadiazolyl, thiadiazolyl, triazolyl and tetrazolyl; or
—(X-M-Q)- represents a saturated or partially saturated five- or six-membered heterocyclic ring containing n carbon atoms, p oxygen atoms and q nitrogen atoms, which ring may be optionally substituted by one or more substituents;
n is 2, 3, 4 or 5;
p is zero or 1; and
q is 1, 2 or 3, such that (n+p+q) is 5 or 6;
Z represents methylene;
E represents a fused heteroaromatic ring system selected from the groups of formula (Ea), (Eb) and (Ec):

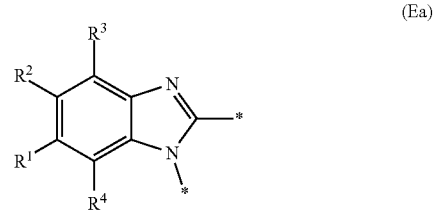

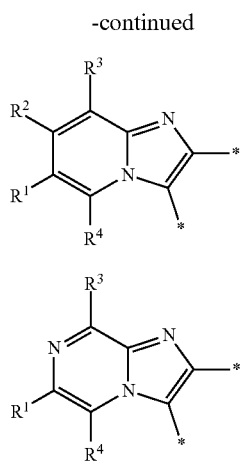

(Eb)

(Ec)

wherein the asterisks (*) represent the site of attachment of E to the remainder of the molecule;

$R^1$ represents hydrogen, halogen, cyano, trifluoromethyl, trifluoromethoxy, —$OR^a$, —$SR^a$, —$SOR^a$, —$SO_2R^a$, —$NR^bR^c$, —$NR^cCOR^d$, —$NR^cCO_2R^d$, —$NHCONR^bR^c$, —$NR^cSO_2R^e$, —$COR^d$, —$CO_2R^d$, —$CONR^bR^c$, —$SO_2NR^bR^c$, or —$S(O)(N-R^b)R^e$; or $R^1$ represents $C_{1-6}$ alkyl, $C_{3-7}$ cycloalkyl, $C_{4-7}$ cycloalkenyl, aryl, aryl($C_{1-6}$)alkyl, $C_{3-7}$ heterocycloalkyl, $C_{3-7}$ heterocycloalkenyl, heteroaryl, heteroaryl($C_{1-6}$)alkyl, ($C_{3-7}$)heterocycloalkyl($C_{1-6}$)alkyl-aryl-, ($C_{3-7}$)heterocycloalkenyl-aryl-, ($C_{3-7}$)cycloalkyl-heteroaryl-, ($C_{3-7}$)cycloalkyl-($C_{1-6}$)alkyl-heteroaryl-, ($C_{4-7}$)cycloalkenyl-heteroaryl-, ($C_{4-9}$)bicycloalkyl-heteroaryl-, ($C_{3-7}$)heterocycloalkyl-heteroaryl-, ($C_{3-7}$)heterocycloalkyl($C_{1-6}$)alkyl-heteroaryl-, ($C_{3-7}$)heterocycloalkenyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents;

$R^2$ represents hydrogen, halogen, cyano, nitro, hydroxy, trifluoromethyl, trifluoromethoxy or —$OR^a$; or $R^2$ represents $C_{1-6}$ alkyl or heteroaryl, either of which groups may be optionally substituted by one or more substituents;

$R^3$ and $R^4$ independently represent hydrogen, halogen or trifluoromethyl; or $C_{1-6}$ alkyl, which group may be optionally substituted by one or more substituents;

$R^5$ represents hydrogen, halogen, hydroxy, cyano, trifluoromethyl, difluoromethoxy, trifluoromethoxy, —$OR^a$ or $C_{1-6}$ alkylsulphonyl; or $R^5$ represents $C_{1-6}$ alkyl, which group may be optionally substituted by one or more substituents;

$R^6$, $R^7$ and $R^8$ independently represent hydrogen, halogen, trifluoromethyl, $C_{1-6}$ alkyl or $C_{1-6}$ alkoxy;

$R^{12}$ represents hydrogen or $C_{1-6}$ alkyl;

$R^a$ represents $C_{1-6}$ alkyl, $C_{3-7}$ cycloalkyl, aryl, aryl($C_{1-6}$)alkyl, $C_{3-7}$ heterocycloalkyl, heteroaryl or heteroaryl($C_{1-6}$)alkyl, any of which groups may be optionally substituted by one or more substituents;

$R^b$ and $R^c$ independently represent hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents; or $R^b$ and $R^c$, when taken together with the nitrogen atom to which they are both attached, represent a heterocyclic moiety selected from azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl, homopiperazin-1-yl, (imino)(oxo)thiazinan-4-yl, (oxo)thiazinan-4-yl and (dioxo)thiazinan-4-yl, any of which groups may be optionally substituted by one or more substituents;

$R^d$ represents hydrogen; or $R^d$ represents $C_{1-6}$ alkyl, $C_{3-7}$ cycloalkyl, aryl, $C_{3-7}$ heterocycloalkyl or heteroaryl, any of which groups may be optionally substituted by one or more substituents; and $R^e$ represents $C_{1-6}$ alkyl, aryl or heteroaryl, any of which groups may be optionally substituted by one or more substituents.

The present invention also provides a compound of formula (I) as defined above or an N-oxide thereof, or a pharmaceutically acceptable salt thereof, for use in therapy.

The present invention also provides a compound of formula (I) as defined above or an N-oxide thereof, or a pharmaceutically acceptable salt thereof, for use in the treatment and/or prevention of disorders for which the administration of a modulator of TNFα function is indicated.

In another aspect, the present invention provides a compound of formula (I) as defined above or an N-oxide thereof, or a pharmaceutically acceptable salt thereof, for use in the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder.

The present invention also provides the use of a compound of formula (I) as defined above or an N-oxide thereof, or a pharmaceutically acceptable salt thereof, for the manufacture of a medicament for the treatment and/or prevention of disorders for which the administration of a modulator of TNFα function is indicated.

In another aspect, the present invention provides the use of a compound of formula (I) as defined above or an N-oxide thereof, or a pharmaceutically acceptable salt thereof, for the manufacture of a medicament for the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder.

The present invention also provides a method for the treatment and/or prevention of disorders for which the administration of a modulator of TNFα function is indicated which comprises administering to a patient in need of such treatment an effective amount of a compound of formula (I) as defined above or an N-oxide thereof, or a pharmaceutically acceptable salt thereof.

In another aspect, the present invention provides a method for the treatment and/or prevention of an inflammatory or autoimmune disorder, a neurological or neurodegenerative disorder, pain or a nociceptive disorder, a cardiovascular disorder, a metabolic disorder, an ocular disorder, or an oncological disorder, which comprises administering to a patient in need of such treatment an effective amount of a compound of formula (I) as defined above or an N-oxide thereof, or a pharmaceutically acceptable salt thereof.

Where any of the groups in the compounds of formula (I) above is stated to be optionally substituted, this group may be unsubstituted, or substituted by one or more substituents. Typically, such groups will be unsubstituted, or substituted by one or two substituents.

The present invention includes within its scope salts of the compounds of formula (I) above. For use in medicine, the salts of the compounds of formula (I) will be pharmaceutically acceptable salts. Other salts may, however, be useful in the preparation of the compounds of use in the invention or of their pharmaceutically acceptable salts.

Standard principles underlying the selection and preparation of pharmaceutically acceptable salts are described, for example, in *Handbook of Pharmaceutical Salts: Properties, Selection and Use*, ed. P. H. Stahl & C. G. Wermuth, Wiley-VCH, 2002.

The present invention includes within its scope solvates of the compounds of formula (I) above. Such solvates may be formed with common organic solvents or water.

The present invention also includes within its scope co-crystals of the compounds of formula (I) above. The technical term "co-crystal" is used to describe the situation where neutral molecular components are present within a crystalline compound in a definite stoichiometric ratio. The preparation of pharmaceutical co-crystals enables modifications to be made to the crystalline form of an active pharmaceutical ingredient, which in turn can alter its physicochemical properties without compromising its intended biological activity (see *Pharmaceutical Salts and Co-crystals*, ed. J. Wouters & L. Quere, RSC Publishing, 2012).

Suitable alkyl groups which may be present on the compounds in accordance with the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Suitable alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

The term "$C_{3-7}$ cycloalkyl" as used herein refers to monovalent groups of 3 to 7 carbon atoms derived from a saturated monocyclic hydrocarbon, and may comprise benzo-fused analogues thereof. Suitable $C_{3-7}$ cycloalkyl groups include cyclopropyl, cyclobutyl, benzocyclobutenyl, cyclopentyl, indanyl, cyclohexyl and cycloheptyl.

The term "$C_{4-7}$ cycloalkenyl" as used herein refers to monovalent groups of 4 to 7 carbon atoms derived from a partially unsaturated monocyclic hydrocarbon. Suitable $C_{4-7}$ cycloalkenyl groups include cyclobutenyl, cyclopentenyl, cyclohexenyl and cycloheptenyl.

The term "$C_{4-9}$ bicycloalkyl" as used herein refers to monovalent groups of 4 to 9 carbon atoms derived from a saturated bicyclic hydrocarbon. Typical bicycloalkyl groups include bicyclo[3.1.0]hexanyl, bicyclo[4.1.0]heptanyl and bicyclo[2.2.2]octanyl.

The term "aryl" as used herein refers to monovalent carbocyclic aromatic groups derived from a single aromatic ring or multiple condensed aromatic rings. Suitable aryl groups include phenyl and naphthyl, preferably phenyl.

Suitable aryl($C_{1-6}$)alkyl groups include benzyl, phenylethyl, phenylpropyl and naphthylmethyl.

The term "$C_{3-7}$ heterocycloalkyl" as used herein refers to saturated monocyclic rings containing 3 to 7 carbon atoms and at least one heteroatom selected from oxygen, sulphur and nitrogen, and may comprise benzo-fused analogues thereof. Suitable heterocycloalkyl groups include oxetanyl, azetidinyl, tetrahydrofuranyl, dihydrobenzo-furanyl, dihydrobenzothienyl, pyrrolidinyl, indolinyl, isoindolinyl, oxazolidinyl, thiazolidinyl, isothiazolidinyl, imidazolidinyl, tetrahydropyranyl, chromanyl, dioxanyl, tetrahydrothiopyranyl, piperidinyl, 1,2,3,4-tetrahydroquinolinyl, 1,2,3,4-tetrahydro-isoquinolinyl, piperazinyl, 1,2,3,4-tetrahydroquinoxalinyl, hexahydro-[1,2,5]thiadiazolo-[2,3-a]pyrazinyl, homopiperazinyl, morpholinyl, benzoxazinyl, thiomorpholinyl, azepanyl, oxazepanyl, diazepanyl, thiadiazepanyl and azocanyl.

The term "$C_{3-7}$ heterocycloalkenyl" as used herein refers to monounsaturated or polyunsaturated monocyclic rings containing 3 to 7 carbon atoms and at least one heteroatom selected from oxygen, sulphur and nitrogen, and may comprise benzo-fused analogues thereof. Suitable heterocycloalkenyl groups include thiazolinyl, imidazolinyl, dihydropyranyl, dihydrothiopyranyl and 1,2,3,6-tetrahydropyridinyl.

The term "$C_{4-9}$ heterobicycloalkyl" as used herein corresponds to $C_{4-9}$ bicycloalkyl wherein one or more of the carbon atoms have been replaced by one or more heteroatoms selected from oxygen, sulphur and nitrogen. Typical heterobicycloalkyl groups include 3-azabicyclo[3.1.0]hexanyl, 2-oxa-5-azabicyclo[2.2.1]heptanyl, 6-azabicyclo[3.2.0]heptanyl, 3-azabicyclo[3.1.1]heptanyl, 3-azabicyclo[4.1.0]heptanyl, 2-oxabicyclo[2.2.2]octanyl, quinuclidinyl, 2-oxa-5-azabicyclo[2.2.2]octanyl, 3-azabicyclo[3.2.1]octanyl, 8-azabicyclo-[3.2.1]octanyl, 3-oxa-8-azabicyclo[3.2.1]octanyl, 3,8-diazabicyclo[3.2.1]octanyl, 3,6-diazabicyclo[3.2.2]nonanyl, 3-oxa-7-azabicyclo[3.3.1]nonanyl, 3,7-dioxa-9-azabicyclo-[3.3.1]nonanyl and 3,9-diazabicyclo[4.2.1]nonanyl.

The term "$C_{4-9}$ spiroheterocycloalkyl" as used herein refers to saturated bicyclic ring systems containing 4 to 9 carbon atoms and at least one heteroatom selected from oxygen, sulphur and nitrogen, in which the two rings are linked by a common atom.

Suitable spiroheterocycloalkyl groups include 5-azaspiro[2.3]hexanyl, 5-azaspiro[2.4]-heptanyl, 2-azaspiro[3.3]heptanyl, 2-oxa-6-azaspiro[3.3]heptanyl, 2-oxa-6-azaspiro[3.4]-octanyl, 2-oxa-6-azaspiro[3.5]nonanyl, 7-oxa-2-azaspiro[3.5]nonanyl, 2-oxa-7-azaspiro-[3.5]nonanyl and 2,4,8-triazaspiro[4.5]decanyl.

The term "heteroaryl" as used herein refers to monovalent aromatic groups containing at least 5 atoms derived from a single ring or multiple condensed rings, wherein one or more carbon atoms have been replaced by one or more heteroatoms selected from oxygen, sulphur and nitrogen. Suitable heteroaryl groups include furyl, benzofuryl, dibenzo furyl, thienyl, benzothienyl, thieno[2,3-c]pyrazolyl, thieno[3,4-b][1,4]dioxinyl, dibenzothienyl, pyrrolyl, indolyl, pyrrolo[2,3-b]pyridinyl, pyrrolo[3,2-c]pyridinyl, pyrrolo[3,4-b]pyridinyl, pyrazolyl, pyrazolo[1,5-a]pyridinyl, pyrazolo[3,4-d]pyrimidinyl, indazolyl, 4,5,6,7-tetrahydroindazolyl, oxazolyl, benzoxazolyl, isoxazolyl, thiazolyl, benzothiazolyl, isothiazolyl, imidazolyl, benzimidazolyl, imidazo[2,1-b]thiazolyl, imidazo[1,2-a]pyridinyl, imidazo[4,5-b]pyridinyl, purinyl, imidazo[1,2-a]pyrimidinyl, imidazo[1,2-a]pyrazinyl, oxadiazolyl, thiadiazolyl, triazolyl, [1,2,4]triazolo[1,5-a]-pyrimidinyl, benzotriazolyl, tetrazolyl, pyridinyl, quinolinyl, isoquinolinyl, naphthyridinyl, pyridazinyl, cinnolinyl, phthalazinyl, pyrimidinyl, quinazolinyl, pyrazinyl, quinoxalinyl, pteridinyl, triazinyl and chromenyl groups.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds in accordance with the invention possess two or more asymmetric centres, they may additionally exist as diastereomers. The invention is to be understood to extend to the use of all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto (CH$_2$C=O)↔enol (CH=CHOH) tautomers or amide (NHC=O)↔hydroxyimine (N=COH) tautomers. Formula (I) and the formulae depicted hereinafter are intended to represent all individual tautomers and all possible mixtures thereof, unless stated or shown otherwise.

As will be appreciated, 2-oxo-(1H)-pyridinyl is a tautomer of 2-hydroxypyridinyl; and 2-oxo-(1H)-pyrimidinyl is a tautomer of 2-hydroxypyrimidinyl.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1$H, $^2$H (deuterium) or $^3$H (tritium) atom, preferably $^1$H. Similarly, by way of example, each individual carbon atom present in formula (I), or in the formulae depicted hereinafter, may be present as a $^{12}$C, $^{13}$C or $^{14}$C atom, preferably $^{12}$C.

A particular sub-class of compounds in accordance with the present invention is represented by formula (IA) or an N-oxide thereof, or a pharmaceutically acceptable salt thereof:

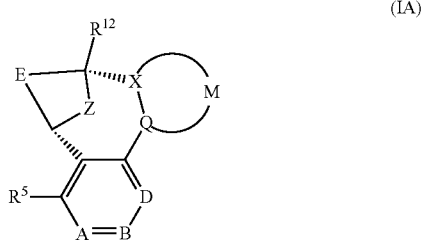

(IA)

wherein A, B, D, —(X-M-Q)-, Z, E, R$^5$ and R$^{12}$ are as defined above.

In a first embodiment, A represents N. In a second embodiment, A represents C—R$^6$.

In a first embodiment, B represents N. In a second embodiment, B represents C—R$^7$.

In a first embodiment, D represents N. In a second embodiment, D represents C—R$^8$.

In a first embodiment, A, B and D all represent N. In a second embodiment, A and B both represent N, and D represents C—R$^8$. In a third embodiment, A and D both represent N, and B represents C—R$^7$. In a fourth embodiment, A represents N, B represents C—R$^7$, and D represents C—R$^8$. In a fifth embodiment, A represents C—R$^6$, and B and D both represent N. In a sixth embodiment, A represents C—R$^6$, B represents N, and D represents C—R$^8$. In a seventh embodiment, A represents C—R$^6$, B represents C—R$^7$, and D represents N. In an eighth embodiment, A represents C—R$^6$, B represents C—R$^7$, and D represents C—R$^8$.

Suitably, at least one of A, B and D is other than N.

Where the moiety —(X-M-Q)- in the compounds of the invention represents an optionally substituted five-membered heteroaromatic ring, this ring is typically selected from pyrrolyl, pyrazolyl, imidazolyl, triazolyl and tetrazolyl.

Where the moiety —(X-M-Q)- in the compounds of the invention represents an optionally substituted five-membered heteroaromatic ring, this ring is suitably selected from imidazolyl, [1,2,3]triazolyl and [1,2,4]triazolyl.

In a first embodiment, —(X-M-Q)- represents optionally substituted furyl. In a second embodiment, —(X-M-Q)- represents optionally substituted thienyl. In a third embodiment, —(X-M-Q)- represents optionally substituted pyrrolyl. In a fourth embodiment, —(X-M-Q)- represents optionally substituted pyrazolyl. In a fifth embodiment, —(X-M-Q)- represents optionally substituted oxazolyl. In a sixth embodiment, —(X-M-Q)- represents optionally substituted isoxazolyl. In a seventh embodiment, —(X-M-Q)- represents optionally substituted thiazolyl. In an eighth embodiment, —(X-M-Q)- represents optionally substituted isothiazolyl. In a ninth embodiment, —(X-M-Q)- represents optionally substituted imidazolyl. In a tenth embodiment, —(X-M-Q)- represents [1,2,5]oxadiazolyl. In an eleventh embodiment, —(X-M-Q)- represents [1,2,5]thiadiazolyl. In a twelfth embodiment, —(X-M-Q)- represents optionally substituted [1,2,3]triazolyl. In a thirteenth embodiment, —(X-M-Q)- represents optionally substituted [1,2,4]triazolyl. In a fourteenth embodiment, —(X-M-Q)- represents tetrazolyl.

Alternatively, the moiety —(X-M-Q)- may represent a saturated or partially saturated five- or six-membered heterocyclic ring containing n carbon atoms, p oxygen atoms and q nitrogen atoms, which ring may be optionally substituted by one or more substituents.

In a first embodiment, —(X-M-Q)- represents a saturated five-membered heterocyclic ring containing n carbon atoms, p oxygen atoms and q nitrogen atoms, which ring may be optionally substituted by one or more substituents. In a second embodiment, —(X-M-Q)- represents a saturated six-membered heterocyclic ring containing n carbon atoms, p oxygen atoms and q nitrogen atoms, which ring may be optionally substituted by one or more substituents. In a third embodiment, —(X-M-Q)- represents a partially saturated five-membered heterocyclic ring containing n carbon atoms, p oxygen atoms and q nitrogen atoms, which ring may be optionally substituted by one or more substituents. In a fourth embodiment, —(X-M-Q)- represents a partially saturated six-membered heterocyclic ring containing n carbon atoms, p oxygen atoms and q nitrogen atoms, which ring may be optionally substituted by one or more substituents.

In a first embodiment, n is 2. In a second embodiment, n is 3. In a third embodiment, n is 4. In a fourth embodiment, n is 5.

In a first embodiment, p is zero. In a second embodiment, p is 1.

In a first embodiment, q is 1. In a second embodiment, q is 2. In a third embodiment, q is 3.

In a first embodiment, n is 2, p is zero, and q is 3. In a second embodiment, n is 3, p is zero, and q is 2. In a third embodiment, n is 3, p is zero, and q is 3. In a fourth embodiment, n is 4, p is zero, and q is 1. In a fifth embodiment, n is 4, p is zero, and q is 2. In a sixth embodiment, n is 5, p is zero, and q is 1. In a seventh embodiment, n is 2, p is 1, and q is 2. In an eighth embodiment, n is 2, p is 1, and q is 3. In a ninth embodiment, n is 3, p is 1, and q is 1. In a tenth embodiment, n is 3, p is 1, and q is 2. In an eleventh embodiment, n is 4, p is 1, and q is 1.

The moiety —(X-M-Q)- may be unsubstituted, or may be substituted, where possible, by one or more substituents, generally by one, two or three substituents, typically by one or two substituents. In one embodiment, this ring is unsubstituted. In another embodiment, this ring is monosubstituted. In a further embodiment, this ring is disubstituted. In a still further embodiment, this ring is trisubstituted.

Typical examples of optional substituents on the moiety —(X-M-Q)- include halogen, cyano, $C_{1-6}$ alkyl, fluoromethyl, difluoromethyl, trifluoromethyl, hydroxy, hydroxy($C_{1-6}$)alkyl, $C_{1-6}$ alkoxy, difluoromethoxy, trifluoromethoxy, oxo, pentafluorothio, $C_{1-6}$ alkylthio, $C_{1-6}$ alkylsulphinyl, $C_{1-6}$ alkylsulphonyl, amino, amino($C_{1-6}$)alkyl, $C_{1-6}$ alkylamino, di($C_{1-6}$)alkylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulphonyl, $C_{1-6}$ alkylaminosulphonyl, di($C_{1-6}$)alkylaminosulphonyl, ($C_{1-6}$)alkylsulphoximinyl and [($C_{1-6}$)alkyl][N—($C_{1-6}$)alkyl]sulphoximinyl.

Illustrative examples of optional substituents on the moiety —(X-M-Q)- include $C_{1-6}$ alkyl, trifluoromethyl, hydroxy and oxo.

Suitable examples of optional substituents on the moiety —(X-M-Q)- include $C_{1-6}$ alkyl, trifluoromethyl and hydroxy.

Typical examples of particular substituents on the moiety —(X-M-Q)- include fluoro, chloro, bromo, cyano, methyl, fluoromethyl, difluoromethyl, trifluoromethyl, hydroxy, hydroxymethyl, hydroxyethyl, hydroxyisopropyl, methoxy, difluoromethoxy, trifluoromethoxy, oxo, pentafluorothio, methylthio, methylsulphinyl, methylsulphonyl, amino, aminomethyl, methylamino, dimethylamino, formyl, acetyl, carboxy, methoxycarbonyl, ethoxycarbonyl, tert-butoxycarbonyl, aminocarbonyl, methylaminocarbonyl, dimethylaminocarbonyl, aminosulphonyl, methylaminosulphonyl, dimethylaminosulphonyl, methylsulphoximinyl and (methyl)(N-methyl)sulphoximinyl.

Illustrative examples of optional substituents on the moiety —(X-M-Q)- include methyl, trifluoromethyl, hydroxy and oxo.

Suitable examples of optional substituents on the moiety —(X-M-Q)- include methyl, trifluoromethyl and hydroxy.

Illustrative values for the moiety —(X-M-Q)- include the groups of formula (Ma), (Mb), (Mc), (Md), (Me), (Mf), (Mg), (Mh), (Mi), (Mj), (Mk), (Ml), (Mm), (Mn), (Mo) and (Mp):

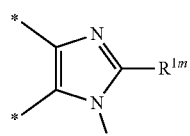

(Ma)

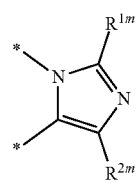

(Mb)

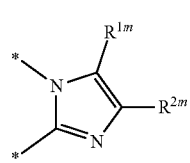

(Mc)

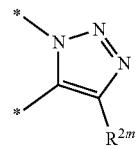

(Md)

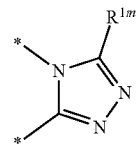

(Me)

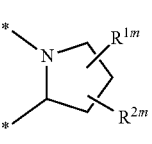

(Mf)

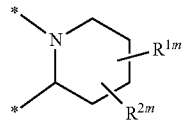

(Mg)

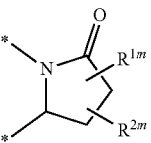

(Mh)

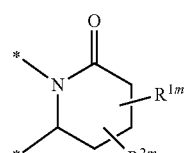

(Mi)

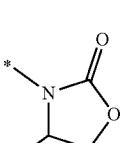

(Mj)

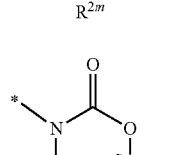

(Mk)

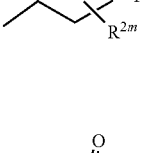

(Ml)

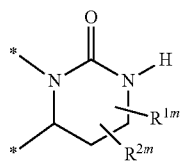
(Mm)

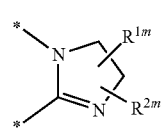
(Mn)

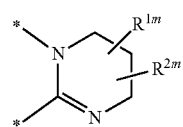
(Mo)

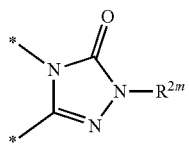
(Mp)

wherein the asterisks (*) represent the site of attachment to the remainder of the molecule;

$R^{1m}$ represents hydrogen, halogen, cyano, $C_{1-6}$ alkyl, fluoromethyl, difluoromethyl, trifluoromethyl, hydroxy, hydroxy($C_{1-6}$)alkyl, $C_{1-6}$ alkoxy, difluoromethoxy, trifluoromethoxy, pentafluorothio, $C_{1-6}$ alkylthio, $C_{1-6}$ alkylsulphinyl, $C_{1-6}$ alkylsulphonyl, amino, amino($C_{1-6}$)alkyl, $C_{1-6}$ alkylamino, di($C_{1-6}$)alkylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulphonyl, $C_{1-6}$ alkylaminosulphonyl, di($C_{1-6}$)alkylaminosulphonyl, ($C_{1-6}$)alkylsulphoximinyl or [($C_{1-6}$)alkyl][N—($C_{1-6}$)alkyl] sulphoximinyl; and $R^{2m}$ represents hydrogen or $C_{1-6}$ alkyl.

Typically, $R^{1m}$ represents hydrogen, $C_{1-6}$ alkyl, trifluoromethyl or hydroxy.

Typical values of $R^{1m}$ include hydrogen, fluoro, chloro, bromo, cyano, methyl, fluoromethyl, difluoromethyl, trifluoromethyl, hydroxy, hydroxymethyl, hydroxyethyl, hydroxyisopropyl, methoxy, difluoromethoxy, trifluoromethoxy, pentafluorothio, methylthio, methylsulphinyl, methylsulphonyl, amino, aminomethyl, methylamino, dimethylamino, formyl, acetyl, carboxy, methoxycarbonyl, ethoxycarbonyl, tert-butoxycarbonyl, aminocarbonyl, methylaminocarbonyl, dimethylaminocarbonyl, aminosulphonyl, methylaminosulphonyl, dimethylaminosulphonyl, methylsulphoximinyl and (methyl)(N-methyl)sulphoximinyl.

Suitable values of $R^{1m}$ include hydrogen, methyl, trifluoromethyl and hydroxy.

Suitably, $R^{2m}$ represents hydrogen or methyl.

In a first embodiment, $R^{2m}$ represents hydrogen. In a second embodiment, $R^{2m}$ represents $C_{1-6}$ alkyl, especially methyl.

Particular values for the moiety —(X-M-Q)- include the groups of formula (Ma), (Mb), (Mc), (Md) and (Me) as defined above.

Generally, E represents a fused heteroaromatic ring system of formula (Ea) or (Eb).

In a first embodiment, E represents a fused heteroaromatic ring system of formula (Ea).

In a second embodiment, E represents a fused heteroaromatic ring system of formula (Eb).

In a third embodiment, E represents a fused heteroaromatic ring system of formula (Ec).

Particular sub-classes of compounds in accordance with the present invention include the compounds of formula (IB), (IC) and (ID) and N-oxides thereof, and pharmaceutically acceptable salts thereof:

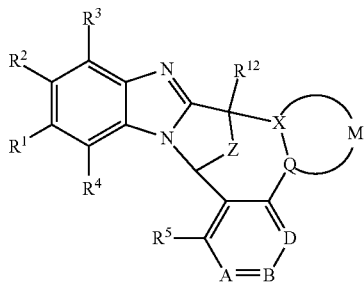
(IB)

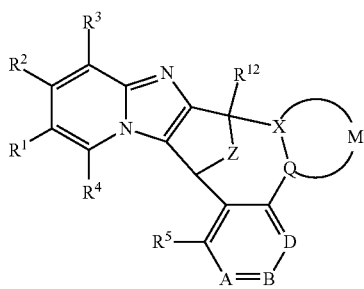
(IC)

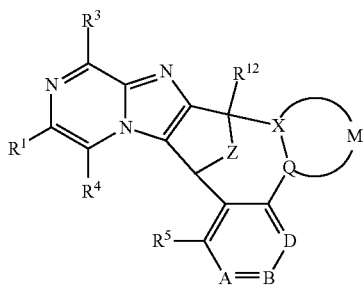
(ID)

wherein A, B, D, —(X-M-Q)-, Z, $R^1$, $R^2$, $R^3$, $R^4$, $R^5$ and $R^{12}$ are as defined above.

Particular sub-classes of compounds in accordance with the present invention include the compounds of formula (IB) and (IC) as defined above.

A particular sub-class of compounds in accordance with the present invention is represented by formula (IB) as defined above.

Generally, $R^1$ represents hydrogen, halogen or cyano; or $R^1$ represents aryl, $C_{3-7}$ heterocycloalkyl, $C_{3-7}$ heterocycloalkenyl, heteroaryl, heteroaryl-aryl-, ($C_{3-7}$)cycloalkyl-heteroaryl-, ($C_{4-9}$)bicycloalkyl-heteroaryl-, ($C_{3-7}$)heterocycloalkyl-heteroaryl-, ($C_{4-9}$)heterobicycloalkyl-heteroaryl- or ($C_{4-9}$)spiroheterocycloalkyl-heteroaryl-, any of which groups may be optionally substituted by one or more substituents.

Typically, $R^1$ represents halogen; or $R^1$ represents $C_{3-7}$ heterocycloalkyl, heteroaryl, ($C_{3-7}$)cycloalkyl-heteroaryl-, ($C_{3-7}$)heterocycloalkyl-heteroaryl- or ($C_{4-9}$)heterobicycloalkyl-heteroaryl-, any of which groups may be optionally substituted by one or more substituents.

Appositely, $R^1$ represents halogen; or $R^1$ represents heteroaryl, $(C_{3-7})$cycloalkyl-heteroaryl- or $(C_{3-7})$heterocycloalkyl-heteroaryl-, any of which groups may be optionally substituted by one or more substituents.

More appositely, $R^1$ represents heteroaryl, $(C_{3-7})$cycloalkyl-heteroaryl- or $(C_{3-7})$heterocycloalkyl-heteroaryl-, any of which groups may be optionally substituted by one or more substituents.

Suitably, $R^1$ represents halogen; or $R^1$ represents heteroaryl or $(C_{3-7})$cycloalkyl-heteroaryl-, either of which groups may be optionally substituted by one or more substituents.

More suitably, $R^1$ represents heteroaryl or $(C_{3-7})$cycloalkyl-heteroaryl-, either of which groups may be optionally substituted by one or more substituents.

In a first embodiment, $R^1$ represents hydrogen.

In a second embodiment, $R^1$ represents halogen. In one aspect of that embodiment, $R^1$ represents fluoro. In another aspect of that embodiment, $R^1$ represents chloro.

In a third embodiment, $R^1$ represents cyano.

In a fourth embodiment, $R^1$ represents optionally substituted aryl. In one aspect of that embodiment, $R^1$ represents optionally substituted phenyl.

In fifth embodiment, $R^1$ represents optionally substituted $C_{3-7}$ heterocycloalkyl.

In one aspect of that embodiment, $R^1$ represents optionally substituted azetidinyl.

In a sixth embodiment, $R^1$ represents optionally substituted $(C_{3-7})$heterocycloalkenyl. In a first aspect of that embodiment, $R^1$ represents optionally substituted 1,2-dihydropyridinyl. In a second aspect of that embodiment, $R^1$ represents optionally substituted 1,2-dihydropyrimidinyl.

In a seventh embodiment, $R^1$ represents optionally substituted heteroaryl. In one aspect of that embodiment, $R^1$ represents optionally substituted pyridinyl. In another aspect of that embodiment, $R^1$ represents optionally substituted pyrimidinyl.

In an eighth embodiment, $R^1$ represents optionally substituted heteroaryl-aryl-. In one aspect of that embodiment, $R^1$ represents optionally substituted imidazolylphenyl-.

In a ninth embodiment, $R^1$ represents optionally substituted $(C_{3-7})$cycloalkyl-heteroaryl-. In a first aspect of that embodiment, $R^1$ represents optionally substituted cyclohexylpyrazolyl-. In a second aspect of that embodiment, $R^1$ represents optionally substituted cyclopropylpyridinyl-. In a third aspect of that embodiment, $R^1$ represents optionally substituted cyclobutylpyridinyl-. In a fourth aspect of that embodiment, $R^1$ represents optionally substituted cyclopentylpyridinyl-. In a fifth aspect of that embodiment, $R^1$ represents optionally substituted cyclohexylpyridinyl-. In a sixth aspect of that embodiment, $R^1$ represents optionally substituted cyclopropylpyrimidinyl-. In a seventh aspect of that embodiment, $R^1$ represents optionally substituted cyclobutylpyrimidinyl-. In an eighth aspect of that embodiment, $R^1$ represents optionally substituted cyclopentylpyrimidinyl-. In a ninth aspect of that embodiment, $R^1$ represents optionally substituted cyclohexylpyrimidinyl-. In a tenth aspect of that embodiment, $R^1$ represents optionally substituted cyclohexylpyrazinyl-.

In a tenth embodiment, $R^1$ represents optionally substituted $(C_{4-9})$bicycloalkyl-heteroaryl-.

In an eleventh embodiment, $R^1$ represents optionally substituted $(C_3-7)$heterocycloalkyl-heteroaryl-. In a first aspect of that embodiment, $R^1$ represents substituted azetidinylpyrazolyl-. In a second aspect of that embodiment, $R^1$ represents optionally substituted pyrrolidinylpyridinyl-. In a third aspect of that embodiment, $R^1$ represents optionally substituted tetrahydropyranylpyridinyl-. In a fourth aspect of that embodiment, $R^1$ represents optionally substituted piperidinylpyridinyl-. In a fifth aspect of that embodiment, $R^1$ represents optionally substituted piperazinylpyridinyl-. In a sixth aspect of that embodiment, $R^1$ represents optionally substituted morpholinylpyridinyl-. In a seventh aspect of that embodiment, $R^1$ represents optionally substituted thiomorpholinylpyridinyl-. In an eighth aspect of that embodiment, $R^1$ represents optionally substituted diazepanylpyridinyl-. In a ninth aspect of that embodiment, $R^1$ represents optionally substituted oxetanylpyrimidinyl-. In a tenth aspect of that embodiment, $R^1$ represents optionally substituted azetidinylpyrimidinyl-. In an eleventh aspect of that embodiment, $R^1$ represents optionally substituted tetrahydrofuranylpyrimidinyl-. In a twelfth aspect of that embodiment, $R^1$ represents substituted tetrahydrothienyl-pyrimidinyl-. In a thirteenth aspect of that embodiment, $R^1$ represents optionally substituted pyrrolidinylpyrimidinyl-. In a fourteenth aspect of that embodiment, $R^1$ represents optionally substituted tetrahydropyranylpyrimidinyl-. In a fifteenth aspect of that embodiment, $R^1$ represents optionally substituted dioxanylpyrimidinyl-. In a sixteenth aspect of that embodiment, $R^1$ represents optionally substituted piperidinylpyrimidinyl-. In a seventeenth aspect of that embodiment, $R^1$ represents optionally substituted piperazinylpyrimidinyl-. In an eighteenth aspect of that embodiment, $R^1$ represents optionally substituted morpholinylpyrimidinyl-. In a nineteenth aspect of that embodiment, $R^1$ represents optionally substituted thiomorpholinylpyrimidinyl-. In a twentieth aspect of that embodiment, $R^1$ represents optionally substituted azepanylpyrimidinyl-. In a twenty-first aspect of that embodiment, $R^1$ represents optionally substituted oxazepanylpyrimidinyl-. In a twenty-second aspect of that embodiment, $R^1$ represents optionally substituted diazepanylpyrimidinyl-. In a twenty-third aspect of that embodiment, $R^1$ represents optionally substituted thiadiazepanylpyrimidinyl-. In a twenty-fourth aspect of that embodiment, $R^1$ represents optionally substituted oxetanylpyrazinyl-. In a twenty-fifth aspect of that embodiment, $R^1$ represents optionally substituted piperidinylpyrazinyl-.

In a twelfth embodiment, $R^1$ represents optionally substituted $(C_{4-9})$heterobicycloalkyl-heteroaryl-. In a first aspect of that embodiment, $R^1$ represents optionally substituted (2-oxa-5-azabicyclo[2.2.1]heptanyl)pyrimidinyl-. In a second aspect of that embodiment, $R^1$ represents optionally substituted (3-oxa-8-azabicyclo-[3.2.1]octanyl)pyrimidinyl-. In a third aspect of that embodiment, $R^1$ represents optionally substituted (3,6-diazabicyclo[3.2.2]nonanyl)pyrimidinyl-. In a fourth aspect of that embodiment, $R^1$ represents optionally substituted (3,7-dioxa-9-azabicyclo[3.3.1]-nonanyl)pyrimidinyl-.

In a thirteenth embodiment, $R^1$ represents optionally substituted $(C_{4-9})$spiro-heterocycloalkyl-heteroaryl-.

Appositely, $R^1$ represents fluoro, chloro or cyano; or $R^1$ represents phenyl, azetidinyl, dihydropyridinyl, dihydropyrimidinyl, pyrazolyl, pyridinyl, pyrimidinyl, imidazolylphenyl, cyclopropylpyridinyl, cyclobutylpyridinyl, cyclobutylpyrimidinyl, cyclohexylpyrimidinyl, azetidinylpyrazolyl, oxetanylpyridinyl, azetidinylpyridinyl, pyrrolidinylpyridinyl, piperazinylpyridinyl, oxetanylpyrimidinyl, azetidinylpyrimidinyl, tetrahydrofuranylpyrimidinyl, tetrahydrothienylpyrimidinyl, pyrrolidinylpyrimidinyl, tetrahydropyranylpyrimidinyl, dioxanylpyrimidinyl, piperazinylpyrimidinyl, morpholinylpyrimidinyl, thiomorpholinylpyrimidinyl, diazepanylpyrimidinyl, (2-oxa-5-azabicyclo-[2.2.1]heptanyl)pyrimidinyl, (3-oxa-8-azabicyclo[3.2.1]octanyl)pyrimidinyl, (3,6-diazabicyclo[3.2.2]nonanyl)pyrimidinyl or (3,7-dioxa-9-azabicyclo[3.3.1]nonanyl)pyrimidinyl, any of which groups may be optionally substituted by one or more substituents. Additionally, $R^1$ may represent optionally substituted cyclopentylpyridinyl.

More typically, $R^1$ represents fluoro or chloro; or $R^1$ represents pyrimidinyl, cyclobutylpyrimidinyl, cyclopentylpyrimidinyl, cyclohexylpyrimidinyl, oxetanylpyrimidinyl, tetrahydrofuranylpyrimidinyl, pyrrolidinylpyrimidinyl, tetrahydropyranylpyrimidinyl, dioxanylpyrimidinyl or morpholinylpyrimidinyl, any of which groups may be optionally substituted by one or more substituents.

Generally, $R^1$ represents chloro; or $R^1$ represents pyrimidinyl, cyclobutylpyridinyl, cyclopentylpyridinyl, cyclobutylpyrimidinyl, azetidinylpyrimidinyl or piperazinylpyrimidinyl, any of which groups may be optionally substituted by one or more substituents.

More generally, $R^1$ represents pyrimidinyl, cyclobutylpyridinyl, cyclopentylpyridinyl, cyclobutylpyrimidinyl, azetidinylpyrimidinyl or piperazinylpyrimidinyl, any of which groups may be optionally substituted by one or more substituents.

Still more typically, $R^1$ represents chloro; or $R^1$ represents pyrimidinyl or cyclobutylpyrimidinyl, either of which groups may be optionally substituted by one or more substituents.

Illustratively, $R^1$ represents pyrimidinyl or cyclobutylpyrimidinyl, either of which groups may be optionally substituted by one or more substituents.

Typical examples of optional substituents on $R^1$ include one, two or three substituents independently selected from halogen, halo($C_{1-6}$)alkyl, cyano, cyano($C_{1-6}$)alkyl, nitro($C_{1-6}$)alkyl, $C_{1-6}$ alkyl, phosphate($C_{1-6}$)alkyl, ($C_{1-6}$)alkyl-phosphate($C_{1-6}$)alkyl, phosphate($C_{1-6}$)alkoxy($C_{1-6}$)alkyl, sulphate($C_{1-6}$)alkyl, difluoromethyl, trifluoromethyl, trifluoroethyl, $C_{2-6}$ alkenyl, hydroxy, hydroxy($C_{1-6}$)alkyl, $C_{1-6}$ alkoxy, ($C_{1-6}$)alkoxy($C_{1-6}$)alkyl, trifluoroethoxy, carboxy($C_{3-7}$)cycloalkyloxy, $C_{1-6}$ alkylthio, $C_{1-6}$ alkylsulphonyl, ($C_{1-6}$)alkylsulphonyl($C_{1-6}$)alkyl, oxo, amino, amino($C_{1-6}$)alkyl, $C_{1-6}$ alkylamino, di($C_{1-6}$)alkylamino, di($C_{1-6}$)alkylamino($C_{1-6}$)alkyl, ($C_{1-6}$)alkoxy($C_{1-6}$)alkylamino, N—[($C_{1-6}$)alkyl]-N—[hydroxy($C_{1-6}$)alkyl]amino, ($C_{2-6}$)alkylcarbonylamino($C_{1-6}$)alkyl, ($C_{2-6}$)alkoxycarbonylamino($C_{1-6}$)alkyl, $C_{1-6}$ alkylsulphinylamino, $C_{1-6}$ alkylsulphonylamino, N—[($C_{1-6}$)alkyl]-N—[($C_{1-6}$)alkylsulphonyl]amino, bis[($C_{1-6}$)alkylsulphonyl]amino, ($C_{1-6}$)alkylsulphonylamino-($C_{1-6}$)alkyl, N—[($C_{1-6}$)alkyl]-N—[carboxy($C_{1-6}$)alkyl]amino, carboxy($C_{3-7}$)cycloalkylamino, carboxy($C_{3-7}$)cycloalkyl($C_{1-6}$)alkylamino, imino, formyl, $C_{2-6}$ alkylcarbonyl, ($C_{2-6}$)alkyl-carbonyloxy($C_{1-6}$)alkyl, carboxy, carboxy($C_{1-6}$)alkyl, $C_{2-6}$ alkoxycarbonyl, $C_{2-6}$ alkoxycarbonyl($C_{1-6}$)alkyl, morpholinyl($C_{1-6}$)alkoxycarbonyl, $C_{2-6}$ alkoxycarbonylmethylidenyl, aminocarbonyl, aminosulphonyl, ($C_{1-6}$)alkylsulphoximinyl and [($C_{1-6}$)alkyl][N—($C_{1-6}$)alkyl]sulphoximinyl.

Illustrative examples of optional substituents on $R^1$ include one, two or three substituents independently selected from halogen, cyano, $C_{1-6}$ alkyl, difluoromethyl, hydroxy($C_{1-6}$)alkyl, oxo, amino and amino($C_{1-6}$)alkyl.

Selected examples of optional substituents on $R^1$ include one, two or three substituents independently selected from halogen, trifluoromethyl, hydroxy, hydroxy($C_{1-6}$)alkyl, oxo, amino and amino($C_{1-6}$)alkyl.

Particular examples of optional substituents on $R^1$ include one, two or three substituents independently selected from hydroxy($C_{1-6}$)alkyl, amino and amino($C_{1-6}$)alkyl.

Typical examples of particular substituents on $R^1$ include one, two or three substituents independently selected from fluoro, chloro, fluoromethyl, fluoroisopropyl, cyano, cyanoethyl, cyanoisopropyl, nitromethyl, methyl, ethyl, isopropyl, isopropylmethyl, phosphate-isopropyl, ethylphosphate-isopropyl, phosphate-methoxyisopropyl, sulphate-isopropyl, difluoromethyl, trifluoromethyl, trifluoroethyl, ethenyl, hydroxy, hydroxymethyl, hydroxyisopropyl, hydroxyisobutyl, methoxy, isopropoxy, methoxyisopropyl, trifluoroethoxy, carboxycyclobutyloxy, methylthio, methylsulphonyl, methylsulphonylmethyl, methylsulphonylethyl, oxo, amino, aminomethyl, aminoisopropyl, methylamino, dimethylamino, dimethylaminoisopropyl, methoxyethylamino, N-(hydroxyethyl)-N-(methyl)amino, acetylaminomethyl, acetylaminoisopropyl, methoxy-carbonylaminoisopropyl, (tert-butoxycarbonyl)aminoisopropyl, (tert-butyl)sulphinylamino, methylsulphonylamino, (tert-butyl)sulphonylamino, N-methyl-N-(methyl-sulphonyl)amino, bis(methylsulphonyl)amino, methylsulphonylaminoisopropyl, N-(carboxyethyl)-N-(methyl)amino, carboxycyclopentylamino, carboxycyclopropylmethyl-amino, imino, formyl, acetyl, (tert-butyl)carbonyl, acetoxyisopropyl, carboxy, carboxymethyl, carboxyethyl, methoxycarbonyl, ethoxycarbonyl, n-butoxycarbonyl, tert-butoxycarbonyl, methoxycarbonylmethyl, ethoxycarbonylmethyl, ethoxycarbonylethyl, morpholinylethoxycarbonyl, ethoxycarbonylmethylidenyl, aminocarbonyl, aminosulphonyl, methylsulphoximinyl and (methyl)(N-methyl)sulphoximinyl.

Illustrative examples of particular substituents on $R^1$ include one, two or three substituents independently selected from fluoro, cyano, methyl, difluoromethyl, hydroxyisopropyl, oxo, amino and aminoisopropyl.

Selected examples of particular substituents on $R^1$ include one, two or three substituents independently selected from fluoro, trifluoromethyl, hydroxy, hydroxyisopropyl, oxo, amino and aminoisopropyl.

Suitable examples of particular substituents on $R^1$ include one, two or three substituents independently selected from hydroxyisopropyl, amino and aminoisopropyl.

In a particular embodiment, $R^1$ is substituted by hydroxy($C_{1-6}$)alkyl. In one aspect of that embodiment, $R^1$ is substituted by hydroxyisopropyl, especially 2-hydroxyprop-2-yl.

In another embodiment, $R^1$ is substituted by amino($C_{1-6}$)alkyl. In one aspect of that embodiment, $R^1$ is substituted by aminoisopropyl, especially 2-aminoprop-2-yl.

Illustrative values of $R^1$ include fluoro, chloro, cyano, (methyl)(methylthio)phenyl, methylsulphonylphenyl, (methyl)(methylsulphonyl)phenyl, methylsulphoximinylphenyl, (hydroxyisopropyl)azetidinyl, methylpyrazolyl, hydroxyisopropylpyridinyl, (hydroxyisopropyl)(methyl)pyridinyl, methoxypyridinyl, oxopyridinyl, (methyl)(oxo)pyridinyl, cyanoisopropylpyrimidinyl, phosphate-isopropylpyrimidinyl, sulphate-isopropylpyrimidinyl, hydroxyisopropylpyrimidinyl, (hydroxyisopropyl)(methyl)-pyrimidinyl, (dimethyl)(hydroxyisopropyl)pyrimidinyl, (difluoromethyl)-(hydroxyisopropyl)pyrimidinyl, (hydroxyisopropyl)(trifluoromethyl)pyrimidinyl, hydroxyisobutylpyrimidinyl, methoxyisopropylpyrimidinyl, oxopyrimidinyl, aminoisopropylpyrimidinyl, (dimethylamino)isopropylpyrimidinyl, acetylaminoisopropylpyrimidinyl, (methoxycarbonyl)aminoisopropylpyrimidinyl, (tert-butoxycarbonyl)aminoisopropylpyrimidinyl, (methylsulphonyl)aminoisopropylpyrimidinyl, methylsulphoximinylpyridinyl, (dimethyl)imidazolylphenyl, methylsulphonylcyclopropyl-pyridinyl, aminocyclobutylpyridinyl, (tert-butyl)sulphinylaminocyclobutylpyridinyl, (dihydroxy)(methyl)cyclobutylpyrimidinyl, amino cyclobutylpyrimidinyl, (amino)(cyano)cyclobutylpyrimidinyl, (amino)(difluoromethyl)cyclobutylpyrimidinyl, aminocyclopentyl-pyrimidinyl, (difluoro)(hydroxy)cyclohexylpyrimidinyl, (dihydroxy)(methyl)cyclohexylpyrimidinyl, (amino)(difluoro)cyclohexylpyrimidinyl, (methylsulphonyl) azetidinylpyrazolyl, aminooxetanylpyridinyl, (tert-butyl) sulphinylaminooxetanylpyridinyl, (tert-butyl)sulphonylaminooxetanylpyridinyl, pyrrolidinylpyridinyl, (hydroxy) pyrrolidinylpyridinyl, (tert-butoxycarbonyl)(hydroxy) pyrrolidinylpyridinyl, piperazinylpyridinyl, (methylsulphonyl)piperazinylpyridinyl, (hydroxy)oxetanylpyrimidinyl, (amino)oxetanylpyrimidinyl, (difluoro)azetidinylpyrimidinyl, (cyano)(methyl)azetidinylpyrimidinyl, (hydroxy)(methyl)azetidinylpyrimidinyl, (hydroxy)(trifluoromethyl)azetidinylpyrimidinyl, [(hydroxy)(trifluoromethyl)azetidinyl](methyl)pyrimidinyl, (hydroxyisopropyl) (tetrahydrofuranyl)pyrimidinyl, aminotetrahydrofuranylpyrimidinyl, (hydroxy)tetrahydrothienylpyrimidinyl, (hydroxy)(oxo)tetrahydrothienylpyrimidinyl, (hydroxy)(dioxo)tetrahydrothienylpyrimidinyl, pyrrolidinylpyrimidinyl, methylpyrrolidinylpyrimidinyl, tetrahydropyranylpyrimidinyl, aminotetrahydropyranylpyrimidinyl, (amino)(dimethyl)dioxanylpyrimidinyl, (hydroxyisopropyl)piperidinylpyrimidinyl, (aminoisopropyl) piperidinylpyrimidinyl, (oxo)piperazinylpyrimidinyl, morpholinylpyrimidinyl, methylmorpholinylpyrimidinyl, aminomorpholinylpyrimidinyl, thiomorpholinylpyrimidinyl, (oxo)thiomorpholinylpyrimidinyl, (dioxo)thiomorpholinylpyrimidinyl, (amino)(dioxo)thiomorpholinylpyrimidinyl, (oxo)diazepanylpyrimidinyl, hydroxyisopropyl-(3-azabicyclo[3.1.0]hexanyl)pyrimidinyl, (2-oxa-5-azabicyclo [2.2.1]-heptanyl)pyrimidinyl, (3-oxa-8-azabicyclo[3.2.1] octanyl)pyrimidinyl, (oxo)(3,6-diazabicyclo[3.2.2]nonanyl) pyrimidinyl and (3,7-dioxa-9-azabicyclo[3.3.1]nonanyl) pyrimidinyl. Additional values include (amino cyclobutyl) (fluoro)pyridinyl and (aminocyclopentyl)(fluoro)pyridinyl.

Typical values of $R^1$ include fluoro, chloro, hydroxyisopropylpyrimidinyl, aminoisopropylpyrimidinyl, aminocyclobutylpyrimidinyl, (amino)(cyano)cyclobutylpyrimidinyl, (amino)(difluoromethyl)cyclobutylpyrimidinyl, aminocyclopentylpyrimidinyl, (amino)(difluoro)cyclohexylpyrimidinyl, (amino)oxetanylpyrimidinyl, aminotetrahydrofuranylpyrimidinyl, pyrrolidinylpyrimidinyl, methylpyrrolidinyl-pyrimidinyl, aminotetrahydropyranylpyrimidinyl, (amino)(dimethyl)dioxanylpyrimidinyl, (hydroxyisopropyl)piperidinylpyrimidinyl, (aminoisopropyl)piperidinylpyrimidinyl, morpholinylpyrimidinyl, methylmorpholinylpyrimidinyl, aminomorpholinylpyrimidinyl, (dioxo)thiomorpholinylpyrimidinyl, (amino)(dioxo)thiomorpholinylpyrimidinyl and hydroxyisopropyl-(3-azabicyclo[3.1.0]hexanyl)pyrimidinyl. Additional values include (aminocyclobutyl)(fluoro)pyridinyl, (aminocyclopentyl) (fluoro)pyridinyl, (hydroxy)(trifluoromethyl)azetidinylpyrimidinyl and (oxo)piperazinylpyrimidinyl.

Particular values of $R^1$ include chloro, hydroxyisopropylpyrimidinyl, aminoisopropylpyrimidinyl, (amino cyclobutyl)(fluoro)pyridinyl, (aminocyclopentyl)(fluoro)pyridinyl, aminocyclobutylpyrimidinyl, (hydroxy)(trifluoromethyl) azetidinylpyrimidinyl and (oxo)piperazinylpyrimidinyl.

Selected values of $R^1$ include chloro, hydroxyisopropylpyrimidinyl, aminoisopropylpyrimidinyl and aminocyclobutylpyrimidinyl.

In a first embodiment, $R^1$ represents hydroxyisopropylpyrimidinyl, especially 2-(2-hydroxypropan-2-yl)pyrimidin-5-yl.

In a second embodiment, $R^1$ represents aminoisopropylpyrimidinyl, especially 2-(2-aminopropan-2-yl)pyrimidin-5-yl.

In a third embodiment, $R^1$ represents (aminocyclobutyl) (fluoro)pyridinyl, especially 2-(1-aminocyclobutyl)-3-fluoropyridin-5-yl.

In a fourth embodiment, $R^1$ represents (aminocyclopentyl)(fluoro)pyridinyl, especially 2-(1-aminocyclopentyl)-3-fluoropyridin-5-yl.

In a fifth embodiment, $R^1$ represents aminocyclobutylpyrimidinyl, especially 2-(1-aminocyclobutyl)pyrimidin-5-yl.

Generally, $R^2$ represents hydrogen, halogen, trifluoromethyl, trifluoromethoxy or —OR$^a$; or $R^2$ represents $C_{1-6}$ alkyl or heteroaryl, either of which groups may be optionally substituted by one or more substituents.

Typically, $R^2$ represents hydrogen or halogen; or $R^2$ represents heteroaryl, which group may be optionally substituted by one or more substituents.

Appositely, $R^2$ represents halogen; or $R^2$ represents heteroaryl, which group may be optionally substituted by one or more substituents.

Suitably, $R^2$ represents hydrogen or halogen.

In a first embodiment, $R^2$ represents hydrogen. In a second embodiment, $R^2$ represents halogen. In one aspect of that embodiment, $R^2$ represents fluoro. In another aspect of that embodiment, $R^2$ represents chloro. In a third embodiment, $R^2$ represents cyano. In a fourth embodiment, $R^2$ represents nitro. In a fifth embodiment, $R^2$ represents hydroxy. In a sixth embodiment, $R^2$ represents trifluoromethyl. In a seventh embodiment, $R^2$ represents trifluoromethoxy. In an eighth embodiment, $R^2$ represents —OR$^a$. In a ninth embodiment, $R^2$ represents optionally substituted $C_{1-6}$ alkyl. In a first aspect of that embodiment, $R^2$ represents methyl. In a second aspect of that embodiment, $R^2$ represents ethyl. In a tenth embodiment, $R^2$ represents optionally substituted heteroaryl. In a first aspect of that embodiment, $R^2$ represents optionally substituted pyrimidinyl.

Typical examples of optional substituents on $R^2$ include one, two or three substituents independently selected from hydroxy($C_{1-6}$)alkyl and $C_{2-6}$ alkoxycarbonyl.

Suitable examples of optional substituents on $R^2$ include one, two or three substituents independently selected from hydroxy($C_{1-6}$)alkyl.

Typical examples of particular substituents on $R^2$ include one, two or three substituents independently selected from hydroxyisopropyl and ethoxycarbonyl.

Suitable examples of particular substituents on $R^2$ include one, two or three substituents independently selected from hydroxyisopropyl.

Typical values of $R^2$ include hydrogen, fluoro, chloro, trifluoromethyl, trifluoromethoxy, —OR$^a$, methyl, ethoxycarbonylethyl and hydroxyisopropylpyrimidinyl.

Selected values of $R^2$ include hydrogen, fluoro and chloro.

Illustrative values of $R^2$ include hydrogen and chloro.

Typically, $R^3$ represents hydrogen, halogen or $C_{1-6}$ alkyl.

In a first embodiment, $R^3$ represents hydrogen. In a second embodiment, $R^3$ represents halogen. In one aspect of that embodiment, $R^3$ represents fluoro. In a third embodiment, $R^3$ represents optionally substituted $C_{1-6}$ alkyl. In one aspect of that embodiment, $R^3$ represents methyl. In another aspect of that embodiment, $R^3$ represents ethyl.

Typically, $R^4$ represents hydrogen, halogen or $C_{1-6}$ alkyl.

In a first embodiment, $R^4$ represents hydrogen. In a second embodiment, $R^4$ represents halogen. In one aspect of that embodiment, $R^4$ represents fluoro. In a third embodiment, $R^4$ represents optionally substituted $C_{1-6}$ alkyl. In one aspect of that embodiment, $R^4$ represents methyl. In another aspect of that embodiment, $R^4$ represents ethyl.

Generally, $R^5$ represents halogen, cyano, difluoromethoxy, trifluoromethoxy, —$OR^a$ or $C_{1-6}$ alkylsulphonyl; or $R^5$ represents $C_{1-6}$ alkyl, which group may be optionally substituted by one or more substituents.

Typically, $R^5$ represents difluoromethoxy or —$OR^a$.

In a first embodiment, $R^5$ represents hydrogen. In a second embodiment, $R^5$ represents halogen. In one aspect of that embodiment, $R^5$ represents fluoro. In another aspect of that embodiment, $R^5$ represents chloro. In a third embodiment, $R^5$ represents hydroxy. In a fourth embodiment, $R^5$ represents cyano. In a fifth embodiment, $R^5$ represents trifluoromethyl. In a sixth embodiment, $R^5$ represents difluoromethoxy. In a seventh embodiment, $R^5$ represents trifluoromethoxy. In an eighth embodiment, $R^5$ represents —$OR^a$. In one aspect of that embodiment, $R^5$ represents methoxy. In a ninth embodiment, $R^5$ represents $C_{1-6}$ alkylsulphonyl. In one aspect of that embodiment, $R^5$ represents methylsulphonyl. In a tenth embodiment, $R^5$ represents optionally substituted $C_{1-6}$ alkyl. In one aspect of that embodiment, $R^5$ represents methyl. In another aspect of that embodiment, $R^5$ represents ethyl.

Appositely, $R^5$ represents difluoromethoxy or methoxy.

Generally, $R^6$ represents hydrogen, halogen or trifluoromethyl.

In a first embodiment, $R^6$ represents hydrogen. In a second embodiment, $R^6$ represents halogen. In one aspect of that embodiment, $R^6$ represents fluoro. In another aspect of that embodiment, $R^6$ represents chloro. In a third embodiment, $R^6$ represents trifluoromethyl. In a fourth embodiment, $R^6$ represents $C_{1-6}$ alkyl. In one aspect of that embodiment, $R^6$ represents methyl. In another aspect of that embodiment, $R^6$ represents ethyl. In a fifth embodiment, $R^6$ represents $C_{1-6}$ alkoxy. In one aspect of that embodiment, $R^6$ represents methoxy.

Generally, $R^7$ represents hydrogen or trifluoromethyl.

In a first embodiment, $R^7$ represents hydrogen. In a second embodiment, $R^7$ represents halogen. In one aspect of that embodiment, $R^7$ represents fluoro. In another aspect of that embodiment, $R^7$ represents chloro. In a third embodiment, $R^7$ represents trifluoromethyl. In a fourth embodiment, $R^7$ represents $C_{1-6}$ alkyl. In one aspect of that embodiment, $R^7$ represents methyl. In another aspect of that embodiment, $R^7$ represents ethyl. In a fifth embodiment, $R^7$ represents $C_{1-6}$ alkoxy. In one aspect of that embodiment, $R^7$ represents methoxy.

Generally, $R^8$ represents hydrogen or trifluoromethyl.

In a first embodiment, $R^8$ represents hydrogen. In a second embodiment, $R^8$ represents halogen. In one aspect of that embodiment, $R^8$ represents fluoro. In another aspect of that embodiment, $R^8$ represents chloro. In a third embodiment, $R^8$ represents trifluoromethyl. In a fourth embodiment, $R^8$ represents $C_{1-6}$ alkyl. In one aspect of that embodiment, $R^8$ represents methyl. In another aspect of that embodiment, $R^8$ represents ethyl. In a fifth embodiment, $R^8$ represents $C_{1-6}$ alkoxy. In one aspect of that embodiment, $R^8$ represents methoxy.

Typically, $R^{12}$ represents hydrogen or methyl.

In a first embodiment, $R^{12}$ represents hydrogen. In a second embodiment, $R^{12}$ represents $C_{1-6}$ alkyl. In one aspect of that embodiment, $R^{12}$ represents methyl. In another aspect of that embodiment, $R^{12}$ represents ethyl.

Typical examples of suitable substituents which may be present on $R^a$, $R^b$, $R^c$, $R^d$ or $R^e$, or on the heterocyclic moiety —$NR^bR^c$, include halogen, $C_{1-6}$ alkyl, $C_{1-6}$ alkoxy, difluoromethoxy, trifluoromethoxy, $C_{1-6}$ alkoxy($C_{1-6}$)alkyl, $C_{1-6}$ alkylthio, $C_{1-6}$ alkylsulphinyl, $C_{1-6}$ alkylsulphonyl, hydroxy, hydroxy($C_{1-6}$)alkyl, amino($C_{1-6}$)alkyl, cyano, trifluoromethyl, oxo, $C_{2-6}$ alkylcarbonyl, carboxy, $C_{2-6}$ alkoxycarbonyl, $C_{2-6}$ alkylcarbonyloxy, amino, $C_{1-6}$ alkylamino, di($C_{1-6}$)alkylamino, phenylamino, pyridinylamino, $C_{2-6}$ alkylcarbonylamino, $C_{2-6}$ alkylcarbonylamino($C_{1-6}$)alkyl, $C_{2-6}$ alkoxycarbonylamino, $C_{1-6}$ alkylsulphonylamino, aminocarbonyl, $C_{1-6}$ alkylaminocarbonyl and di($C_{1-6}$)alkylaminocarbonyl.

Typical examples of specific substituents which may be present on $R^a$, $R^b$, $R^c$, $R^d$ or $R^e$, or on the heterocyclic moiety —$NR^bR^c$, include fluoro, chloro, bromo, methyl, ethyl, isopropyl, methoxy, isopropoxy, difluoromethoxy, trifluoromethoxy, methoxymethyl, methylthio, ethylthio, methylsulphinyl, methylsulphonyl, hydroxy, hydroxymethyl, hydroxyethyl, aminomethyl, cyano, trifluoromethyl, oxo, acetyl, carboxy, methoxycarbonyl, ethoxycarbonyl, tert-butoxycarbonyl, acetoxy, amino, methylamino, ethylamino, dimethylamino, phenylamino, pyridinylamino, acetylamino, tert-butoxycarbonylamino, acetylaminomethyl, methylsulphonylamino, aminocarbonyl, methylaminocarbonyl and dimethylaminocarbonyl.

Suitably, $R^a$ represents $C_{1-6}$ alkyl, aryl($C_{1-6}$)alkyl or heteroaryl($C_{1-6}$)alkyl, any of which groups may be optionally substituted by one or more substituents.

Selected values of $R^a$ include methyl, ethyl, benzyl and isoindolylpropyl, any of which groups may be optionally substituted by one or more substituents.

Selected examples of suitable substituents on $R^a$ include $C_{1-6}$ alkoxy and oxo.

Selected examples of specific substituents on $R^a$ include methoxy and oxo.

In one embodiment, $R^a$ represents optionally substituted $C_{1-6}$ alkyl. In one aspect of that embodiment, $R^a$ ideally represents unsubstituted $C_{1-6}$ alkyl, especially methyl. In another aspect of that embodiment, $R^a$ ideally represents substituted $C_{1-6}$ alkyl, e.g. methoxyethyl. In another embodiment, $R^a$ represents optionally substituted aryl. In one aspect of that embodiment, $R^a$ represents unsubstituted aryl, especially phenyl. In another aspect of that embodiment, $R^a$ represents monosubstituted aryl, especially methylphenyl. In another embodiment, $R^a$ represents optionally substituted aryl($C_{1-6}$)alkyl, ideally unsubstituted aryl($C_{1-6}$)alkyl, especially benzyl. In a further embodiment, $R^a$ represents optionally substituted heteroaryl. In a further embodiment, $R^a$ represents optionally substituted heteroaryl($C_{1-6}$)alkyl, e.g. dioxoisoindolylpropyl.

Specific values of $R^a$ include methyl, methoxyethyl, benzyl and dioxoisoindolylpropyl.

In a particular aspect, $R^b$ represents hydrogen or trifluoromethyl; or $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl or heteroaryl($C_{1-6}$)alkyl, any of which groups may be optionally substituted by one or more substituents.

Selected values of $R^b$ include hydrogen; or $C_{1-6}$ alkyl, aryl($C_{1-6}$)alkyl, $C_{3-7}$ heterocycloalkyl or $C_{3-7}$ heterocycloalkyl($C_{1-6}$)alkyl, any of which groups may be optionally substituted by one or more substituents.

Typical values of $R^b$ include hydrogen and $C_{1-6}$ alkyl.

Illustratively, $R^b$ represents hydrogen or trifluoromethyl; or methyl, ethyl, n-propyl, isopropyl, n-butyl, 2-methylpropyl, tert-butyl, pentyl, hexyl, cyclopropyl, cyclobutyl, cyclopentyl, cyclohexyl, cyclopropylmethyl, cyclobutylmethyl, cyclopentylmethyl, cyclohexylmethyl, phenyl, benzyl, phenylethyl, azetidinyl, tetrahydrofuryl, tetrahydrothienyl, pyrrolidinyl, piperidinyl, homopiperidinyl, morpholinyl, azetidinylmethyl, tetrahydrofurylmethyl, pyrrolidinylmethyl, pyrrolidinylethyl, pyrrolidinylpropyl, thiazolidinylmethyl, imidazolidinylethyl, piperidinylmethyl, piperidinylethyl, tetrahydroquinolinylmethyl, piperazinylpropyl, morpholinylmethyl, morpholinylethyl, morpholinylpropyl, pyridinyl, indolylmethyl, pyrazolylmethyl, pyrazolylethyl, imidazolylmethyl, imidazolylethyl, benzimidazolylmethyl, triazolylmethyl, pyridinylmethyl or pyridinylethyl, any of which groups may be optionally substituted by one or more substituents.

Representative values of $R^b$ include hydrogen; or methyl, ethyl, n-propyl, benzyl, pyrrolidinyl or morpholinylpropyl, any of which groups may be optionally substituted by one or more substituents.

Selected examples of suitable substituents on $R^b$ include $C_{1-6}$ alkoxy, $C_{1-6}$ alkylthio, $C_{1-6}$ alkylsulphinyl, $C_{1-6}$ alkylsulphonyl, hydroxy, cyano, $C_{2-6}$ alkoxycarbonyl, di-$(C_{1-6})$ alkylamino and $C_{2-6}$ alkoxycarbonylamino.

Selected examples of specific substituents on $R^b$ include methoxy, methylthio, methylsulphinyl, methylsulphonyl, hydroxy, cyano, tert-butoxycarbonyl, dimethylamino and tert-butoxycarbonylamino.

Specific values of $R^b$ include hydrogen, methyl, methoxyethyl, methylthioethyl, methylsulphinylethyl, methylsulphonylethyl, hydroxyethyl, cyanoethyl, dimethylamino-ethyl, tert-butoxycarbonylaminoethyl, dihydroxypropyl, benzyl, pyrrolidinyl, tert-butoxycarbonylpyrrolidinyl and morpholinylpropyl.

In one embodiment, $R^b$ represents hydrogen. In another embodiment, $R^b$ represents $C_{1-6}$ alkyl, especially methyl.

Selected values of $R^c$ include hydrogen; or $C_{1-6}$ alkyl, $C_{3-7}$ cycloalkyl or $C_{3-7}$ heterocycloalkyl, any of which groups may be optionally substituted by one or more substituents.

In a particular aspect, $R^c$ represents hydrogen, $C_{1-6}$ alkyl or $C_{3-7}$ cycloalkyl.

Representative values of $R^c$ include hydrogen; or methyl, cyclobutyl, cyclopentyl, cyclohexyl, tetrahydropyranyl and piperidinyl, any of which groups may be optionally substituted by one or more substituents.

Selected examples of suitable substituents on $R^c$ include $C_{2-6}$ alkylcarbonyl and $C_{2-6}$ alkoxycarbonyl.

Selected examples of specific substituents on $R^c$ include acetyl and tert-butoxycarbonyl.

Specific values of $R^c$ include hydrogen, methyl, cyclobutyl, cyclopentyl, cyclohexyl, tetrahydropyranyl, acetylpiperidinyl and tert-butoxycarbonylpiperidinyl.

Suitably, $R^c$ represents hydrogen or $C_{1-6}$ alkyl. In one embodiment, $R^c$ is hydrogen. In another embodiment, $R^c$ represents $C_{1-6}$ alkyl, especially methyl or ethyl, particularly methyl. In a further embodiment, $R^c$ represents $C_{3-7}$ cycloalkyl, e.g. cyclopropyl, cyclobutyl, cyclopentyl or cyclohexyl.

Alternatively, the moiety —$NR^bR^c$ may suitably represent azetidin-1-yl, pyrrolidin-1-yl, oxazolidin-3-yl, isoxazolidin-2-yl, thiazolidin-3-yl, isothiazolidin-2-yl, piperidin-1-yl, morpholin-4-yl, thiomorpholin-4-yl, piperazin-1-yl, homopiperidin-1-yl, homomorpholin-4-yl or homopiperazin-1-yl, any of which groups may be optionally substituted by one or more substituents.

Selected examples of suitable substituents on the heterocyclic moiety —$NR^bR^c$ include $C_{1-6}$ alkyl, $C_{1-6}$ alkylsulphonyl, hydroxy, hydroxy$(C_{1-6})$alkyl, amino$(C_{1-6})$alkyl, cyano, oxo, $C_{2-6}$ alkylcarbonyl, carboxy, $C_{2-6}$ alkoxycarbonyl, amino, $C_{2-6}$ alkylcarbonylamino, $C_{2-6}$ alkylcarbonylamino$(C_{1-6})$alkyl, $C_{2-6}$ alkoxycarbonylamino, $C_{1-6}$ alkylsulphonylamino and aminocarbonyl.

Selected examples of specific substituents on the heterocyclic moiety —$NR^bR^c$ include methyl, methylsulphonyl, hydroxy, hydroxymethyl, aminomethyl, cyano, oxo, acetyl, carboxy, ethoxycarbonyl, amino, acetylamino, acetylaminomethyl, tert-butoxycarbonylamino, methylsulphonylamino and aminocarbonyl.

Specific values of the moiety —$NR^bR^c$ include azetidin-1-yl, hydroxyazetidin-1-yl, hydroxymethylazetidin-1-yl, (hydroxy)(hydroxymethyl)azetidin-1-yl, aminomethylazetidin-1-yl, cyanoazetidin-1-yl, carboxyazetidin-1-yl, amino azetidin-1-yl, aminocarbonylazetidin-1-yl, pyrrolidin-1-yl, aminomethylpyrrolidin-1-yl, oxopyrrolidin-1-yl, acetylaminomethylpyrrolidin-1-yl, tert-butoxycarbonylaminopyrrolidin-1-yl, oxo-oxazolidin-3-yl, hydroxyisoxazolidin-2-yl, thiazolidin-3-yl, oxothiazolidin-3-yl, dioxo-isothiazolidin-2-yl, piperidin-1-yl, hydroxypiperidin-1-yl, hydroxymethylpiperidin-1-yl, aminopiperidin-1-yl, acetylaminopiperidin-1-yl, tert-butoxycarbonylaminopiperidin-1-yl, methylsulphonylaminopiperidin-1-yl, morpholin-4-yl, piperazin-1-yl, methylpiperazin-1-yl, methylsulphonylpiperazin-1-yl, oxopiperazin-1-yl, acetylpiperazin-1-yl, ethoxycarbonylpiperazin-1-yl and oxohomopiperazin-1-yl.

Suitably, $R^d$ represents hydrogen; or $C_{1-6}$ alkyl, aryl or heteroaryl, any of which groups may be optionally substituted by one or more substituents.

Selected examples of suitable values for $R^d$ include hydrogen, methyl, ethyl, isopropyl, 2-methylpropyl, tert-butyl, cyclopropyl, cyclobutyl, phenyl, thiazolidinyl, thienyl, imidazolyl and thiazolyl, any of which groups may be optionally substituted by one or more substituents.

Selected examples of suitable substituents on $R^d$ include halogen, $C_{1-6}$ alkyl, $C_{1-6}$ alkoxy, oxo, $C_{2-6}$ alkylcarbonyloxy and di$(C_{1-6})$alkylamino.

Selected examples of particular substituents on $R^d$ include fluoro, methyl, methoxy, oxo, acetoxy and dimethylamino.

In one embodiment, $R^d$ represents hydrogen. In another embodiment, $R^d$ represents optionally substituted $C_{1-6}$ alkyl. In one aspect of that embodiment, $R^d$ ideally represents unsubstituted $C_{1-6}$ alkyl, e.g. methyl, ethyl, isopropyl, 2-methylpropyl or tert-butyl, especially methyl. In another aspect of that embodiment, $R^d$ ideally represents substituted $C_{1-6}$ alkyl, e.g. substituted methyl or substituted ethyl, including acetoxymethyl, dimethylaminomethyl and trifluoroethyl. In another embodiment, $R^d$ represents optionally substituted aryl. In one aspect of that embodiment, $R^d$ represents unsubstituted aryl, especially phenyl. In another aspect of that embodiment, $R^d$ represents monosubstituted aryl, especially methylphenyl. In a further aspect of that embodiment, $R^d$ represents disubstituted aryl, e.g. dimethoxyphenyl. In a further embodiment, $R^d$ represents optionally substituted heteroaryl, e.g. thienyl, chlorothienyl, methylthienyl, methylimidazolyl or thiazolyl. In another embodiment, $R^d$ represents optionally substituted $C_{3-7}$ cycloalkyl, e.g. cyclopropyl or cyclobutyl. In a further embodiment, $R^d$ represents optionally substituted $C_{3-7}$ heterocycloalkyl, e.g. thiazolidinyl or oxothiazolidinyl.

Selected examples of specific values for $R^d$ include hydrogen, methyl, acetoxymethyl, dimethylaminomethyl, ethyl, trifluoroethyl, isopropyl, 2-methylpropyl, tert-butyl, cyclopropyl, cyclobutyl, phenyl, dimethoxyphenyl, thiazolidinyl, oxothiazolidinyl, thienyl, chlorothienyl, methylthienyl, methylimidazolyl and thiazolyl.

Suitably, $R^e$ represents $C_{1-6}$ alkyl or aryl, either of which groups may be optionally substituted by one or more substituents.

Selected examples of suitable substituents on $R^e$ include $C_{1-6}$ alkyl, especially methyl.

In one embodiment, R$^e$ represents optionally substituted C$_{1-6}$ alkyl, ideally unsubstituted C$_{1-6}$ alkyl, e.g. methyl or propyl, especially methyl. In another embodiment, R$^e$ represents optionally substituted aryl. In one aspect of that embodiment, R$^e$ represents unsubstituted aryl, especially phenyl. In another aspect of that embodiment, R$^e$ represents monosubstituted aryl, especially methylphenyl. In a further embodiment, R$^e$ represents optionally substituted heteroaryl.

Selected values of R$^e$ include methyl, propyl and methylphenyl.

One sub-group of the compounds of formula (IB) above is represented by the compounds of formula (IIA) and N-oxides thereof, and pharmaceutically acceptable salts thereof:

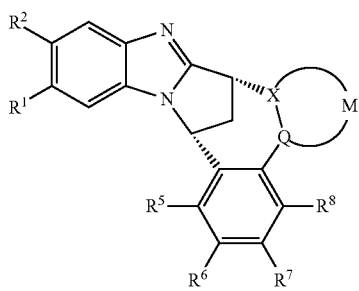

(IIA)

wherein —(X-M-Q)-, R$^1$, R$^2$, R$^5$, R$^6$, R$^7$ and R$^8$ are as defined above.

A particular subset of the compounds of formula (IIA) above is represented by the compounds of formula (IIA-1) and N-oxides thereof, and pharmaceutically acceptable salts thereof:

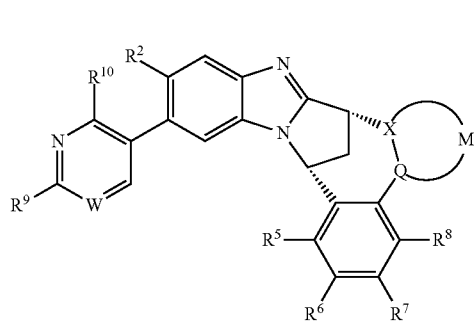

(IIA-1)

wherein
W represents N, CH or CF;
R$^9$ represents hydroxy(C$_{1-6}$)alkyl or amino(C$_{1-6}$)alkyl;
R$^{10}$ represents hydrogen or C$_{1-6}$ alkyl; and
—(X-M-Q)-, R$^2$, R$^5$, R$^6$, R$^7$ and R$^8$ are as defined above.
Generally, W represents N or CH.
Suitably, W represents N or CF.
In one embodiment, W represents N. In another embodiment, W represents CH. In a further embodiment, W represents CF.

Typically, R$^9$ represents hydroxyisopropyl or aminoisopropyl.

Typical values of R$^9$ include 2-hydroxyprop-2-yl and 2-aminoprop-2-yl.

In one embodiment, R$^9$ represents hydroxy(C$_{1-6}$)alkyl. In a particular aspect of that embodiment, R$^9$ represents hydroxyisopropyl, especially 2-hydroxyprop-2-yl.

In another embodiment, R$^9$ represents amino(C$_{1-6}$)alkyl. In a particular aspect of that embodiment, R$^9$ represents aminoisopropyl, especially 2-aminoprop-2-yl.

Typically, R$^{10}$ represents hydrogen or methyl.

In one embodiment, R$^{10}$ represents hydrogen. In another embodiment, R$^{10}$ represents C$_{1-6}$ alkyl. In one aspect of that embodiment, R$^{10}$ represents methyl.

Another subset of the compounds of formula (IIA) above is represented by the compounds of formula (IIA-2) and N-oxides thereof, and pharmaceutically acceptable salts thereof:

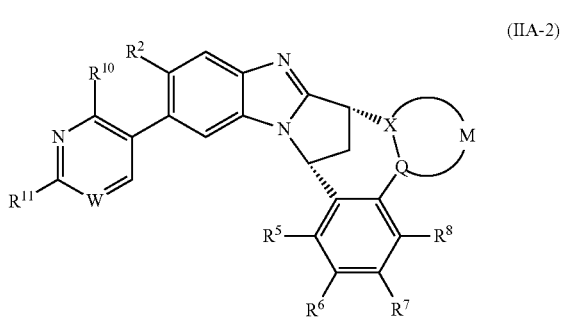

(IIA-2)

wherein
R$^{11}$ represents a group of formula (a), (b), (c), (d), (e), (f) or (g):

(a)

(b)

(c)

(d)

(e)

(f)

-continued

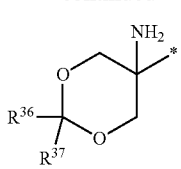

(g)

in which the asterisk (*) represents the site of attachment to the remainder of the molecule;

U represents O, S, S(O), S(O)$_2$, S(O)(NR$^b$), N(R$^{31}$) or C(R$^{32}$)(R$^{33}$);

R$^{31}$ represents hydrogen, cyano(C$_{1-6}$)alkyl, C$_{1-6}$ alkyl, trifluoromethyl, trifluoroethyl, C$_{1-6}$ alkylsulphonyl, (C$_{1-6}$) alkylsulphonyl(C$_{1-6}$)alkyl, formyl, C$_{2-6}$ alkylcarbonyl, carboxy, carboxy(C$_{1-6}$)alkyl, C$_{2-6}$ alkoxycarbonyl, C$_{2-6}$ alkoxycarbonyl(C$_{1-6}$)alkyl, tetrazolyl(C$_{1-6}$)alkyl, aminocarbonyl, C$_{1-6}$ alkylaminocarbonyl, di(C$_{1-6}$)alkylaminocarbonyl, aminosulphonyl, C$_{1-6}$ alkylaminosulphonyl or di(C$_{1-6}$)alkylaminosulphonyl;

R$^{32}$ represents hydrogen, halogen, cyano, hydroxy, hydroxy(C$_{1-6}$)alkyl, C$_{1-6}$ alkylsulphonyl, formyl, carboxy, carboxy(C$_{1-6}$)alkyl, C$_{2-6}$ alkoxycarbonyl, C$_{2-6}$ alkoxycarbonyl(C$_{1-6}$)alkyl, aminosulphonyl, (C$_{1-6}$)alkylsulphoximinyl, [(C$_{1-6}$)alkyl][N—(C$_{1-6}$)alkyl]sulphoximinyl, (C$_{1-6}$)alkylsulphonylaminocarbonyl, (C$_{2-6}$)alkylcarbonylaminosulphonyl, (C$_{1-6}$)alkoxyaminocarbonyl, tetrazolyl or hydroxyoxadiazolyl;

R$^{33}$ represents hydrogen, halogen, C$_{1-6}$ alkyl, difluoromethyl, trifluoromethyl, hydroxy, hydroxy(C$_{1-6}$)alkyl, C$_{1-6}$ alkoxy, amino or carboxy;

R$^{34}$ represents hydrogen, halogen, halo(C$_{1-6}$)alkyl, hydroxy, C$_{1-6}$ alkoxy, C$_{1-6}$ alkylthio, C$_{1-6}$ alkylsulphinyl, C$_{1-6}$ alkylsulphonyl, amino, C$_{1-6}$ alkylamino, di(C$_{1-6}$)alkylamino, (C$_{2-6}$)alkylcarbonylamino, (C$_{2-6}$)alkylcarbonylamino(C$_{1-6}$)alkyl, (C$_{1-6}$)alkylsulphonylamino or (C$_{1-6}$)alkylsulphonylamino(C$_{1-6}$)alkyl;

R$^{35}$ represents hydrogen or C$_{1-6}$ alkyl;

R$^{36}$ and R$^{37}$ independently represent C$_{1-6}$ alkyl; or

R$^{36}$ and R$^{37}$, when taken together with the carbon atom to which they are both attached, represent C$_{3-7}$ cycloalkyl; and —(X-M-Q)-, W, R$^2$, R$^5$, R$^6$, R$^7$, R$^8$, R$^{10}$ and R$^b$ are as defined above.

Generally, U represents O, S(O)$_2$, N(R$^{31}$) or C(R$^{32}$)(R$^{33}$).

Typically, U represents O, N(R$^{31}$) or C(R$^{32}$)(R$^{33}$).

In a first embodiment, U represents O. In a second embodiment, U represents S. In a third embodiment, U represents S(O). In a fourth embodiment, U represents S(O)$_2$. In a fifth embodiment, U represents S(O)(NR$^b$). In a sixth embodiment, U represents N(R$^{31}$). In a seventh embodiment, U represents C(R$^{32}$)(R$^{33}$).

Typical values of R$^{31}$ include hydrogen, cyanoethyl, methyl, ethyl, isopropyl, trifluoromethyl, trifluoroethyl, methylsulphonyl, methylsulphonylethyl, formyl, acetyl, carboxy, carboxymethyl, carboxyethyl, methoxycarbonyl, ethoxycarbonyl, tert-butoxycarbonyl, ethoxycarbonylmethyl, ethoxycarbonylethyl, tetrazolylmethyl, aminocarbonyl, methylaminocarbonyl, dimethylaminocarbonyl, aminosulphonyl, methylaminosulphonyl and dimethylaminosulphonyl.

Suitably, R$^{31}$ represents hydrogen or C$_{1-6}$ alkyl.

Suitable values of R$^{31}$ include hydrogen and methyl.

In a first embodiment, R$^{31}$ represents hydrogen. In a second embodiment, R$^{31}$ represents C$_{1-6}$ alkyl, especially methyl.

Typical values of R$^{32}$ include hydrogen, fluoro, cyano, hydroxy, hydroxymethyl, methylsulphonyl, formyl, carboxy, carboxymethyl, carboxyethyl, methoxycarbonyl, ethoxycarbonyl, tert-butoxycarbonyl, methoxycarbonylmethyl, methoxycarbonylethyl, ethoxycarbonylmethyl, ethoxycarbonylethyl, aminosulphonyl, methylsulphoximinyl, (methyl)(N-methyl)sulphoximinyl, methylsulphonylaminocarbonyl, acetylaminosulphonyl, methoxyaminocarbonyl, tetrazolyl and hydroxyoxadiazolyl.

Suitably, R$^{32}$ represents hydrogen, halogen or cyano.

Suitable values of R$^{32}$ include hydrogen, fluoro and cyano.

In a first embodiment, R$^{32}$ represents hydrogen. In a second embodiment, R$^{32}$ represents halogen, especially fluoro. In a third embodiment, R$^{32}$ represents cyano.

Generally, R$^{33}$ represents hydrogen, halogen, C$_{1-6}$ alkyl, difluoromethyl or trifluoromethyl.

Typical values of R$^{33}$ include hydrogen, fluoro, methyl, ethyl, isopropyl, difluoromethyl, trifluoromethyl, hydroxy, hydroxymethyl, methoxy, amino and carboxy.

Suitably, R$^{33}$ represents hydrogen, halogen or difluoromethyl.

Suitable values of R$^{33}$ include hydrogen, fluoro and difluoromethyl.

In a first embodiment, R$^{33}$ represents hydrogen. In a second embodiment, R$^{33}$ represents halogen. In one aspect of that embodiment, R$^{33}$ represents fluoro. In a third embodiment, R$^{33}$ represents C$_{1-6}$ alkyl. In a first aspect of that embodiment, R$^{33}$ represents methyl. In a second aspect of that embodiment, R$^{33}$ represents ethyl. In a third aspect of that embodiment, R$^{33}$ represents isopropyl. In a fourth embodiment, R$^{33}$ represents difluoromethyl. In a fifth embodiment, R$^{33}$ represents trifluoromethyl. In a sixth embodiment, R$^{33}$ represents hydroxy. In a seventh embodiment, R$^{33}$ represents hydroxy(C$_{1-6}$)alkyl. In one aspect of that embodiment, R$^{33}$ represents hydroxymethyl. In an eighth embodiment, R$^{33}$ represents C$_{1-6}$ alkoxy. In one aspect of that embodiment, R$^{33}$ represents methoxy. In a ninth embodiment, R$^{33}$ represents amino. In a tenth embodiment, R$^{33}$ represents carboxy.

In a first embodiment, R$^{34}$ represents hydrogen. In a second embodiment, R$^{34}$ represents halogen. In one aspect of that embodiment, R$^{34}$ represents fluoro. In a third embodiment, R$^{34}$ represents halo(C$_{1-6}$)alkyl. In one aspect of that embodiment, R$^{34}$ represents fluoromethyl. In a fourth embodiment, R$^{34}$ represents hydroxy. In a fifth embodiment, R$^{34}$ represents C$_{1-6}$ alkoxy, especially methoxy. In a sixth embodiment, R$^{34}$ represents C$_{1-6}$ alkylthio, especially methylthio. In a seventh embodiment, R$^{34}$ represents C$_{1-6}$ alkylsulphinyl, especially methylsulphinyl. In an eighth embodiment, R$^{34}$ represents C$_{1-6}$ alkylsulphonyl, especially methylsulphonyl. In a ninth embodiment, R$^{34}$ represents amino. In a tenth embodiment, R$^{34}$ represents C$_{1-6}$ alkylamino, especially methylamino. In an eleventh embodiment, R$^{34}$ represents di(C$_{1-6}$)alkylamino, especially dimethylamino. In a twelfth embodiment, R$^{34}$ represents (C$_{2-6}$)alkylcarbonylamino, especially acetylamino. In a thirteenth embodiment, R$^{34}$ represents (C$_{2-6}$)alkylcarbonylamino(C$_{1-6}$)alkyl, especially acetylaminomethyl. In a fourteenth embodiment, R$^{34}$ represents (C$_{1-6}$)alkylsulphonylamino, especially methylsulphonylamino. In a fifteenth embodiment, R$^{34}$ represents (C$_{1-6}$)alkylsulphonylamino(C$_{1-6}$)alkyl, especially methylsulphonylaminomethyl.

Suitably, R$^{34}$ represents hydrogen or amino.

Suitable values of R$^{35}$ include hydrogen and methyl.

In a first embodiment, $R^{35}$ represents hydrogen. In a second embodiment, $R^{35}$ represents $C_{1-6}$ alkyl, especially methyl.

Suitably, $R^{36}$ represents methyl or ethyl, especially methyl.

Suitably, $R^{37}$ represents methyl or ethyl, especially methyl.

Alternatively, $R^{36}$ and $R^{37}$, when taken together with the carbon atom to which they are both attached, may suitably represent cyclopropyl, cyclobutyl, cyclopentyl, cyclohexyl or cycloheptyl.

Specific novel compounds in accordance with the present invention include each of the compounds whose preparation is described in the accompanying Examples, and pharmaceutically acceptable salts thereof.

The compounds in accordance with the present invention are beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, psoriatic arthropathy, vasculitis, inflammatory myopathy (including polymyositis, dermatomyositis and inclusion body myositis), scleroderma, multiple sclerosis, systemic sclerosis, ankylosing spondylitis, rheumatoid arthritis, non-specific inflammatory arthritis, juvenile inflammatory arthritis, juvenile idiopathic arthritis (including oligoarticular and polyarticular forms thereof), anaemia of chronic disease (ACD), Still's disease (juvenile and/or adult onset), Behçet's disease and Sjögren's syndrome. Autoimmune endocrine disorders include thyroiditis. Organ-specific autoimmune disorders include Addison's disease, haemolytic or pernicious anaemia, acute kidney injury (AKI; including cisplatin-induced AKI), diabetic nephropathy (DN), obstructive uropathy (including cisplatin-induced obstructive uropathy), glomerulonephritis (including Goodpasture's syndrome, immune complex-mediated glomerulonephritis and antineutrophil cytoplasmic antibodies (ANCA)-associated glomerulonephritis), lupus nephritis (LN), minimal change disease, Graves' disease, idiopathic thrombocytopenic purpura, inflammatory bowel disease (including Crohn's disease, ulcerative colitis, indeterminate colitis and pouchitis), pemphigus, atopic dermatitis, autoimmune hepatitis, primary biliary cirrhosis, autoimmune pneumonitis, autoimmune carditis, myasthenia gravis, spontaneous infertility, osteoporosis, osteopenia, erosive bone disease, chondritis, cartilage degeneration and/or destruction, fibrosing disorders (including various forms of hepatic and pulmonary fibrosis), asthma, rhinitis, chronic obstructive pulmonary disease (COPD), respiratory distress syndrome, sepsis, fever, muscular dystrophy (including Duchenne muscular dystrophy), organ transplant rejection (including kidney allograft rejection), scleritis (including giant cell arteritis scleritis), Takayasu arteritis, hidradenitis suppurativa, pyoderma gangrenosum, sarcoidosis, polymyalgia rheumatic and axial spondyloarthritis.

Neurological and neurodegenerative disorders include Alzheimer's disease, Parkinson's disease, Huntington's disease, ischaemia, stroke, amyotrophic lateral sclerosis, spinal cord injury, head trauma, seizures and epilepsy.

Cardiovascular disorders include thrombosis, cardiac hypertrophy, hypertension, irregular contractility of the heart (e.g. during heart failure), and sexual disorders (including erectile dysfunction and female sexual dysfunction). Modulators of TNFα function may also be of use in the treatment and/or prevention of myocardial infarction (see J. J. Wu et al., *JAMA*, 2013, 309, 2043-2044).

Metabolic disorders include diabetes (including insulin-dependent diabetes mellitus and juvenile diabetes), dyslipidemia and metabolic syndrome.

Ocular disorders include retinopathy (including diabetic retinopathy, proliferative retinopathy, non-proliferative retinopathy and retinopathy of prematurity), macular oedema (including diabetic macular oedema), age-related macular degeneration (ARMD), vascularisation (including corneal vascularisation and neovascularisation), retinal vein occlusion, and various forms of uveitis (including iritis) and keratitis Oncological disorders, which may be acute or chronic, include proliferative disorders, especially cancer, and cancer-associated complications (including skeletal complications, cachexia and anaemia). Particular categories of cancer include haematological malignancy (including leukaemia and lymphoma) and non-haematological malignancy (including solid tumour cancer, sarcoma, meningioma, glioblastoma multiforme, neuroblastoma, melanoma, gastric carcinoma and renal cell carcinoma). Chronic leukaemia may be myeloid or lymphoid. Varieties of leukaemia include lymphoblastic T cell leukaemia, chronic myelogenous leukaemia (CML), chronic lymphocytic/lymphoid leukaemia (CLL), hairy-cell leukaemia, acute lymphoblastic leukaemia (ALL), acute myelogenous leukaemia (AML), myelodysplastic syndrome, chronic neutrophilic leukaemia, acute lymphoblastic T cell leukaemia, plasmacytoma, immunoblastic large cell leukaemia, mantle cell leukaemia, multiple myeloma, acute megakaryoblastic leukaemia, acute megakaryocytic leukaemia, promyelocytic leukaemia and erythroleukaemia. Varieties of lymphoma include malignant lymphoma, Hodgkin's lymphoma, non-Hodgkin's lymphoma, lymphoblastic T cell lymphoma, Burkitt's lymphoma, follicular lymphoma, MALT1 lymphoma and marginal zone lymphoma. Varieties of non-haematological malignancy include cancer of the prostate, lung, breast, rectum, colon, lymph node, bladder, kidney, pancreas, liver, ovary, uterus, cervix, brain, skin, bone, stomach and muscle. Modulators of TNFα function may also be used to increase the safety of the potent anticancer effect of TNF (see F. V. Hauwermeiren et al., *J. Clin. Invest.*, 2013, 123, 2590-2603).

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

If desired, a compound in accordance with the present invention may be co-administered with another pharmaceutically active agent, e.g. an anti-inflammatory molecule.

The compounds of formula (I) above wherein the moiety —(X-M-Q)— represents a group of formula (Ma) or (Mb) as defined above, in which $R^{2m}$ is hydrogen, may be prepared by a process which comprises the intramolecular cyclization of a compound of formula (III):

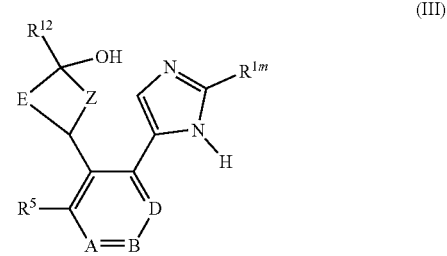

(III)

wherein A, B, D, Z, E, $R^5$, $R^{12}$ and $R^{1m}$ are as defined above.

The cyclization is suitably effected by treating compound (III) with triphenylphosphine and diisopropyl azodicarboxylate. The reaction may be conveniently carried out at ambient temperature in a suitable solvent, e.g. a cyclic ether such as tetrahydrofuran.

The intermediates of formula (III) may be prepared by reacting a compound of formula (IV) with a compound of formula (V):

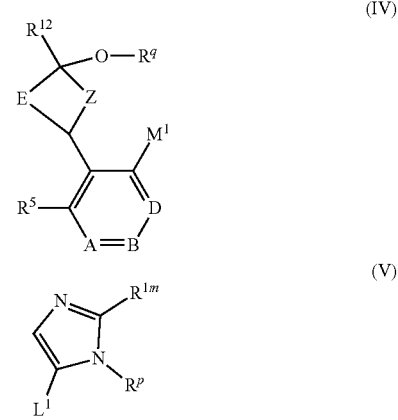

(IV)

(V)

wherein A, B, D, Z, E, $R^5$, $R^{12}$ and $R^{1m}$ are as defined above, $L^1$ represents a suitable leaving group, $M^1$ represents a boronic acid moiety —B(OH)$_2$ or a cyclic ester thereof formed with an organic diol, e.g. pinacol, 1,3-propanediol or neopentyl glycol, R$^p$ represents hydrogen or an N-protecting group, and R$^q$ represents hydrogen or an O-protecting group; in the presence of a transition metal catalyst; followed, as necessary, by removal of the N-protecting group R$^p$; and followed, as necessary, by removal of the O-protecting group R$^q$.

The leaving group L$^1$ suitably represents halogen, e.g. bromo.

The N-protecting group R$^p$ suitably represents tert-butoxycarbonyl (BOC).

The O-protecting group R$^q$ is suitably a tri(C$_{1-4}$)alkylsilyl moiety, e.g. tert-butyl(dimethyl)silyl.

The transition metal catalyst of use in the reaction between compounds (IV) and (V) may suitably be a palladium catalyst such as [1,1'-bis(diphenylphosphino)ferrocene]-dichloropalladium(II). The reaction is conveniently effected at an elevated temperature in the presence of a base, e.g. an alkali metal carbonate such as cesium carbonate, in a suitable organic solvent, e.g. a cyclic ether such as 1,4-dioxane, and water.

Where the N-protecting group R$^p$ is BOC, the subsequent removal thereof may conveniently be effected by treatment with a fluoride salt, e.g. an alkali metal fluoride such as cesium fluoride.

Where the O-protecting group R$^q$ is tert-butyl(dimethyl)silyl, the subsequent removal thereof may conveniently be effected by treatment with a fluoride salt, e.g. a tetra(C$_{1-4}$) alkylammonium fluoride such as tetra-n-butylammonium fluoride. Alternatively, the removal of a tert-butyl(dimethyl)silyl group may conveniently be effected by treatment with p-toluenesulfonic acid.

The intermediates of formula (IV) wherein M$^1$ represents a cyclic ester of a boronic acid moiety formed with pinacol may be prepared by reacting a compound of formula (VI):

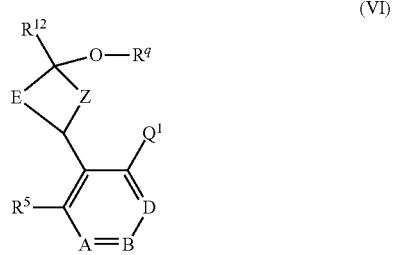

(VI)

wherein A, B, D, Z, E, R$^5$, R$^{12}$ and R$^q$ are as defined above, and Q$^1$ represents halogen; with bis(pinacolato)diboron in the presence of a transition metal catalyst.

Suitably, Q$^1$ represents chloro or bromo.

The transition metal catalyst of use in the above reaction may suitably be a palladium catalyst such as [1,1'-bis(diphenylphosphino)ferrocene]dichloropalladium(II). The reaction is conveniently effected at an elevated temperature in the presence of potassium acetate, in a suitable organic solvent, e.g. a cyclic ether such as 1,4-dioxane.

The intermediates of formula (VI) wherein R$^q$ represents tert-butyl(dimethyl)silyl may be prepared from the corresponding compound of formula (VI) wherein R$^q$ represents hydrogen by treatment with tert-butyl(dimethyl)chlorosilane, typically in the presence of imidazole. The reaction is conveniently effected at ambient temperature in a suitable organic solvent, e.g. a dipolar aprotic solvent such as N,N-dimethylformamide.

The compounds of formula (I) above wherein the moiety —(X-M-Q)- represents a group of formula (Mc) as defined above may be prepared by a process which comprises reacting a compound of formula (VII) with a compound of formula (VIII):

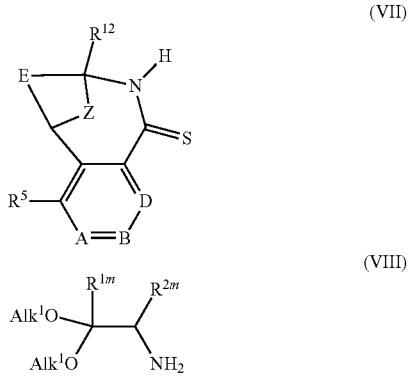

wherein A, B, D, Z, E, R$^5$, R$^{12}$, R$^{1m}$ and R$^{2m}$ are as defined above, and Alk$^1$ represents C$_{1-4}$ alkyl, e.g. ethyl.

The transformation is suitably accomplished by treating the reagents with a catalytic quantity of p-toluenesulfonic acid. The reaction is conveniently effected at an elevated temperature in a suitable organic solvent, e.g. a C$_{1-4}$ alkanol such as n-butanol.

The compounds of formula (I) above wherein the moiety —(X-M-Q)- represents a group of formula (Me) as defined above may be prepared by a process which comprises reacting a compound of formula (VII) as defined above with a compound of formula R$^{1m}$—C(O)N(H)NH$_2$, wherein R$^{1m}$ is as defined above.

The transformation is suitably accomplished in the presence of 4 Å molecular sieve. The reaction is conveniently effected at an elevated temperature in a suitable organic solvent, e.g. a C$_{1-4}$ alkanol such as n-butanol.

The intermediates of formula (VII) above may be prepared by reacting a compound of formula (IX):

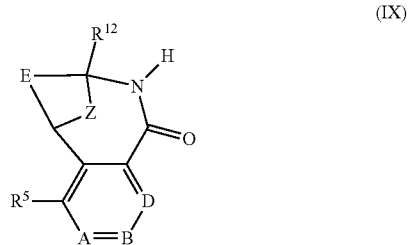

(IX)

wherein A, B, D, Z, E, R$^5$ and R$^{12}$ are as defined above; with 2,4-bis(4-methoxyphenyl)-1,3,2,4-dithiadiphosphetane-2,4-dithione (Lawesson's reagent).

The reaction is conveniently effected at an elevated temperature in a suitable organic solvent, e.g. a hydrocarbon solvent such as toluene.

The intermediates of formula (IX) above may be prepared by the intramolecular cyclization of a compound of formula (X):

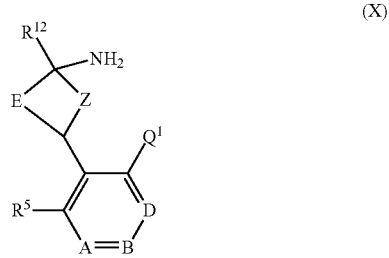

(X)

wherein A, B, D, Z, E, R$^5$, R$^{12}$ and Q$^1$ are as defined above; in the presence of carbon monoxide and a transition metal catalyst.

The cyclization is generally effected at an elevated temperature under an elevated pressure of carbon monoxide. The reaction is conveniently carried out in a suitable solvent, e.g. 1,4-dioxane, dimethyl sulfoxide or N,N-dimethylacetamide.

Moreover, the cyclization will generally be performed in the presence of a base, e.g. an inorganic base such as sodium carbonate or potassium carbonate, and/or by activation using molecular sieves.

The transition metal catalyst of use in the above reaction is suitably selected from dichloro[1,3-bis(dicyclohexylphosphino)propane]palladium(II), dichloro[9,9-dimethyl-4,5-bis(diphenylphosphino)xanthene]palladium(II) and 2,2-dichloro-1,1,3,3-tetra-cyclohexyl-1λ$^5$,3λ$^5$-palladocyclohexane. Alternatively, a solution of palladium (II) acetate and 4,5-bis(diphenylphosphino)-9,9-dimethylxanthene (Xantphos) in a suitable solvent may be used.

In a variant procedure, the reaction may be performed using molybdenum hexacarbonyl as an alternative source of carbon monoxide.

The intermediates of formula (X) may be prepared from the intermediates of formula (VI) above, wherein R$^q$ represents hydrogen, by a two-step procedure which comprises: (i) reaction with diphenyl phosphoryl azide; and (ii) reaction of the compound thereby obtained with trimethylphosphine.

Step (i) of the above procedure is suitably accomplished under basic conditions, e.g. in the presence of an organic base such as 1,8-diazabicyclo[5.4.0]undec-7-ene (DBU).

The reaction is conveniently effected at an elevated temperature in a suitable organic solvent, e.g. a hydrocarbon solvent such as toluene.

Step (ii) of the above procedure is conveniently effected at ambient temperature in a suitable organic solvent, e.g. a mixture of tetrahydrofuran and toluene, and water.

The compounds of formula (I) above wherein the moiety —(X-M-Q)— represents a group of formula (Md) as defined above may be prepared by a process which comprises the intramolecular cyclisation of a compound of formula (XI):

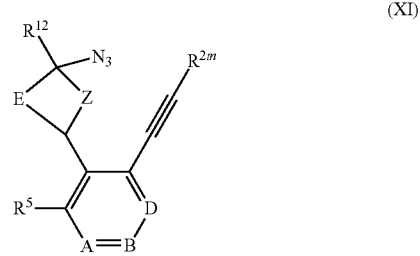

(XI)

wherein A, B, D, Z, E, R$^5$, R$^{12}$ and R$^{2m}$ are as defined above.

The cyclisation is suitably effected by treating compound (XI) with a copper(I) salt, e.g. a copper(I) halide such as copper(I) iodide. The reaction may be conveniently carried out at an elevated temperature in a suitable solvent, e.g. a cyclic ether such as 1,4-dioxane.

The intermediates of formula (XI) above may be prepared by reacting a compound of formula (XII):

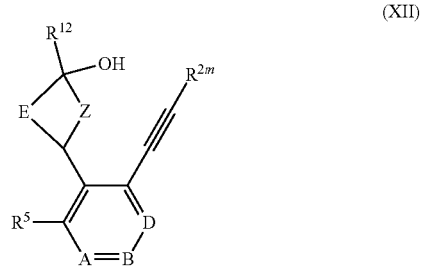

(XII)

wherein A, B, D, Z, E, R$^5$, R$^{12}$ and R$^{2m}$ are as defined above; with diphenyl phosphoryl azide.

The transformation is suitably accomplished under basic conditions, e.g. in the presence of an organic base such as 1,8-diazabicyclo[5.4.0]undec-7-ene (DBU). The reaction is conveniently effected at an elevated temperature in a suitable organic solvent, e.g. a cyclic ether such as tetrahydrofuran.

The intermediates of formula (XII) above may be prepared from the intermediates of formula (VI) as defined above by a multi-step procedure which comprises:

(i) reaction of compound (VI) with potassium vinyltrifluoroborate in the presence of a transition metal catalyst to provide a compound corresponding to formula (VI) wherein Q$^1$ represents —CH═CH$_2$;

(ii) reaction of the compound thereby obtained with osmium tetroxide and sodium periodate to provide a compound corresponding to formula (VI) wherein Q$^1$ represents —CH═O;

(iii) reaction of the compound thereby obtained with dimethyl (1-diazo-2-oxo-propyl)phosphonate; and (iv) where necessary, removal of the O-protecting group R$^q$ by standard methodology well known to the person skilled in the art.

The transition metal catalyst of use in step (i) of the above procedure may suitably be a palladium catalyst such as [1,1′-bis(diphenylphosphino)ferrocene]palladium(II) dichloride dichloromethane complex. The reaction is conveniently effected at an elevated temperature in the presence of a base, e.g. an alkali metal carbonate such as cesium carbonate, in a suitable organic solvent, e.g. a cyclic ether such as 1,4-dioxane, and water.

Step (ii) of the above procedure may conveniently be effected at ambient temperature in a suitable organic solvent, e.g. a cyclic ether such as 1,4-dioxane, and water.

Step (iii) of the above procedure will suitably be performed in the presence of a base, e.g. an alkali metal carbonate such as potassium carbonate. The reaction may conveniently be carried out at ambient temperature in a suitable organic solvent, e.g. a C$_{1-4}$ alkanol such as methanol.

The intermediates of formula (VI) wherein E represents a group of formula (Ea) as defined above, and R$^{12}$ and R$^q$ both represent hydrogen, may be prepared by a process which comprises the intramolecular cyclization and desilylation of an intermediate of formula (XIII):

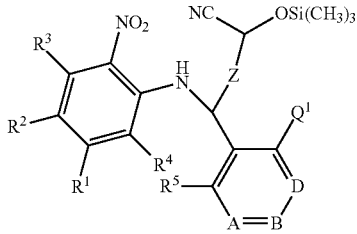

(XIII)

wherein A, B, D, Z, $R^1$, $R^2$, $R^3$, $R^4$, $R^5$ and $Q^1$ are as defined above.

The reaction is suitably performed in the presence of tin(II) chloride at an elevated temperature in a polar solvent, e.g. ethanol.

The intermediates of formula (XIII) as defined above may be prepared by reacting intermediate (XIV):

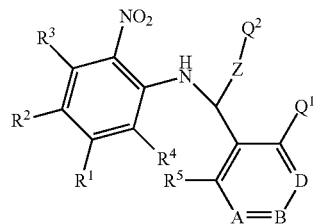

(XIV)

wherein $Q^2$ represents —C(O)—H, and A, B, D, Z, $R^1$, $R^2$, $R^3$, $R^4$, $R^5$ and $Q^1$ are as defined above; with zinc iodide and trimethylsilyl cyanide in the presence of a base, e.g. triethylamine.

Typically, the intermediate of formula (XIV) wherein $Q^2$ represents —C(O)—H may be prepared from the corresponding compound wherein $Q^2$ represents —$CO_2R^h$, in which $R^h$ represents $C_{1-6}$ alkyl, e.g. methyl or ethyl, by reduction with a conventional reducing agent, e.g. a metal hydride such as diisobutylaluminium hydride (DIBAL-H).

The intermediates of formula (XIV) wherein $Q^2$ represents —$CO_2R^h$ may be obtained by reacting an intermediate of formula (XV) with an intermediate of formula (XVI):

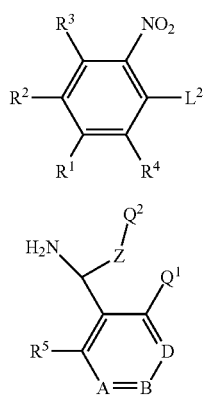

(XV)

(XVI)

wherein A, B, D, Z, $R^1$, $R^2$, $R^3$, $R^4$, $R^5$, $Q^1$ and $Q^2$ are as defined above, and $L^2$ represents a suitable leaving group.

The leaving group $L^2$ is suitably a halogen atom, for example fluorine or bromine.

The reaction is conveniently performed in the presence of a base, e.g. an inorganic base such as potassium carbonate, in a suitable solvent, e.g. an apolar solvent such as acetonitrile, at an elevated temperature.

The intermediates of formula (XVI) may be prepared by a multi-step process starting from an intermediate of formula (XVII):

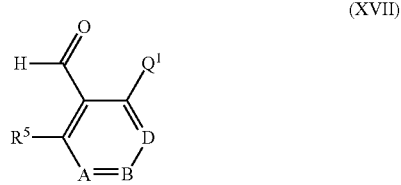

(XVII)

wherein A, B, D, $R^5$ and $Q^1$ are as defined above; which process comprises the following steps:

(i) reaction of intermediate (XVII) with (S)-tert-butylsulfinamide in the presence of $K_3PO_4/K_2HPO_4$ in a suitable solvent, e.g. tetrahydrofuran;

(ii) reacting the compound obtained from step (i) with a compound of formula $L^3$-Z-$Q^2$, wherein Z and $Q^2$ are as defined above and $L^3$ is a suitable leaving group, e.g. halogen, such as bromine, and activated zinc metal dust prepared according to conditions described by H. Hilpert et al. in *Journal of Medicinal Chemistry*, 2013, 56(10), 3980-3995, typically in the presence of a transition metal salt, e.g. copper(I) chloride, optionally at an elevated temperature; and (iii) reaction with a strong mineral acid, e.g. hydrochloric acid.

The intermediates of formula (XVII) wherein $R^5$ represents hydroxy may be transformed into the corresponding intermediate of formula (XVII) wherein $R^5$ represents difluoromethoxy by reaction with diethyl (bromodifluoromethyl)phosphonate at low temperature.

Alternatively, the intermediates of formula (XVII) wherein $R^5$ represents halogen, e.g. chloro, may be transformed into the corresponding intermediate of formula (XVII) wherein $R^5$ represents difluoromethoxy by a two-step process which comprises: (i) reaction with potassium hydroxide in water at low temperature; and (ii) reaction with diethyl (bromodifluoromethyl)phosphonate at low temperature.

The intermediates of formula (X) wherein E represents a group of formula (Ea) as defined above, and $R^{12}$ represents hydrogen, may be prepared by a process which comprises the reduction, intramolecular cyclization and desulfination of an intermediate of formula (XIIIa):

(XIIIa)

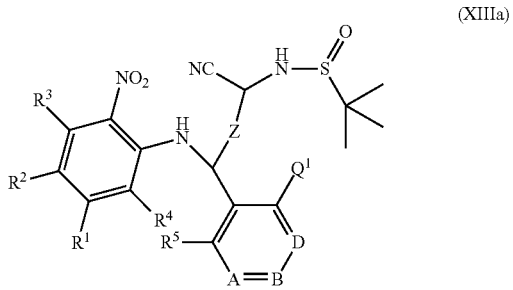

wherein A, B, D, Z, $R^1$, $R^2$, $R^3$, $R^4$, $R^5$ and $Q^1$ are as defined above.

The reaction is conveniently performed in the presence of tin(II) chloride, with the addition of a strong acid, e.g. hydrochloric acid, at an elevated temperature in a suitable solvent, e.g. ethanol.

Alternatively, the transformation may be effected by a procedure involving: (i) reduction using hydrogen gas under pressure, in the presence of zinc bromide and a hydrogenation catalyst, e.g. platinum on charcoal; and (ii) addition of a strong acid, e.g. hydrochloric acid, at an elevated temperature in a suitable solvent, e.g. ethanol.

The intermediates of formula (XIIIa) may be prepared by a multi-step process starting from an intermediate of formula (XIVa):

(XIVa)

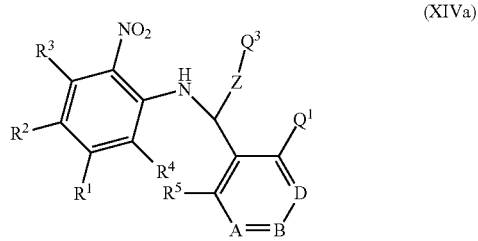

wherein A, B, D, Z, $R^1$, $R^2$, $R^3$, $R^4$, $R^5$ and $Q^1$ are as defined above, and $Q^3$ represents —CH=$CH_2$; which process comprises the following steps:

(i) reacting intermediate (XIVa) with sodium periodate, in the presence of potassium dioxido(dioxo)osmium hydrate and a base, e.g. N,N-dimethylpyridinyl-4-amine or 2,6-dimethylpyridine, followed by addition of sodium thiosulfate, to afford the corresponding intermediate of formula (XIVa) wherein $Q^3$ represents —CH=O;

(ii) reacting the compound thereby obtained with (R)-2-methylpropane-2-sulfinamide in the presence of a transition metal catalyst, e.g. titanium(IV) isopropoxide, in a suitable solvent, e.g. dichloromethane, to afford the corresponding intermediate of formula (XIVa) wherein $Q^3$ represents —CH=N—S(=O)—C$(CH_3)_3$; and (iii) reacting the compound thereby obtained with sodium cyanide in the presence of scandium triflate in a suitable solvent, e.g. tetrahydrofuran.

The intermediates of formula (XIVa) as defined above may be prepared by reacting an intermediate of formula (XV) as defined above with an intermediate of formula (XVIa):

(XVIa)

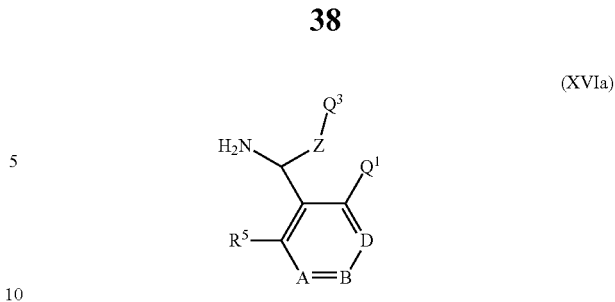

wherein A, B, D, Z, $R^5$, $Q^1$ and $Q^3$ are as defined above; under conditions analogous to those described above for the preparation of the intermediates of formula (XIV).

The intermediates of formula (XVIa) may be prepared from the intermediates of formula (XVII) by a process analogous to that described above for the preparation of the intermediates of formula (XVI).

The intermediates of formula (VI) wherein E represents a group of formula (Eb) or (Ec) as defined above, and $R^{12}$ and $R^q$ both represent hydrogen, may be prepared from an intermediate of formula (XVIII):

(XVIII)

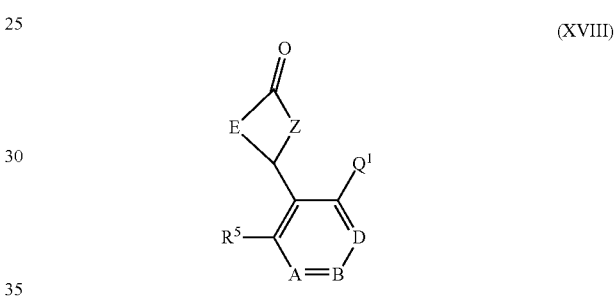

wherein A, B, D, Z, E, $R^5$ and $Q^1$ are as defined above; by reduction of the carbonyl moiety according to methods known to the person skilled in the art.

The intermediates of formula (X) wherein E represents a group of formula (Eb) or (Ec) as defined above, and $R^{12}$ represents methyl, may be prepared from an intermediate of formula (XVIII) utilising the following sequence of steps:

(i) reacting an intermediate of formula (XVIII) with 2-methylpropane-2-sulfinamide in the presence of titanium (IV) isopropoxide in a solvent, e.g. tetrahydrofuran;

(ii) adding a solution of methylmagnesium bromide, at low temperature, in a suitable solvent, e.g. dichloromethane; and (iii) removing the tert-butylsulphinyl moiety by treatment with a strong acid, e.g. hydrochloric acid, in a suitable solvent, e.g. 1,4-dioxane.

Alternatively, the intermediates of formula (X) wherein E represents a group of formula (Eb) or (Ec) as defined above, and $R^{12}$ represents hydrogen, may be prepared from an intermediate of formula (XVIII) by reaction with a $C_{1-6}$ alkylsulfinamide, e.g. (R)-2-methylpropane-2-sulfinamide, in the presence of a transition metal catalyst, e.g. titanium (IV) ethoxide, in a suitable solvent, e.g. dichloromethane; followed by reduction with a suitable reducing agent, e.g. sodium borohydride, in a suitable solvent, e.g. tetrahydrofuran; and subsequent removal of the sulfinyl moiety, typically by treatment with a mineral acid, e.g. hydrochloric acid.

The intermediates of formula (XVIII) may be prepared by the intramolecular cyclization of an intermediate of formula (XIX):

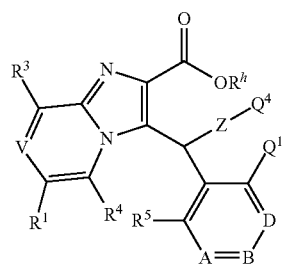

(XIX)

wherein V is N or C—R², Q⁴ is an electron-withdrawing group, preferably an ester moiety, and A, B, D, Z, R¹, R², R³, R⁴, R⁵, R$^h$ and Q¹ are as defined above; in the presence of a base.

The reaction may conveniently be effected in a suitable solvent at an elevated temperature.

The intermediates of formula (XIX) may be prepared by reacting an intermediate of formula (XX) with an intermediate of formula (XXI):

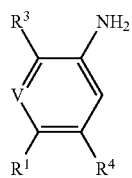

(XX)

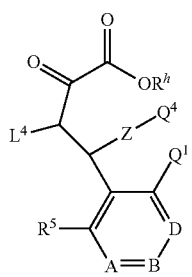

(XXI)

wherein A, B, D, V, Z, R¹, R³, R⁴, R⁵, R$^h$, Q¹ and Q⁴ are as defined above, and L⁴ represents a suitable leaving group.

The leaving group L⁴ is typically a halogen atom, e.g. bromo.

The reaction is conveniently effected at an elevated temperature in a suitable solvent, e.g. a $C_{1-4}$ alkanol such as ethanol, or an ether such as 1,4-dioxane or 1,2-dimethoxyethane, typically in the presence of magnesium sulphate.

Alternatively, the intermediates of formula (XIX) wherein Z is methylene and Q⁴ is —CO₂H may be prepared by reacting an intermediate of formula (XVII) as defined above with an intermediate of formula (XXII):

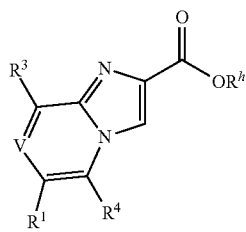

(XXII)

wherein V, R¹, R³, R⁴ and R$^h$ are as defined above; in the presence of Meldrum's acid, according to a method analogous to that described in WO 2009/156091; or by M. Kerr et al. in *J. Org. Chem.*, 2013, 78, 10534.

The reaction is conveniently effected at an elevated temperature in a suitable solvent, e.g. acetonitrile, in the presence of proline and magnesium sulphate.

The compounds of formula (I) above wherein the moiety —(X-M-Q)- represents a group of formula (Mf) as defined above, in which $R^{1m}$ and $R^{2m}$ are both hydrogen, may be prepared by a multi-step procedure which comprises the following steps:

(i) reacting a compound of formula (XXIII) with an organometallic reagent of formula (XXIV):

(XXIII)

(XXIV)

wherein M² represents —Li or —MgHal, in which Hal represents a halogen atom, e.g. chloro or bromo, and A, B, D, Z, E, R⁵, R¹² and R$^q$ are as defined above;

(ii) removal of the O-protecting group R$^q$, where present;

(iii) treatment of the compound thereby obtained with a suitable oxidising agent, e.g. 1,1,1-tris(acetyloxy)-1,1-dihydro-1,2-benziodoxol-3-(1H)-one (Dess-Martin periodinane), or a mixture of oxalyl chloride and dimethyl sulfoxide (Swern oxidation), to effect aldehyde formation and concomitant intramolecular cyclisation; and (iv) treatment of the compound thereby obtained with a suitable reducing agent, e.g. sodium borohydride or sodium cyanoborohydride.

The compounds of formula (I) above wherein the moiety —(X-M-Q)- represents a group of formula (Mg) as defined above, in which $R^{1m}$ and $R^{2m}$ are both hydrogen, may be prepared from a compound of formula (XXIII) as defined above and a compound of formula (XXV):

(XXV)

wherein M² and R$^q$ are as defined above; by a multi-step procedure analogous to that described above for the preparation of the compounds of formula (I) wherein —(X-M-Q)-represents a group of formula (Mf).

The compounds of formula (I) above wherein the moiety —(X-M-Q)- represents a group of formula (Mh) as defined above, in which $R^{1m}$ and $R^{2m}$ are both hydrogen, may be prepared by a multi-step procedure which comprises the following steps:

(i) reacting a compound of formula (XXIII) as defined above with an organometallic reagent of formula (XXIV) as defined above;

(ii) removal of the O-protecting group $R^q$, where present;

(iii) treatment of the compound thereby obtained with a suitable oxidising agent, e.g. potassium permanganate, or pyridinium dichromate in N,N-dimethylformamide, or a mixture of chromic acid, aqueous sulphuric acid and acetone (Jones oxidation); and (iv) heating the carboxylic acid derivative thereby obtained, or treatment thereof with a suitable amide coupling reagent, e.g. N-(3-dimethylaminopropyl)-N'-ethyl-carbodiimide (EDC) or N,N'-dicyclohexylcarbodiimide (DCC), to effect intramolecular cyclisation.

The compounds of formula (I) above wherein the moiety —(X-M-Q)- represents a group of formula (Mi) as defined above, in which $R^{1m}$ and $R^{2m}$ are both hydrogen, may be prepared from a compound of formula (XXIII) as defined above and a compound of formula (XXV) as defined above by a multi-step procedure analogous to that described above for the preparation of the compounds of formula (I) wherein —(X-M-Q)- represents a group of formula (Mh).

The compounds of formula (I) above wherein the moiety —(X-M-Q)- represents a group of formula (Mj) as defined above, in which $R^{1m}$ and $R^{2m}$ are both hydrogen, may be prepared by a multi-step procedure which comprises the following steps:

(i) reacting a compound of formula (XXIII) as defined above with trimethylsilyl cyanide;

(ii) hydrolysis of the cyano derivative thereby obtained, typically by treatment with a mineral acid, e.g. hydrochloric acid or sulphuric acid;

(iii) treatment of the resulting carboxylic acid derivative with a suitable reducing agent, e.g. borane dimethyl sulphide complex or lithium aluminium hydride; and (iv) treatment of the hydroxy derivative thereby obtained with phosgene or 1,1'-carbonyldiimidazole.

The compounds of formula (I) above wherein the moiety —(X-M-Q)- represents a group of formula (Mk) as defined above, in which $R^{1m}$ and $R^{2m}$ are both hydrogen, may be prepared by a multi-step procedure which comprises the following steps:

(i) reacting a compound of formula (XXIII) as defined above with an organometallic reagent of formula (XXVI):

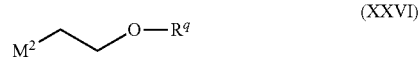

(XXVI)

wherein $R^q$ and $M^2$ are as defined above;

(ii) removal of the O-protecting group $R^q$, where present; and (iii) treatment of the hydroxy derivative thereby obtained with phosgene or 1,1'-carbonyldiimidazole (CDI).

The compounds of formula (I) above wherein the moiety —(X-M-Q)- represents a group of formula (Ml) as defined above, in which $R^{1m}$ and $R^{2m}$ are both hydrogen, may be prepared by a multi-step procedure which comprises the following steps:

(i) reacting a compound of formula (XXIII) as defined above with an organometallic reagent of formula (XXVI) as defined above;

(ii) removal of the O-protecting group $R^q$, where present;

(iii) treatment of the compound thereby obtained with a suitable oxidising agent, e.g. potassium permanganate, or pyridinium dichromate in N,N-dimethylformamide, or a mixture of chromic acid, aqueous sulphuric acid and acetone (Jones oxidation); and (iv) treatment of the carboxylic acid derivative thereby obtained with diphenyl phosphoryl azide, to effect formation of the corresponding isocyanate derivative and concomitant intramolecular cyclisation.

Alternatively, step (iv) can be carried out in the presence of tert-butanol to obtain the BOC-protected amine derivative, which can then be deprotected by treatment with acid (HCl or TFA) and subsequently treated with phosgene or CDI to provide the required product.

The compounds of formula (I) above wherein the moiety —(X-M-Q)- represents a group of formula (Mm) as defined above, in which $R^{1m}$ and $R^{2m}$ are both hydrogen, may be prepared from a compound of formula (XXIII) as defined above and a compound of formula (XXIV) as defined above by a multi-step procedure analogous to that described above for the preparation of the compounds of formula (I) wherein —(X-M-Q)- represents a group of formula (Ml).

The skilled person will appreciate that the compounds of formula (I) above wherein the moiety —(X-M-Q)- represents a group of formula (Mf), (Mg), (Mh), (Mi), (Mk), (Ml) or (Mm) as defined above, in which $R^{1m}$ and/or $R^{2m}$ is other than hydrogen, may be prepared by commencing from an analogue of a compound of formula (XXIV), (XXV) or (XXVI) that is substituted, as appropriate, with the requisite substituent of formula $R^{1m}$ and/or $R^{2m}$.

The intermediates of formula (XXIII) above may be prepared by a multi-step procedure which comprises the following steps:

(i) reacting a compound of formula (X) as defined above with tert-butyl dicarbonate;

(ii) reaction of the BOC-protected amine derivative thereby obtained with potassium vinyltrifluoroborate in the presence of a transition metal catalyst;

(iii) reaction of the vinyl-substituted compound thereby obtained with osmium tetroxide and sodium periodate; and (iv) treatment of the resulting aldehyde derivative with trifluoroacetic acid, to effect removal of the BOC protecting group and concomitant intramolecular cyclization.

The transition metal catalyst of use in step (ii) of the above procedure may suitably be a palladium catalyst such as [1,1'-bis(diphenylphosphino)ferrocene]palladium(II) dichloride dichloromethane complex. The reaction is conveniently effected at an elevated temperature in the presence of a base, e.g. an alkali metal carbonate such as cesium carbonate, in a suitable organic solvent, e.g. a cyclic ether such as 1,4-dioxane, and water.

Step (iii) of the above procedure may conveniently be effected at ambient temperature in a suitable organic solvent, e.g. a cyclic ether such as 1,4-dioxane, and water.

Where they are not commercially available, the starting materials of formula (V), (VIII), (XV), (XVII), (XX), (XXI), (XXII), (XXIV), (XXV) and (XXVI) may be prepared by methods analogous to those described in the accompanying Examples, or by standard methods well known from the art.

It will be understood that any compound of formula (I) initially obtained from any of the above processes may, where appropriate, subsequently be elaborated into a further compound of formula (I) by techniques known from the art.

By way of example, a compound which contains a hydroxy group may be alkylated by treatment with the appropriate alkyl halide in the presence of a base, e.g. sodium hydride, or silver oxide.

A compound which contains hydroxy may be converted into the corresponding fluoro-substituted compound by treatment with diethylaminosulfur trifluoride (DAST) or bis(2-methoxyethyl)amino sulfur trifluoride (BAST). A compound which contains hydroxy may be converted into the corresponding difluoro-substituted compound via a two-step procedure which comprises: (i) treatment with an oxidising agent, e.g. manganese dioxide; and (ii) treatment of the carbonyl-containing compound thereby obtained with DAST.

A compound which contains an N—H moiety may be alkylated by treatment with the appropriate alkyl halide, typically at an elevated temperature in an organic solvent such as acetonitrile; or at ambient temperature in the presence of a base, e.g. potassium hydroxide, in a suitable solvent, e.g. tetrahydrofuran, in the presence of tetrabutylammonium bromide; or at an elevated temperature in the presence of a base, e.g. sodium hydride, with or without tetrabutylammonium iodate, in a suitable solvent, e.g. tetrahydrofuran; or at elevated temperature in the presence of an alkali metal carbonate such as potassium carbonate or cesium carbonate, in a suitable solvent, e.g. a dipolar aprotic solvent such as N,N-dimethylformamide. A compound which contains an N—H moiety may be methylated by treatment with formaldehyde in the presence of a reducing agent, e.g. sodium triacetoxyborohydride.

A compound which contains an N—H moiety may be acylated by treatment with the appropriate acid chloride, e.g. acetyl chloride, or with the appropriate carboxylic acid anhydride, e.g. acetic anhydride, typically at ambient temperature in the presence of a base, e.g. an organic base such as triethylamine.

A compound which contains an N—H moiety may be converted into the corresponding compound wherein the nitrogen atom is substituted by $C_{1-6}$ alkylsulphonyl, e.g. methylsulphonyl, by treatment with the appropriate $C_{1-6}$ alkylsulphonyl chloride, e.g. methanesulphonyl chloride, or with the appropriate $C_{1-6}$ alkylsulphonic acid anhydride, e.g. methanesulphonic anhydride, typically at ambient temperature in the presence of a base, e.g. an organic base such as triethylamine or N,N-diisopropylethylamine.

A compound which contains an N—H moiety may be converted into the corresponding compound wherein the nitrogen atom is substituted by $C_{1-6}$ alkoxycarbonyl, e.g. methoxycarbonyl, by treatment with the corresponding $C_{1-6}$ alkoxycarbonyl halide in the presence of a base, e.g. potassium carbonate, in a suitable solvent, e.g. N,N-dimethylformamide.

A compound substituted by amino (—NH$_2$) may be converted into the corresponding compound substituted by $C_{1-6}$ alkylsulphonylamino, e.g. methylsulphonylamino, or bis[($C_{1-6}$)alkylsulphonyl]amino, e.g. bis(methylsulphonyl) amino, by treatment with the appropriate $C_{1-6}$ alkylsulphonyl halide, e.g. a $C_{1-6}$ alkylsulphonyl chloride such as methanesulphonyl chloride, in the presence of a suitable base, e.g. N,N-diisopropylethylamine, in a suitable solvent, e.g. dichloromethane.

Thus, a compound substituted by amino may be transformed into the corresponding compound substituted by —NHSO$_2$R$^e$ by treatment with a compound of formula R$^e$—SO$_2$Cl.

Similarly, a compound substituted by hydroxy (—OH) may be converted into the corresponding compound substituted by $C_{1-6}$ alkylsulphonyloxy, e.g. methylsulphonyloxy, by treatment with the appropriate $C_{1-6}$ alkylsulphonyl halide, e.g. a $C_{1-6}$ alkylsulphonyl chloride such as methanesulphonyl chloride.

A compound containing the moiety —S— may be converted into the corresponding compound containing the moiety —S(O)— by treatment with 3-chloroperoxybenzoic acid. Likewise, a compound containing the moiety —S(O)— may be converted into the corresponding compound containing the moiety —S(O)$_2$— by treatment with 3-chloroperoxybenzoic acid. Alternatively, a compound of formula (I) containing the moiety —S— may be converted into the corresponding compound containing the moiety —S(O)$_2$— by treatment with Oxone® (potassium peroxymonosulfate).

A compound containing an aromatic nitrogen atom may be converted into the corresponding N-oxide derivative by treatment with 3-chloroperoxybenzoic acid.

A compound which contains a carbonyl (C=O) moiety may be converted into the corresponding compound containing a CH(OH) functionality by treatment with a suitable borohydride reagent, e.g. lithium tri-sec-butyl borohydride or sodium borohydride, in a suitable solvent e.g. tetrahydrofuran.

A compound wherein R$^1$ represents halogen, e.g. chloro or bromo, may be converted into the corresponding compound wherein R$^1$ represents an optionally substituted aryl or heteroaryl moiety by treatment with the appropriately substituted aryl or heteroaryl boronic acid or a cyclic ester thereof formed with an organic diol, e.g. pinacol, 1,3-propanediol or neopentyl glycol. The reaction is typically effected at an elevated temperature in the presence of a transition metal catalyst, e.g. [1,1'-bis(diphenyl-phosphino) ferrocene]dichloropalladium(II), tetrakis(triphenylphosphine)palladium(0), bis[3-(diphenylphosphanyl)cyclopenta-2,4-dien-1-yl]iron-dichloropalladium-dichloromethane complex, or tris(dibenzylideneacetone)dipalladium(0) and tricyclohexylphosphonium tetrafluoroborate, and a base, e.g. an inorganic base such as sodium carbonate, potassium carbonate or cesium carbonate, or potassium phosphate, in a suitable organic solvent, e.g. 1,4-dioxane or n-butanol, and optionally water.

A compound wherein R$^1$ represents halogen, e.g. chloro or bromo, may be converted into the corresponding compound wherein R$^1$ represents an optionally substituted aryl or heteroaryl moiety via a two-step procedure which comprises: (i) reaction with bis(pinacolato)diboron in the presence of a transition metal catalyst; and (ii) reaction of the compound thereby obtained with an appropriately functionalised halo-substituted aryl or heteroaryl derivative, also in the presence of a transition metal catalyst. The transition metal catalyst of use in step (i) may suitably be tris(dibenzylideneacetone)palladium(0), and the reaction may be conveniently effected in the presence of tricyclohexylphosphonium tetrafluoroborate and potassium acetate. The transition metal catalyst of use in step (ii) may suitably be tris (dibenzylideneacetone)palladium(0), and the reaction may be conveniently effected in the presence of tricyclohexylphosphonium tetrafluoroborate and potassium phosphate.

A compound wherein R$^1$ represents 2-oxo-(1H)-pyridinyl may be obtained by treatment of the corresponding compound wherein R$^1$ represents 2-methoxypyridinyl with pyridine hydrochloride at an elevated temperature.

A compound wherein R$^1$ represents an ester moiety may be obtained by reacting the corresponding compound wherein R$^1$ is halogen, e.g. chloro, with a base, e.g. sodium carbonate, and the appropriate alcohol in the presence of carbon monoxide and a transition metal catalyst, typically [1,3-bis(dicyclohexylphosphino)propane]palladium(II).

A compound wherein $R^1$ represents cyano may be obtained by reacting the corresponding compound wherein $R^1$ is halogen, e.g. chloro, with zinc cyanide in the presence of a transition metal catalyst, e.g. tetrakis(triphenylphosphine)palladium(0), in a suitable solvent, e.g. N,N-dimethylformamide.

In general, a compound containing a —C≡C— functionality may be converted into the corresponding compound containing a —CH—CH— functionality by catalytic hydrogenation, typically by treatment with a hydrogenation catalyst, e.g. palladium on charcoal, under an atmosphere of hydrogen gas, optionally in the presence of a base, e.g. an alkali metal hydroxide such as sodium hydroxide.

A compound containing an ester moiety, e.g. a $C_{2-6}$ alkoxycarbonyl group such as methoxycarbonyl or ethoxycarbonyl, may be converted into the corresponding compound containing a carboxy (—$CO_2H$) moiety by treatment with an acid, e.g. a mineral acid such as hydrochloric acid.

A compound containing an ester moiety, e.g. a $C_{2-6}$ alkoxycarbonyl group such as methoxycarbonyl or ethoxycarbonyl, may alternatively be converted into the corresponding compound containing a carboxy (—$CO_2H$) moiety by treatment with a base, e.g. an alkali metal hydroxide selected from lithium hydroxide, sodium hydroxide and potassium hydroxide; or an organic base such as sodium methoxide or sodium ethoxide.

A compound containing a carboxy (—$CO_2H$) moiety may be converted into the corresponding compound containing an amide moiety by treatment with the appropriate amine in the presence of a condensing agent such as 1-ethyl-3-(3-dimethylaminopropyl)carbodiimide.

A compound containing an N-(tert-butoxycarbonyl) moiety may be converted into the corresponding compound containing an N—H moiety by treatment with an acid, e.g. a mineral acid such as hydrochloric acid, or an organic acid such as trifluoroacetic acid.

A compound containing a carbonyl (C=O) moiety may be converted into the corresponding compound containing a —C($CH_3$)(OH)— moiety by treatment with methylmagnesium bromide. Similarly, a compound containing a carbonyl (C=O) moiety may be converted into the corresponding compound containing a —C($CF_3$)(OH)— moiety by treatment with (trifluoromethyl)trimethylsilane and cesium fluoride. A compound containing a carbonyl (C=O) moiety may be converted into the corresponding compound containing a —C($CH_2NO_2$)(OH)— moiety by treatment with nitromethane.

A compound containing a hydroxymethyl moiety may be converted into the corresponding compound containing a formyl (—CHO) moiety by treatment with an oxidising agent such as Dess-Martin periodinane. A compound containing a hydroxymethyl moiety may be converted into the corresponding compound containing a carboxy moiety by treatment with an oxidising agent such as tetrapropylammonium perruthenate.

A compound containing an aryl or heteroaryl moiety may be transformed into the corresponding compound, wherein a hydrogen atom in the aryl or heteroaryl moiety has been replaced by chloro or bromo, by reaction with N-chlorosuccinimide or N-bromo-succinimide respectively in a suitable solvent, e.g. N,N-dimethylformamide, according to methods known to the person skilled in the art.

A compound containing an aryl moiety bearing a difluoromethoxy group may be transformed into the corresponding compound, wherein the difluoromethoxy group in the aryl moiety has been replaced by a hydroxy group, by reaction with sodium bis(trimethylsilyl)amide (NaHMDS) in a suitable solvent, e.g. tetrahydrofuran.

A compound containing an aryl or heteroaryl moiety may be transformed into the corresponding compound, wherein a hydrogen atom in the aryl or heteroaryl moiety has been replaced by trifluoromethyl, by a stepwise procedure which comprises: (i) treatment with trifluoroacetic acid in a suitable solvent, e.g. acetonitrile; and (ii) addition of trifluoromethanesulphonyl chloride, followed by [4,4'-bis(tert-butyl)-2,2'-bipyridine]bis-{3,5-difluoro-2-[5-(trifluoromethyl)pyridin-2-yl]phenyl}iridium(III) hexafluorophosphate, according to conditions analogous to those described by McMillan et al. in *Nature,* 2011, 480, 224.

A compound substituted by phosphate($C_{1-6}$)alkyl may be prepared from the corresponding compound substituted by hydroxy($C_{1-6}$)alkyl by a stepwise procedure which comprises: (i) treatment with dibenzyl N,N-diisopropylphosphoramidite in a suitable solvent, e.g. dichloromethane, followed by treatment with hydrogen peroxide; and (ii) hydrogenolysis, e.g. using hydrogen gas under pressure, in the presence of a suitable catalyst, e.g. palladium on charcoal, according to a method analogous to those described by S. P. Green et al. in *Organic Process Research & Development,* 2002, 6, 109-112. A compound substituted by a salt of phosphate($C_{1-6}$)alkyl may be prepared by performing step (ii) in the presence of a suitable alkali metal base or alkaline earth metal base. Similarly, an isolated compound substituted by phosphate($C_{1-6}$)alkyl may be converted into the corresponding compound substituted by a salt of phosphate ($C_{1-6}$)alkyl by treatment with an appropriate base, e.g. an alkali metal base, or an alkaline earth metal base, or ammonia, or an organic amine, in a suitable solvent according to methods known to the person skilled in the art. Suitable alkali metal bases include sodium hydroxide and potassium hydroxide. Suitable alkaline earth metal bases include calcium hydroxide. Suitable organic amines include triethylamine.

A compound substituted by ($C_{1-6}$)alkylphosphate($C_{1-6}$)alkyl may be prepared from the corresponding compound substituted by hydroxy($C_{1-6}$)alkyl by a stepwise procedure which comprises: (i) reacting cyanoethyl phosphoramidite with the appropriate $C_{1-6}$ alkanol in the presence of a base, e.g. N,N-diisopropylethylamine, in a suitable solvent, e.g. dichloromethane; (ii) addition of the relevant compound substituted by hydroxy-($C_{1-6}$)alkyl in a suitable solvent, e.g. dichloromethane; and (iii) oxidation and subsequent treatment with a suitable base, according to a method analogous to those described by Nam, N—H. et al. in *Bio-org. Med. Chem.,* 2004, 12, 6255; and in WO 2012/177707.

A compound substituted by sulphate($C_{1-6}$)alkyl may be prepared by treatment of the corresponding compound substituted by hydroxy($C_{1-6}$)alkyl with pyridine: sulphur trioxide complex, according to a method analogous to that described by E. Lacko et al. in *Current Medicinal Chemistry,* 2012, 19, 4699; or by treatment with chlorosulphonic acid in the presence of triethylamine, according to a method analogous to that described in WO 2004/087720.

A compound substituted by phosphate-methoxy($C_{1-6}$)alkyl may be prepared by reacting the corresponding compound substituted by hydroxy($C_{1-6}$)alkyl with a suitable base, e.g. sodium hydride, in a suitable solvent, e.g. 1,2-dimethoxyethane, followed by addition of chloromethyl di-tert-butylphosphate, with subsequent dealkylation at an elevated temperature, according to a method analogous to that described in WO 2012/135082.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention. Alternatively the non-desired enantiomer may be racemized into the desired enantiomer, in the presence of an acid or a base, according to methods known to the person skilled in the art, or according to methods described in the accompanying Examples.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3$^{rd}$ edition, 1999. The protecting groups may be removed at any convenient subsequent stage utilising methods known from the art.

Compounds in accordance with the present invention potently neutralise the activity of TNFα in a commercially available HEK-293 derived reporter cell line known as HEK-Blue™ CD40L. This is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a concentration-dependent manner by TNFα. When tested in the HEK-293 bioassay, also referred to herein as the reporter gene assay, compounds of the present invention exhibit an $IC_{50}$ value of 50 μM or less, generally of 20 μM or less, usually of 5 μM or less, typically of 1 μM or less, suitably of 500 nM or less, ideally of 100 nM or less, and preferably of 25 nM or less (the skilled person will appreciate that a lower $IC_{50}$ figure denotes a more active compound).

Certain compounds in accordance with the present invention potently inhibit the binding of a fluorescence conjugate to TNFα when tested in the fluorescence polarisation assay described herein. Indeed, when tested in that assay, compounds of the present invention exhibit an $IC_{50}$ value of 50 μM or less, generally of 20 μM or less, usually of 5 μM or less, typically of 1 μM or less, suitably of 500 nM or less, ideally of 100 nM or less, and preferably of 25 nM or less (as before, the skilled person will appreciate that a lower $IC_{50}$ figure denotes a more active compound).

The compounds of the Examples have been tested in one or both of the assays described below.

Fluorescence Polarisation Assay

Preparation of Compound (A)

1-(2,5-Dimethylbenzyl)-6-[4-(piperazin-1-ylmethyl)phenyl]-2-(pyridin-4-yl-methyl)-1H-benzimidazole—hereinafter referred to as "Compound (A)"—can be prepared by the procedure described in Example 499 of WO 2013/186229; or by a procedure analogous thereto.

Preparation of Fluorescence Conjugate

Compound (A) (27.02 mg, 0.0538 mmol) was dissolved in DMSO (2 mL). 5 (-6) Carboxy-fluorescein succinimyl ester (24.16 mg, 0.0510 mmol) (Invitrogen catalogue number: C1311) was dissolved in DMSO (1 mL) to give a bright yellow solution. The two solutions were mixed at room temperature, the mixture turning red in colour. The mixture was stirred at room temperature. Shortly after mixing a 20 μL aliquot was removed and diluted in a 80:20 mixture of AcOH:H$_2$O for LC-MS analysis on the 1200RR-6140 LC-MS system. The chromatogram showed two closely eluting peaks at retention times of 1.42 and 1.50 minutes, both with mass $(M+H)^+$=860.8 amu, corresponding to the two products formed with the 5- and 6-substituted carboxyfluorescein group. A further peak at retention time 2.21 minutes had a mass of $(M+H)^+$=502.8 amu, corresponding to Compound (A). No peak was observed for unreacted 5(-6) carboxyfluorescein succinimyl ester. The peak areas were 22.0%, 39.6% and 31.4% for the three signals, indicating a 61.6% conversion to the two isomers of the desired fluorescence conjugate at that time-point. Further 20 μL aliquots were extracted after several hours and then after overnight stirring, diluted as before and subjected to LC-MS analysis. The percentage conversion was determined as 79.8% and 88.6% respectively at these time-points. The mixture was purified on a UV-directed preparative HPLC system. The pooled purified fractions were freeze-dried to remove excess solvent. After freeze-drying, an orange solid (23.3 mg) was recovered, equivalent to 0.027 mmol of fluorescence conjugate, corresponding to an overall yield of 53% for the reaction and preparative HPLC purification.

Inhibition of Binding of Fluorescence Conjugate to TNFα

Compounds were tested at 10 concentrations starting from 25 μM in a final assay concentration of 5% DMSO, by pre-incubation with TNFα for 60 minutes at ambient temperature in 20 mM Tris, 150 mM NaCl, 0.05% Tween 20, before addition of the fluorescence conjugate and a further incubation for 20 hours at ambient temperature. The final concentrations of TNFα and the fluorescence conjugate were 10 nM and 10 nM respectively in a total assay volume of 25 μL. Plates were read on a plate reader capable of detecting fluorescence polarisation (e.g. an Analyst HT plate reader; or an Envision plate reader). An $IC_{50}$ value was calculated using XLfit™ (4 parameter logistic model) in ActivityBase.

When tested in the fluorescence polarisation assay, compounds of the accompanying Examples were found to exhibit $IC_{50}$ values of 50 μM or better.

When tested in the fluorescence polarisation assay, compounds of the accompanying Examples exhibit $IC_{50}$ values generally in the range of about 0.01 nM to about 50 µM, usually in the range of about 0.01 nM to about 20 µM, typically in the range of about 0.01 nM to about 5 µM, suitably in the range of about 0.01 nM to about 1 µM, ideally in the range of about 0.01 nM to about 500 nM, appositely in the range of about 0.01 nM to about 100 nM, and preferably in the range of about 0.01 nM to about 25 nM.

Reporter Gene Assay

Inhibition of TNFα-Induced NF-κB Activation

Stimulation of HEK-293 cells by TNFα leads to activation of the NF-κB pathway. The reporter cell line used to determine TNFα activity was purchased from InvivoGen. HEK-Blue™ CD40L is a stable HEK-293 transfected cell line expressing SEAP (secreted embryonic alkaline phosphatase) under the control of the IFNβ minimal promoter fused to five NF-κB binding sites. Secretion of SEAP by these cells is stimulated in a dose-dependent manner by TNFα, with an EC50 of 0.5 ng/mL for human TNFα. Compounds were diluted from 10 mM DMSO stocks (final assay concentration 0.3% DMSO) to generate a 10-point 3-fold serial dilution curve (e.g. 30,000 nM to 2 nM final concentration). Diluted compound was preincubated with TNFα for 60 minutes prior to addition to a 384-well microtitre plate and incubated for 18 h. The final TNFα concentration in the assay plate was 0.5 ng/mL. SEAP activity was determined in the supernatant using a colorimetric substrate, e.g. QUANTI-Blue™ or HEK-Blue™ Detection media (InvivoGen). Percentage inhibitions for compound dilutions were calculated between a DMSO control and maximum inhibition (by excess control compound) and an $IC_{50}$ value calculated using XLfit™ (4 parameter logistic model) in ActivityBase.

When tested in the reporter gene assay, the compounds of the accompanying Examples were all found to exhibit $IC_{50}$ values of 50 µM or better.

When tested in the reporter gene assay, compounds of the accompanying Examples exhibit $IC_{50}$ values generally in the range of about 0.01 nM to about 50 µM, usually in the range of about 0.01 nM to about 20 µM, typically in the range of about 0.01 nM to about 5 µM, suitably in the range of about 0.01 nM to about 1 µM, appositely in the range of about 0.01 nM to about 500 nM, ideally in the range of about 0.01 nM to about 100 nM, and preferably in the range of about 0.01 nM to about 25 nM.

The following Examples illustrate the preparation of compounds according to the invention.

EXAMPLES

Abbreviations

DCM: dichloromethane
DMF: N,N-dimethylformamide
DMSO: dimethyl sulfoxide
EtOH: ethanol
DIBAL-H: diisobutylaluminium hydride
DIAD: diisopropyl (E)-1,2-diazenedicarboxylate
Lawesson's reagent: 2,4-bis(4-methoxyphenyl)-1,3,2,4-dithiadiphosphetane-2,4-dithione
XPhos: 2-dicyclohexylphosphino-2',4',6'-triisopropylbiphenyl
2nd generation XPhos precatalyst: chloro(2-dicyclohexylphosphino-2',4',6'-triisopropyl-1,1'-biphenyl)[2-(2'-amino-1,1'-biphenyl)]palladium(II)
h: hour
M: mass
EtOAc: ethyl acetate
MeOH: methanol
THF: tetrahydrofuran
DEA: diethanolamine
r.t.: room temperature
RT: retention time
HPLC: High Performance Liquid Chromatography
LCMS: Liquid Chromatography Mass Spectrometry
ES+: Electrospray Positive Ionisation Analytical Conditions All NMR spectra were obtained either at 300 MHz or at 400 MHz.

All reactions involving air-or moisture-sensitive reagents were performed under a nitrogen atmosphere using dried solvents and glassware.

LCMS Data Determination

Method 1

A QDA Waters simple quadrupole mass spectrometer is used for LC-MS analysis.

This spectrometer is equipped with an ESI source and an UPLC Acquity Classic with diode array detector (210 to 400 nm).

Data are acquired in a full MS scan from m/z 50 to 1000 in positive mode with an acidic elution.

The reverse phase separation is carried out at 45° C. on a Waters Acquity UPLC BEH C18 1.7 µm (2.1×50 mm) column for basic elution.

Gradient Elution is Performed with:

$H_2O$/acetonitrile/ammonium formate (95/5/63 mg/L)+50 µL $NH_4OH$ (solvent A)

Acetonitrile/$H_2O$/ammonium formate (95/5/63 mg/L)+50 µL $NH_4OH$ (solvent B)

Gradient Program:

HPLC flow rate: 0.4 mL/minute to 0.4 mL/minute

Injection volume: 1 µL

Full flow in MS.

| Time (min) | A (%) | B (%) | Flow (mL/min) |
|---|---|---|---|
| 0 | 99 | 1 | 0.4 |
| 0.3 | 99 | 1 | 0.4 |
| 3.2 | 0 | 100 | 0.4 |
| 3.25 | 0 | 100 | 0.5 |
| 4 | 0 | 100 | 0.5 |
| 4.1 | 99 | 1 | 0.4 |
| 4.8 | 90 | 1 | 0.4 |

Method 2

A QDA Waters simple quadrupole mass spectrometer is used for LC-MS analysis.

This spectrometer is equipped with an ESI source and an UPLC Acquity Hclass with diode array detector (210 to 400 nm).

Data are acquired in a full MS scan from m/z 50 to 1000 in positive mode with an acidic elution.

The reverse phase separation is carried out at 45° C. on a Waters Acquity UPLC HSS T3 1.8 µm (2.1×50 mm) column for acidic elution.

Gradient Elution is Performed with:

Water (solvent A)

Acetonitrile (solvent B)

Water/acetonitrile/formic acid 0.5% (solvent C)

Gradient Program:

HPLC flow rate: 0.6 mL/minute to 0.7 mL/minute

Injection volume: 1 µL

Full flow in MS.

| Time (min) | A (%) | B (%) | C (%) | Flow (mL/min) |
|---|---|---|---|---|
| 0 | 90 | 0 | 10 | 0.6 |
| 0.3 | 90 | 0 | 10 | 0.6 |
| 3.2 | 0 | 90 | 10 | 0.6 |
| 3.25 | 0 | 90 | 10 | 0.7 |
| 4 | 0 | 90 | 10 | 0.7 |
| 4.1 | 90 | 0 | 10 | 0.6 |
| 5.4 | 90 | 0 | 10 | 0.6 |

Method 3

| | |
|---|---|
| Method Name | S |
| Instrument | Agilent 6890N; Column: RXi-5MS 20 m, ID 180 μm, df 0.8 μm |
| Average velocity | 50 cm/s; carrier gas: He |
| Initial temperature | 60° C.; initial time: 1.5 minutes; solvent delay: 1.3 minutes |
| Rate | 50° C./minute; final temperature: 250° C.; final time 3.7 minutes |
| Split ratio | 20:1; injector temperature: 250° C.; injection volume 1 μL |
| Detection | MSD (EI - positive); detection temp.: 280° C.; mass range 50-550 |
| Detection | FID; detector temperature: 300° C. |

Method 4

| | |
|---|---|
| Method Name | SC_ACID.M |
| Column | Waters XSelect CSH C18 (30 × 2.1 mm, 3.5 μm) |
| Flow | 1 mL/minute; column temperature: 35° C. |
| Eluent A | 0.1% formic acid in acetonitrile |
| Eluent B | 0.1% formic acid in water |
| Linear Gradient | t = 0 minutes 5% A; t = 1.6 minutes 98% A; t = 3 minutes 98% A |
| Post-time | 1.3 minutes |
| Detection | DAD (200-320 nm) |
| Detection | PDA (200-400 nm) |
| Detection | MSD (ESI pos/neg) mass range: 100-800 |
| Detection | ELSD (Alltech 3000): gas flow 1.5 mL/minute, gas temp. 40° C. |

It will be apparent to the person skilled in the art that different retention times (RT) may be obtained for LCMS if different analytical conditions are used.

Method 5
Column: X-Bridge C18 Waters 2.1×20 mm, 2.5 μm column
Mobile Phase A: 10 mM ammonium formate in water+0.1% ammonia solution
Mobile Phase B: acetonitrile+5% water+0.1% ammonia solution
Gradient program: Flow rate 1 mL/min

| Time | A % | B % |
|---|---|---|
| 0.00 | 96.00 | 4.00 |
| 4.00 | 5.00 | 95.00 |
| 5.00 | 5.00 | 95.00 |
| 5.10 | 96.00 | 4.00 |

Method 6
Column: X-Bridge C18 Waters 2.1×20 mm, 2.5 μm column
Mobile Phase A: 10 mM ammonium formate in water+0.1% ammonia solution
Mobile Phase B: acetonitrile+5% water+0.1% ammonia solution
Gradient program: Flow rate 1 mL/min

| Time | A % | B % |
|---|---|---|
| 0.00 | 96.00 | 4.00 |
| 1.50 | 5.00 | 95.00 |
| 2.25 | 5.00 | 95.00 |
| 2.50 | 96.00 | 4.00 |

Method 7
Column: X-Bridge C18 Waters 2.1×20 mm, 2.5 μm column
Mobile Phase A: 10 mM ammonium formate in water+0.1% ammonia solution
Mobile Phase B: acetonitrile+5% water+0.1% ammonia solution
Gradient program: Flow rate pump 1: 1 mL/min; Flow rate pump 2: 0.5 mL/min

| Pump 1: | | | Pump 2: | | |
|---|---|---|---|---|---|
| Time | A % | B % | Time | A % | B % |
| 0.00 | 95.10 | 4.90 | 0.10 | 5.00 | 95.00 |
| 4.00 | 5.00 | 95.00 | 1.00 | 5.00 | 95.00 |
| 5.00 | 5.00 | 95.00 | 1.10 | 95.00 | 5.00 |
| 5.10 | 95.10 | 4.90 | | | |

Method 8
Column: Phenomenex Gemini C18, 2.0 mm×50 mm, 3 μm column
Mobile Phase A: 2 mM ammonium bicarbonate
Mobile Phase B: acetonitrile
Gradient program: Flow rate 1.0 mL/minute
Column temperature: 60° C.

| Time | A % | B % |
|---|---|---|
| 0.00 | 99.00 | 1.00 |
| 1.80 | 0.00 | 100.00 |
| 2.10 | 0.00 | 100.00 |
| 2.30 | 99.00 | 1.00 |

Method 9
Column: Waters UPLC® CSH™ C18, 2.1 mm×100 mm, 1.7 μm
Mobile Phase A: 2 mM ammonium bicarbonate modified to pH 10 with ammonium hydroxide
Mobile Phase B: acetonitrile
Gradient program: Flow rate 0.6 mL/minute
Column temperature: 40° C.

| Time | A % | B % |
|---|---|---|
| 0.00 | 95.00 | 5.00 |
| 5.30 | 0.00 | 100.00 |
| 5.80 | 0.00 | 100.00 |
| 5.82 | 95.00 | 5.00 |

Method 10
Column: X-Bridge C18 Waters 2.1×20 mm, 2.5 μm column
Mobile Phase A: 10 mM ammonium formate in water+0.1% formic acid
Mobile Phase B: acetonitrile+5% water+0.1% formic acid
Gradient program: Flow rate pump 1: 1 mL/min; Flow rate pump 2: 0.5 mL/min

| Pump 1: | | | Pump 2: | | |
|---|---|---|---|---|---|
| Time | A % | B % | Time | A % | B % |
| 0.00 | 95.00 | 5.00 | 0.10 | 5.00 | 95.00 |
| 4.00 | 5.00 | 95.00 | 1.00 | 5.00 | 95.00 |
| 5.00 | 5.00 | 95.00 | 1.10 | 95.00 | 5.00 |
| 5.10 | 95.00 | 5.00 | | | |

Method 11
Column: Phenomenex Gemini, C18, 2.0×100 mm, 3 μm
Mobile Phase A: 2 mM ammonium bicarbonate modified to pH 10 with ammonium hydroxide
Mobile Phase B: acetonitrile
Gradient program: Flow rate 0.6 mL/minute
Column temperature: 40° C.

| Time | A % | B % |
|---|---|---|
| 0.00 | 95.00 | 5.00 |
| 5.50 | 0.00 | 100.00 |
| 5.90 | 0.00 | 100.00 |
| 5.92 | 95.00 | 5.00 |

Method 12
Column: Waters Acquity UPLC BEH, C18, 2.1×50 mm, 1.7 μm
Mobile Phase A: 10 mM ammonium formate in water+0.1% formic acid
Mobile Phase B: acetonitrile+5% water+0.1% formic acid
Gradient program: Flow rate 0.7 mL/minute

| Time | A % | B % |
|---|---|---|
| 0.00 | 98.00 | 2.00 |
| 4.00 | 5.00 | 95.00 |
| 5.00 | 5.00 | 95.00 |
| 5.10 | 98.00 | 2.00 |

Method 13
Column: Waters Acquity UPLC BEH, C18, 2.1×50 mm, 1.7 μm
Mobile Phase A: 10 mM ammonium formate in water+0.1% ammonia solution
Mobile Phase B: acetonitrile+5% water+0.1% ammonia solution
Gradient program: Flow rate 0.7 mL/minute

| Time | A % | B % |
|---|---|---|
| 0.00 | 98.00 | 2.00 |
| 4.00 | 5.00 | 95.00 |
| 5.00 | 5.00 | 95.00 |
| 5.10 | 98.00 | 2.00 |

Preparative HPLC-MS
Method 1
Waters Fraction-Lynx system, with 2545 pump, 2998 PDA, 2767 fraction collector and a Waters 3100 MS.
pH3_35_50 focused gradient, reverse phase.
Waters XBridge Prep C18 OBD column, 19×100 mm, 5 μm.
Solvent A: 10 mM ammonium bicarbonate+0.1% formic acid
Solvent B: acetonitrile+0.1% formic acid

| Time (min) | % A | % B |
|---|---|---|
| 0 | 90 | 10 |
| 2.3 | 65 | 35 |
| 11 | 50 | 50 |
| 11.5 | 5 | 95 |
| 13 | 5 | 95 |
| 13.2 | 90 | 10 |

Flow rate: 19 mL/minute (+1 mL/minute acetonitrile ACD)
Column temperature: ambient
Method 2
Waters Fraction-Lynx system, with 2545 pump, 2998 PDA, 2767 fraction collector and a Waters 3100 MS.
pH10_35_30 focused gradient, reverse phase.
Waters XBridge Prep C18 OBD column, 19×100 mm, 5 μm.
Solvent A: 10 mM ammonium bicarbonate+0.1% $NH_4OH$
Solvent B: acetonitrile+0.1% $NH_4OH$

| Time (min) | % A | % B |
|---|---|---|
| 0 | 90 | 10 |
| 2.3 | 65 | 35 |
| 11 | 50 | 50 |
| 11.5 | 5 | 95 |
| 13 | 5 | 95 |
| 13.2 | 90 | 10 |

Flow rate: 19 mL/minute (+1 mL/minute acetonitrile ACD)
Column temperature: ambient
Method 3
pH10 35_50 gradient, reverse phase
Column: XBridge Prep Phenyl, 5 μm OBD, 19×150 mm
Solvent A: 10 mM ammonium bicarbonate in water+0.1% ammonia solution
Solvent B: acetonitrile+5% water+0.1% ammonia solution

| Time | A % | B % |
|---|---|---|
| 0.00 | 65.00 | 35.00 |
| 2.50 | 65.00 | 35.00 |
| 11.00 | 50.00 | 50.00 |
| 11.50 | 5.00 | 95.00 |
| 13.00 | 65.00 | 35.00 |

Flow rate: 19 mL/minute
Method 4
Waters UV system with 2996 PDA
Column: Lux Cellulose-1, 21.2×250 mm, 5 μm column
Run time: 40 minutes, isocratic gradient
Solvent: 100% MeOH (+0.1% $NH_4OH$)
Flow rate: 10 mL/minute
Column temperature: 40° C., run time 40 minutes
Method 5
pH10 25_40 gradient, reverse phase
Column: XBridge Prep C18, 5 μm OBD, 19×100 mm
Mobile Phase A: 10 mM ammonium bicarbonate in water+0.1% ammonia solution
Mobile Phase B: acetonitrile+5% water+0.1% ammonia solution

| Time | A % | B % |
|---|---|---|
| 0.00 | 75.00 | 25.00 |
| 2.50 | 75.00 | 25.00 |
| 11.00 | 60.00 | 40.00 |

-continued

| Time | A % | B % |
| --- | --- | --- |
| 11.50 | 5.00 | 95.00 |
| 13.00 | 75.00 | 25.00 |

Flow rate: 19 mL/minute
Method 6
Column: XBridge™ Prep C18, 10 μm OBD™, 30×100 mm
Mobile Phase: 30-95% acetonitrile (0.2% ammonium hydroxide) in water (0.2% ammonium hydroxide) over 10 minutes
UV: 215 and 254 nm
Flow Rate: 40 mL/minute Intermediate 1

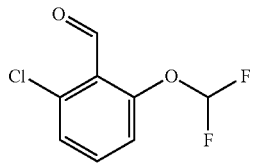 [SMILES: O=Cc1c(Cl)cccc1OC(F)F]

2-Chloro-6-(difluoromethoxy)benzaldehyde

To 2-chloro-6-hydroxybenzaldehyde (20 g, 128.2 mmol) in acetonitrile (150 mL) was added a solution of potassium hydroxide (71.7 g, 1282 mmol) in water (50 mL) at 0° C. The reaction mixture was stirred at 0° C. for 10 minutes, then diethyl (bromodifluoromethyl)phosphonate (36.4 mL, 205.1 mmol) was added at 0° C. The reaction mixture was stirred at 0° C. for 30 minutes, then poured into water (500 mL). The aqueous layer was extracted with EtOAc (2×1 L). The organic layer was washed with water (500 mL) and brine (500 mL), then dried over anhydrous sodium sulphate and filtered. The organic layers were evaporated under reduced pressure. The resulting crude residue was purified by column chromatography (SiO$_2$, 5% EtOAc in hexane) yielding the title compound (13.9 g, 53%) as a yellow oil. $\delta_H$ (400 MHz, CDCl$_3$) 10.46 (s, 1H), 7.49 (t, J 8.2 Hz, 1H), 7.37 (dd, J 8.1, 1.1 Hz, 1H), 7.20 (m, 1H), 6.61 (t, 1H).

Intermediate 2

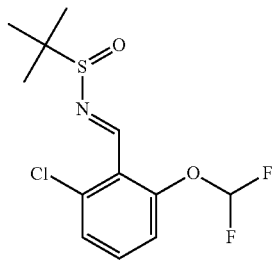 [SMILES: CC(C)(C)S(=O)/N=C/c1c(Cl)cccc1OC(F)F]

N-{[2-Chloro-6-(difluoromethoxy)phenyl]methylene}-(S)-2-methylpropane-2-sulfinamide To a solution of Intermediate 1 (20 g, 97.08 mmol) in dry THF (100 mL) at 0° C. were added (S)-(−)-tert-butylsulfinamide (12.92 g, 106.79 mmol), K$_3$PO$_4$ (61.73 g, 291.2 mmol) and K$_2$HPO$_4$ (50.6 g, 291.2 mmol). The reaction mixture was stirred at r.t. for 18 h, then filtered through celite and washed with EtOAc (1 L). The organic layer was washed with water (500 mL) and brine (500 mL), then dried over anhydrous sodium sulphate. The organic layer was filtered and evaporated under reduced pressure, then the residue was purified by column chromatography (SiO$_2$, 10% EtOAc in hexane), to afford the title compound (20 g, 87%) as a yellow oil. $\delta_H$ (400 MHz, CDCl$_3$) 8.90 (s, 1H), 7.45-7.32 (m, 2H), 7.29-7.15 (m, 1H), 6.82-6.34 (m, 1H), 1.29 (s, 9H). LCMS (ES+) 309.90 (M+H)$^+$, RT 2.73 minutes.

Intermediate 3

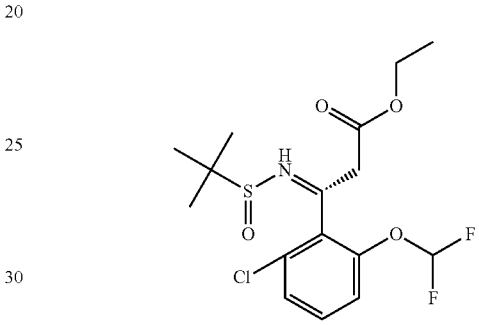

Ethyl (3R)-3-{[(S)-tert-butylsulfinyl]amino}-3-[2-chloro-6-(difluoromethoxy)phenyl]propanoate Zinc powder (150 g) was taken up in 1N aqueous HCl solution (500 mL), stirred for 10 minutes and decanted. The zinc dust powder was washed with water (3×500 mL) and decanted. The powder was further washed with acetone (3×500 mL), decanted and dried under vacuum. To the resulting activated zinc dust (105 g, 1618 mmol) in dry THF (150 mL) was added CuCl (19.2 g, 194 mmol) and the reaction mixture was heated under reflux for 30 minutes. The reaction mixture was cooled to room temperature and ethyl bromoacetate (45 mL, 404 mmol) in THF (100 mL) was added dropwise. The reaction mixture was stirred at 50° C. for 30 minutes. The reaction mixture was cooled to 0° C. and Intermediate 2 (50 g, 161 mmol) in THF (100 mL) was added. The reaction mixture was warmed to r.t. and stirred for 3 h, then filtered through celite and washed with EtOAc (700 mL). The organic layer was washed with 1N citric acid (500 mL), saturated aqueous sodium bicarbonate solution (500 mL), water (500 mL) and brine (500 mL). The organic layers were separated and dried over anhydrous sodium sulphate, then filtered and evaporated under reduced pressure. The residue was purified by chromatography (SiO$_2$, 40% EtOAc in hexane) to afford the title compound (59 g, 92%) as a yellow oil. $\delta_H$ (400 MHz, CDCl$_3$) 7.29-7.21 (m, 2H), 7.05 (d, J 7.3 Hz, 1H), 6.82-6.34 (m, 1H), 5.59 (m, 1H), 4.36 (s, 1H), 4.18-4.02 (m, 2H), 3.25 (dd, J 15.6, 7.5 Hz, 1H), 3.01 (dd, J 15.3, 7.5 Hz, 1H), 1.31-1.11 (m, 12H).

Intermediate 4

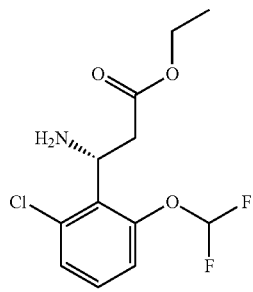 [SMILES: CCOC(=O)C[C@@H](N)c1c(Cl)cccc1OC(F)F]

Ethyl (3R)-3-amino-3-[2-chloro-6-(difluoromethoxy)phenyl]propanoate hydrochloride To a solution of Intermediate 3 (32 g, 80.6 mmol) in a diethyl ether:ethanol mixture (2:1, 75 mL) was added 4M HCl in 1,4-dioxane (70 mL). The reaction mixture was stirred at r.t. for 1 h, then concentrated under reduced pressure. The residue was triturated with diethyl ether (500 mL) to afford the title compound (22 g, 93%) as a yellow solid. δ$_H$ (400 MHz, CDCl$_3$) 8.93 (d, J 6.2 Hz, 2H), 7.32-7.10 (m, 3H), 6.96 (s, 1H), 5.42 (m, 1H), 4.08 (q, J 7.0 Hz, 2H), 3.36 (dd, J 16.5, 7.0 Hz, 1H), 3.14 (dd, J 16.5, 7.8 Hz, 1H), 1.34 (t, J 7.1 Hz, 3H).

Intermediate 5

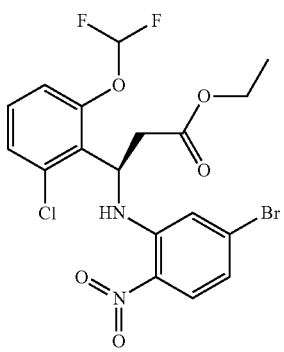 [SMILES: CCOC(=O)C[C@@H](Nc1cc(Br)ccc1[N+](=O)[O-])c1c(Cl)cccc1OC(F)F]

Ethyl (3R)-3-(5-bromo-2-nitroanilino)-3-[2-chloro-6-(difluoromethoxy)phenyl]propanoate To a solution of Intermediate 4 (9.3 g, 28.3 mmol) in acetonitrile (80 mL) were added potassium carbonate (11.73 g, 84.9 mmol) and 4-bromo-2-fluoro-1-nitrobenzene (7.4 g, 34 mmol). The reaction mixture was stirred at 80° C. overnight, then diluted with EtOAc (150 mL) and washed with water (150 mL). The organic layer was separated and dried over anhydrous sodium sulphate, then filtered and concentrated under reduced pressure. The residue was purified by chromatography (SiO$_2$, 10% EtOAc in hexane) to afford the title compound (12.5 g, 90%) as a yellow oil. LCMS Method 1 (ES+) 493 (M+H)$^+$.

Intermediate 6

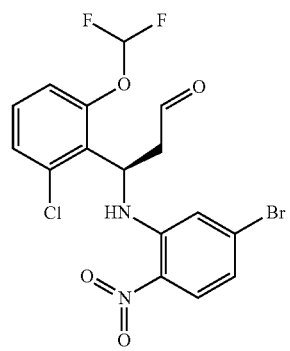 [SMILES: O=CC[C@@H](Nc1cc(Br)ccc1[N+](=O)[O-])c1c(Cl)cccc1OC(F)F]

(3R)-3-(5-Bromo-2-nitroanilino)-3-[2-chloro-6-(difluoromethoxy)phenyl]propanal

To a solution of Intermediate 5 (12.5 g, 25.4 mmol) in THF (130 mL) at −78° C. was added DIBAL-H (50.8 mL, 50.8 mmol) dropwise. The reaction mixture was stirred for 2 h at −78° C., then quenched with aqueous ammonium chloride solution. The reaction mixture was diluted with EtOAc and filtered through celite. The filtrate was washed with water. The organic layer was separated and dried over sodium sulphate, then filtered and evaporated under reduced pressure. The crude material was purified by chromatography (SiO$_2$, 15% EtOAc in hexane) to give the title compound (9.0 g, 80%) as a yellow oil. δ$_H$ (400 MHz, CDCl$_3$) 9.80 (d, J 1.3 Hz, 1H), 8.78 (d, J 9.0 Hz, 1H), 7.99 (d, J 9.0 Hz, 1H), 7.27 (d, J 3.2 Hz, 2H), 7.21-7.08 (m, 1H), 6.81-6.66 (m, 2H), 5.93 (m, 1H), 3.56-3.38 (m, 2H), 3.12 (dd, J 17.9, 5.2 Hz, 1H).

Intermediate 7

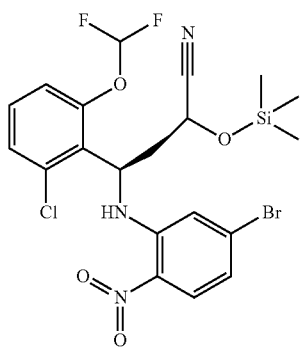 [SMILES: C[Si](C)(C)OC(C#N)C[C@@H](Nc1cc(Br)ccc1[N+](=O)[O-])c1c(Cl)cccc1OC(F)F]

(4R)-4-(5-Bromo-2-nitroanilino)-4-[2-chloro-6-(difluoromethoxy)phenyl]-2-(trimethylsilyloxy)butanenitrile To a solution of Intermediate 6 (9.0 g, 20 mmol) in DCM (150 mL) were added ZnI$_2$ (0.64 g, 2 mmol), triethylamine (0.28 mL, 2 mmol) and trimethylsilyl cyanide (5.0 mL, 40 mmol). The reaction mixture was stirred at r.t. for 2 h, then water (200 mL) was added and the mixture was extracted with DCM (500 mL). After evaporation of the organic layer, the title compound (9.0 g, crude material) was obtained as a yellow oil, which was utilised without additional purification.

Intermediate 8

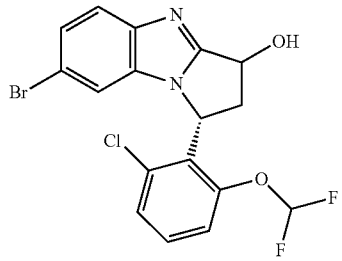 [SMILES: OC1C[C@H](c2c(Cl)cccc2OC(F)F)n2c1nc1ccc(Br)cc12]

(1R)-7-Bromo-1-[2-chloro-6-(difluoromethoxy)phenyl]-2,3-dihydro-1H-pyrrolo[1,2-a]benzimidazol-3-ol To a solution of Intermediate 7 (9 g, 16.4 mmol) in EtOH (150 mL) was added $SnCl_2$ (15.6 g, 82 mmol). The reaction mixture was heated at 80° C. for 2 h, then quenched with water and basified to pH 8 using 1N KOH. The reaction mixture was diluted with EtOAc and filtered through celite. The organic layer was washed with water and brine, then dried over anhydrous sodium sulphate, filtered and concentrated under reduced pressure. The residue was purified by chromatography ($SiO_2$, 60% EtOAc in hexane), then triturated with hexane:EtOAc, to yield the title compound (3.0 g, 43%) as a yellow solid. LCMS Method 1 (ES+) 431 ($Br^{81}/Cl^{35}$ and/or $Br^{79}/Cl^{37}$) $(M+H)^+$.

Intermediates 9 & 10

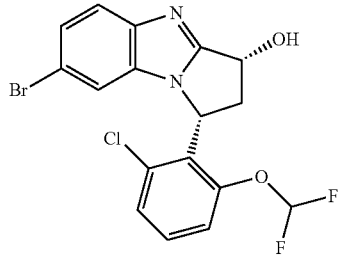

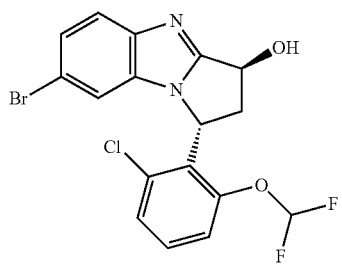

Intermediate 9

(1R,3R)-7-Bromo-1-[2-chloro-6-(difluoromethoxy)phenyl]-2,3-dihydro-1H-pyrrolo[1,2-a]benzimidazol-3-ol

Intermediate 10

(1R,3S)-7-Bromo-1-[2-chloro-6-(difluoromethoxy)phenyl]-2,3-dihydro-1H-pyrrolo[1,2-a]benzimidazol-3-ol Intermediate 8 (12.5 g) was subjected to preparative SFC chromatography under the following conditions: Chiracel OD column (column size: 50×266 mm, flow: 360 mL/minute, injection: 20 mg, frequency: 4 minutes, 25° C., $CO_2$+20% MeOH).

The peaks thus separated were analysed under the following analytical conditions: Chiralcel OD-H (column size: 250×4.6 mm, flow 1 mL/minute at 30° C. using 100% methanol containing 0.1% DEA).

Intermediate 9 (3.63 g, 29%) was isolated as the third-eluting diastereomer (RT 5.4 minutes). $\delta_H$ (400 MHz, DMSO-$d_6$) 7.57 (m, 2.3H), 7.45 (m, 0.8H), 7.35 (d, J 8.0 Hz, 0.6H), 7.26 (m, 1H), 7.17 (m, 0.3H), 6.83 (t, J 72.5 Hz, 1H), 6.69 (br s, 1H), 6.15 (m, 1H), 6.07 (m, 1H), 5.38 (m, 1H), 3.38 (m, 1H), 2.67 (m, 1H) as a 7:3 mixture of rotamers. LCMS Method 2 (ES+) 429.1/431.1/433.1 $(M+H)^+$, RT 4.31 minutes.

The second-eluting diastereomers (RT 4.7 minutes) were collected and subjected to preparative SFC chromatography under the following conditions: Whelko 01 (R,R) column (column size: 50×227 mm, flow: 360 mL/minute, injection: 690 mg, frequency: 5.5 minutes, 25° C., $CO_2$+20% EtOH).

The peaks thus separated were analysed under the following analytical conditions: Chiralcel OD-H (column size: 250×4.6 mm, flow: 1 mL/minute at 30° C. using 50:50 heptane/isopropyl alcohol containing 0.1% DEA).

The second eluting diastereomer (RT 5.9 minutes) gave Intermediate 10 (4.46 g, 36%), after evaporation of the combined fractions. $\delta_H$ (400 MHz, DMSO-$d_6$) 7.55 (m, 3.4H), 7.31 (m, 1.4H), 7.12 (d, J 7.8 Hz, 0.6H), 7.03 (t, J 73.0 Hz, 0.6H), 6.89 (s, 0.6H), 6.81 (s, 0.4H), 6.32 (dd, J 8.4, 5.9 Hz, 1H), 6.10 (d, J 6.6 Hz, 1H), 5.32 (m, 0.6H), 5.26 (t, J 6.9 Hz, 0.4H), 3.13 (m, 1H), 2.93 (m, 1H) as a 6:4 mixture of rotamers. LCMS Method 2 (ES+) 429.1/431.1/433.1 $(M+H)^+$, RT 4.40 minutes.

Intermediate 10

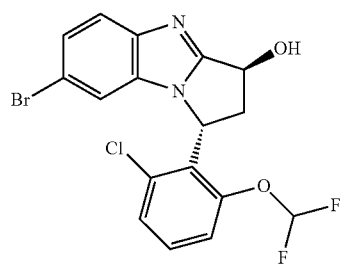 [SMILES: O[C@H]1C[C@H](c2c(Cl)cccc2OC(F)F)n2c1nc1ccc(Br)cc12]

(1R,3S)-7-Bromo-1-[2-chloro-6-(difluoromethoxy)phenyl]-2,3-dihydro-1H-pyrrolo[1,2-a]benzimidazol-3-ol—Alternative Procedure Intermediate 9 (3.63 g, 8.45 mmol) and triphenylphosphine (2.66 g, 10.14 mmol) were solubilized in anhydrous THF (34 mL), under an inert atmosphere of nitrogen. Acetic acid (0.5 mL, 9.30 mmol) was added and the mixture was cooled to 0° C. A solution of DIAD (2.62 mL, 12.62 mmol) in anhydrous THF (5 mL) was added dropwise. The reaction mixture was slowly warmed to r.t. and maintained for 2 h at r.t. The reaction mixture was diluted with EtOAc and washed with saturated aqueous NaHCO$_3$ solution. The organic layer was dried over anhydrous magnesium sulfate, then filtered and concentrated under vacuum. The resulting material (3.6 g) was solubilized in MeOH (40 mL). Potassium carbonate (1.1 g, 8.48 mmol) was added and the reaction mixture was stirred for 1 h at r.t. The solvent was evaporated, then the residue was taken up in EtOAc (50 mL) and water (20 mL). The organic layer was washed with water (2×20 mL) and dried over anhydrous sodium sulfate, then filtered and concentrated under vacuum, to give the title compound (4.9 g, crude) as a brown oil, which was utilised without further purification. LCMS Method 1 (ES$^+$) 429/431/433 (M+H)$^+$, RT 2.46 minutes.

Intermediate 11

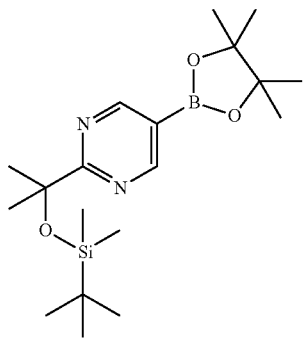 [SMILES: CC(C)(O[Si](C)(C)C(C)(C)C)c1ncc(B2OC(C)(C)C(C)(C)O2)cn1]

tert-Butyl(dimethyl){1-methyl-1-[5-(4,4,5,5-tetramethyl-1,3,2-dioxaborolan-2-yl)pyrimidin-2-yl]ethoxy}silane 2-(1-Hydroxy-1-methylethyl)pyrimidine-5-boronic acid pinacol ester (10 g, 37.9 mmol), tert-butyldimethylchlorosilane (11.76 g, 75.7 mmol) and imidazole (7.89 g, 115.9 mmol) were dissolved in anhydrous DMF (150 mL). The reaction mixture was stirred at 85° C. for 4 days. EtOAc (100 mL) and water (250 mL) were added, then the aqueous layer was extracted with EtOAc (3×50 mL). The combined organic layers were washed with brine (3×20 mL) and dried over anhydrous magnesium sulfate, then filtered and concentrated in vacuo. The residue was purified by chromatography (SiO$_2$, 0-100% EtOAc in heptane) to afford the title compound (12.0 g, 84%) as a transparent oil. $\delta_H$ (400 MHz, CDCl$_3$) 9.04 (s, 2H), 1.70 (s, 6H), 1.40 (s, 12H), 0.94 (s, 9H), 0.01 (s, 6H).

Intermediate 12

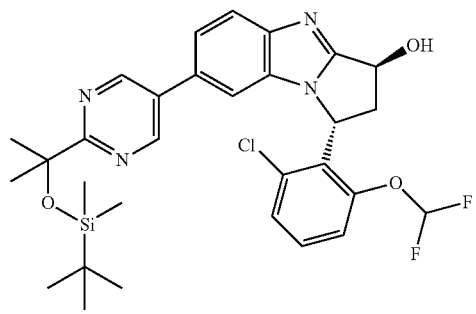 [SMILES: CC(C)(O[Si](C)(C)C(C)(C)C)c1ncc(-c2ccc3nc4n(c3c2)[C@@H](c2c(Cl)cccc2OC(F)F)C[C@@H]4O)cn1]

(1R,3S)-7-(2-{1-[tert-Butyl(dimethyl)silyl]oxy-1-methylethyl}pyrimidin-5-yl)-1-[2-chloro-6-(difluoromethoxy)phenyl]-2,3-dihydro-1H-pyrrolo[1,2-a]benzimidazol-3-ol Intermediate 10 (4.46 g, 10.4 mmol), Intermediate 11 (3.92 g, 10.4 mmol) and cesium carbonate (5.07 g, 15.6 mmol) were placed in a tube, which was filled with argon. Degassed 1,4-dioxane (37 mL) and degassed water (3.7 mL) were added and the resulting slurry was stirred at r.t. for 5 minutes before the addition of [1,1'-bis(diphenylphosphino)ferrocene]dichloropalladium(II) (380 mg, 0.52 mmol). The reaction mixture was placed on a pre-heated stirring plate at 90° C. and stirred at this temperature for 2 h. The reaction mixture was cooled to r.t. before the addition of EtOAc (50 mL) and water (50 mL). The aqueous layer was extracted with EtOAc (3×20 mL), then the combined organic layers were dried over anhydrous magnesium sulfate, filtered and concentrated under reduced pressure. The crude residue was purified by chromatography (SiO$_2$, 30-100% EtOAc in hexane) to yield the title compound (5.7 g, 92%). LCMS Method 2 (ES+) 601.3/603.2 (M+H)$^+$, RT 3.64 minutes.

Intermediate 13

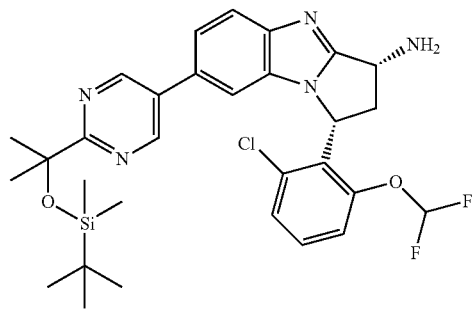 [SMILES: CC(C)(O[Si](C)(C)C(C)(C)C)c1ncc(-c2ccc3nc4n(c3c2)[C@@H](c2c(Cl)cccc2OC(F)F)C[C@H]4N)cn1]

(1R,3R)-7-(2-{1-[tert-Butyl(dimethyl)silyl]oxy-1-methylethyl}pyrimidin-5-yl)-1-[2-chloro-6-(difluoromethoxy)phenyl]-2,3-dihydro-1H-pyrrolo[1,2-a]benzimidazol-3-amine Intermediate 12 (11.18 g, 18.63 mmol) was suspended in dry toluene (34 mL). Diphenylphosphoryl azide (5.0 mL, 24.22 mmol) was added at 0° C., followed by the addition of 1,8-diazabicyclo[5.4.0]undec-7-ene (3.62 mL, 24.22 mmol). The reaction mixture was allowed to reach r.t. and stirred at r.t. for 2 h, then heated at 50° C. for 18 h. The reaction mixture was diluted with water (100 mL) and EtOAc (100 mL). The aqueous layer was extracted with EtOAc (3×100 mL). The combined organic layers were washed with saturated aqueous NH₄Cl solution and saturated aqueous NaHCO₃ solution, then dried over anhydrous magnesium sulfate, filtered and concentrated under vacuum. The crude residue was dissolved in a mixture of THF (172 mL) and water (17 mL) before the addition of a solution of trimethylphosphine in toluene (1M, 34.6 mL, 20.8 mmol). The reaction mixture was stirred at r.t. for 2 h. The solvents were evaporated and the residue was purified by chromatography (SiO₂, 0-5% MeOH in DCM, 1% NH₃) to afford the title compound (7.0 g, 61%). LCMS Method 1 (ES+) 600.3/602.3 (M+H)⁺, RT 3.49 minutes.

Intermediate 14

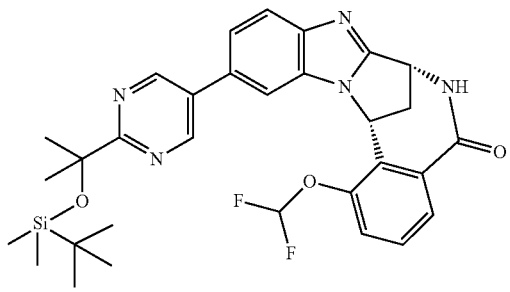 [SMILES: CC(C)(O[Si](C)(C)C(C)(C)C)c1ncc(-c2ccc3nc4n(c3c2)[C@@H]2C[C@H]4NC(=O)c3cccc(OC(F)F)c32)cn1]

(7R,14R)-11-[2-(2-{[tert-Butyl(dimethyl)silyl]oxy}propan-2-yl)pyrimidin-5-yl]-1-(difluoromethoxy)-6,7-dihydro-7,14-methanobenzimidazo[1,2-b][2,5]benzodiazocin-5(14H)-one Intermediate 13 (7.00 g, 7.93 mmol), sodium carbonate (6.18 g, 58.3 mmol) and dichloro[1,3-bis(dicyclohexylphosphino)propane]palladium(II) (Pd-133 from Johnson Matthey) (1.43 g, 0.25 mmol) were suspended in degassed (nitrogen) 1,4-dioxane (95 mL). The reaction mixture was heated overnight at 150° C. under 5 atmospheres of CO gas. The reaction mixture was filtered over celite, which was thoroughly washed with ethanol. The volatiles were removed in vacuo, and the residue was purified by chromatography (SiO₂, 50-100% EtOAc in heptane), to afford the title compound (3.2 g, 62%) as a white solid. δ_H (400 MHz, DMSO-d₆) 9.23 (d, J 6.8 Hz, 1H), 9.16 (s, 2H), 8.32 (dd, J 5.9, 3.5 Hz, 1H), 7.88 (dd, J 51.9, 43.2 Hz, 1H), 7.84 (s, 1H), 7.71 (dd, J 8.3, 1.8 Hz, 1H), 7.60 (m, 3H), 6.47 (d, J 7.1 Hz, 1H), 4.99 (t, J 6.8 Hz, 1H), 3.58 (m, 1H), 2.85 (d, J 13.4 Hz, 1H), 1.76 (s, 6H), 0.95 (s, 9H), 0.01 (s, 6H). LCMS Method 1 (ES+) 592.3 (M+H)⁺, RT 3.43 minutes.

Intermediate 15

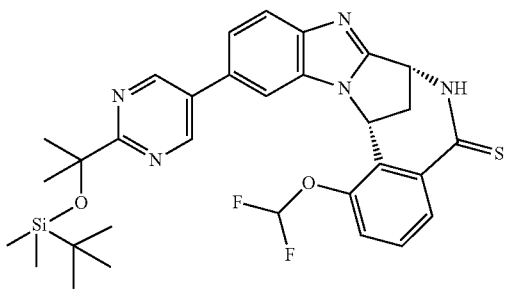 [SMILES: CC(C)(O[Si](C)(C)C(C)(C)C)c1ncc(-c2ccc3nc4n(c3c2)[C@@H]2C[C@H]4NC(=S)c3cccc(OC(F)F)c32)cn1]

(7R,14R)-11-[2-(2-{[tert-Butyl(dimethyl)silyl]oxy}propan-2-yl)pyrimidin-5-yl]-1-(difluoromethoxy)-6,7-dihydro-7,14-methanobenzimidazo[1,2-b][2,5]benzodiazocine-5(14H)-thione Intermediate 14 (150 mg, 0.25 mmol) was dissolved in toluene (6 mL) before the addition of Lawesson's reagent (114 mg, 0.28 mmol). The slurry was heated overnight at 120° C. The reaction mixture was concentrated in vacuo. The residue was dissolved in DCM and filtered through a pad of silica gel, eluting with DCM/MeOH (1:1). Removal of the volatiles in vacuo afforded the title compound (195 mg) as a brown solid, which was utilised without further purification. LCMS Method 2 (ES+) 608 (M+H)⁺, RT 3.74 minutes.

Intermediate 16

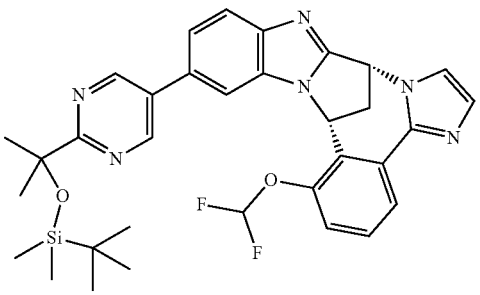 [SMILES: CC(C)(O[Si](C)(C)C(C)(C)C)c1ncc(-c2ccc3nc4n(c3c2)[C@@H]2C[C@H]4n3ccnc3-c3cccc(OC(F)F)c32)cn1]

(8R,15R)-11-[2-(2-{[tert-Butyl(dimethyl)silyl]oxy}propan-2-yl)pyrimidin-5-yl]-7-(difluoromethoxy)-8H,15H-8,15-methanobenzimidazo[2,1-d]imidazo[2,1-a][2,5]benzodiazocine Intermediate 15 (30 mg, 0.049 mmol), p-toluenesulfonic acid monohydrate (0.4 mg, 0.002 mmol), aminoacetaldehyde diethyl acetal (66 mg, 0.49 mmol) and 1-butanol (0.4 mL) were placed into a 10 mL microwave tube. The mixture was heated under microwave irradiation at 180° C. for 1 h. The reaction mixture was allowed to cool to r.t. and the solvent was removed under reduced pressure. The crude residue was purified by preparative HPLC-MS (acidic conditions). The resulting material was diluted with EtOAc (2 mL) and saturated aqueous NaHCO₃ solution (1 mL). The two phases were separated and the aqueous layer was further extracted with EtOAc (3×2 mL). The combined organic layers were dried over anhydrous magnesium sulphate, then filtered and concentrated under reduced pressure, to afford the title compound (10 mg, 33%) as a beige solid. LCMS Method 4 (ES+) 615 (M+H)+, RT 3.54 minutes.

Intermediate 17

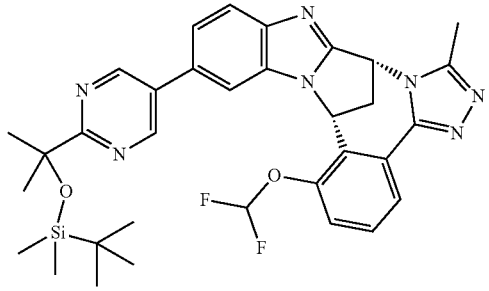 [SMILES: Cc1nnc2n1[C@@H]1C[C@H](c3c(OC(F)F)cccc3-2)n2c1nc1ccc(-c3cnc(C(C)(C)O[Si](C)(C)C(C)(C)C)nc3)cc12]

(8R,15R)-11-[2-(2-{[tert-Butyl(dimethyl)silyl]oxy}propan-2-yl)pyrimidin-5-yl]-7-(difluoromethoxy)-1-methyl-8H,15H-8,15-methanobenzimidazo[2,1-d][1,2,4]triazolo[3,4-a][2,5]benzodiazocine To a suspension of Intermediate 15 (92.4 mg, 0.152 mmol) and 4 Å molecular sieve (46 mg) in 1-butanol (0.7 mL) was added acetylhydrazine (0.13 mL, 1.52 mmol). The reaction mixture was stirred at 140° C. overnight, then diluted with DCM (2 mL) and water (1 mL). The layers were separated and the aqueous layer was further extracted with DCM (2×2 mL). The combined organic layers were dried over anhydrous magnesium sulphate, filtered and concentrated under reduced pressure. The crude residue was purified by basic reverse phase preparative LCMS, to give the title compound (42 mg, 44%). LCMS Method 3 (ES+) 630.2 (M+H)+, RT 3.21 minutes. LCMS Method 4 (ES+) 630 (M+H)+, RT 3.64 minutes.

Intermediate 18

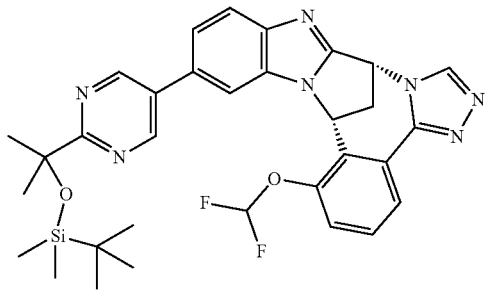 [SMILES: CC(C)(O[Si](C)(C)C(C)(C)C)c1ncc(-c2ccc3nc4n(c3c2)[C@@H]2C[C@H]4n3cnnc3-c3cccc(OC(F)F)c32)cn1]

(8R,15R)-11-[2-(2-{[tert-Butyl(dimethyl)silyl]oxy}propan-2-yl)pyrimidin-5-yl]-7-(difluoromethoxy)-8H,15H-8,15-methanobenzimidazo[2,1-d][1,2,4]triazolo[3,4-a][2,5]benzodiazocine To a suspension of Intermediate 15 (308 mg, 0.51 mmol) and 4 Å molecular sieve (152 mg) in 1-butanol (2 mL) was added formylhydrazine (0.35 mL, 5.1 mmol). The reaction mixture was stirred at 140° C. overnight, then diluted with DCM (2 mL) and water (2 mL). The layers were separated and the organic layer was further washed with 0.1N HCl (1 mL), saturated aqueous NaHCO3 solution (1 mL) and brine, then dried over anhydrous magnesium sulphate, filtered and concentrated under reduced pressure. The crude material was purified by column chromatography (SiO2, 6% MeOH/DCM) to give the title compound (94 mg, 30%). LCMS Method 3 (ES+) 616 (M+H)+, RT 5.67 minutes.

Intermediate 19

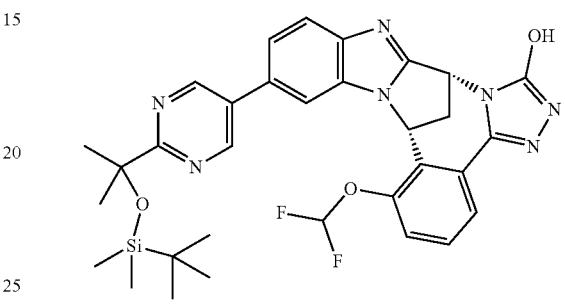

(8R,15R)-11-[2-(2-{[tert-Butyl(dimethyl)silyl]oxy}propan-2-yl)pyrimidin-5-yl]-7-(difluoromethoxy)-8H,15H-8,15-methanobenzimidazo[2,1-d][1,2,4]triazolo[3,4-a][2,5]benzodiazocin-1-ol To a suspension of Intermediate 15 (141 mg, 0.23 mmol) and 4 Å molecular sieves (70 mg) in 1-butanol (2 mL) was added methyl N-aminocarbamate (0.24 mL, 2.32 mmol). The reaction mixture was stirred at 140° C. overnight, then filtered through celite and rinsed with EtOAc (2 mL). The filtrate was washed with water (1 mL). The aqueous layer was back-extracted with EtOAc (2 mL). The combined organic extracts were dried over anhydrous magnesium sulphate, filtered and concentrated under reduced pressure. The crude residue was purified by preparative LCMS (basic, Method 2) to give the title compound (38 mg, 26%). LCMS Method 3 (ES+) 632 (M+H)+, RT 3.41 minutes.

Intermediate 20

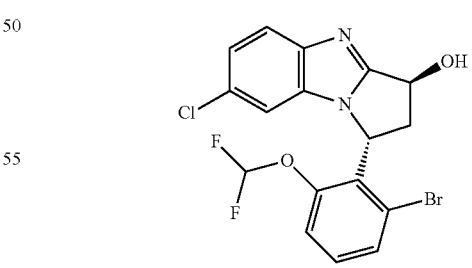

(1R,3S)-7-Chloro-1-[2-bromo-6-(difluoromethoxy)phenyl]-2,3-dihydro-1H-pyrrolo[1,2-a]benzimidazol-3-ol Prepared in a sequence of steps analogous to those described for Intermediates 2 to 10 starting from 2-bromo- 6-(difluoromethoxy)benzaldehyde and utilising 4-chloro-2-fluoro-1-nitrobenzene instead of 4-bromo-2-fluoro-1-nitrobenzene.

Intermediate 21

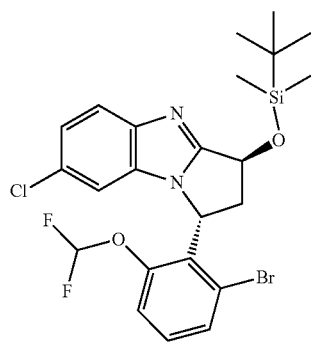 [SMILES: CC(C)(C)[Si](C)(C)O[C@H]1C[C@H](c2c(Br)cccc2OC(F)F)n2c1nc1ccc(Cl)cc12]

{(1R,3S)-1-[2-Bromo-6-(difluoromethoxy)phenyl]-7-chloro-2,3-dihydro-1H-pyrrolo[1,2-a]benzimidazol-3-yl}oxy(tert-butyl)dimethylsilane To a solution of Intermediate 20 (20 g, 46.55 mmol) in DMF (120 mL) were added successively imidazole (3.96 g, 58.2 mmol) and tert-butyldimethylchlorosilane (8.32 g, 53.5 mmol). The reaction mixture was stirred at r.t. overnight. Water (200 mL) was added, and the reaction mixture was extracted with diethyl ether (3×100 mL). The combined organic layers were washed with brine (100 mL) and dried over anhydrous magnesium sulphate, then filtered and concentrated in vacuo, to afford the title compound (25.2 g, 99%) as a white solid. LCMS Method 3 (ES+) 543/545/547 (M+H)$^+$, RT 3.47 minutes.

Intermediate 22

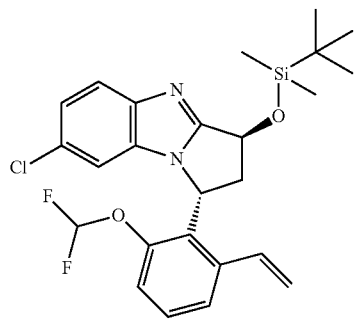 [SMILES: C=Cc1cccc(OC(F)F)c1[C@H]1C[C@H](O[Si](C)(C)C(C)(C)C)c2nc3ccc(Cl)cc3n21]

tert-Butyl({(1R,3S)-7-chloro-1-[2-(difluoromethoxy)-6-vinylphenyl]-2,3-dihydro-1H-pyrrolo[1,2-a]benzimidazol-3-yl}oxy)(dimethyl)silane To a suspension of Intermediate 21 (1.07 g, 1.97 mmol), potassium vinyltrifluoroborate (385 mg, 2.76 mmol) and cesium carbonate (1.29 g, 3.95 mmol) in a degassed mixture of 1,4-dioxane (18 mL) and water (2 mL) was added [1,1'-bis(diphenylphosphino)ferrocene]palladium(II) dichloride dichloromethane complex (81 mg, 0.1 mmol).

The reaction mixture was heated at 110° C. for 16 h, then filtered through celite, rinsed with EtOAc and concentrated in vacuo. The residue was taken up in EtOAc, washed with water and brine, dried over anhydrous magnesium sulphate, filtered and concentrated to dryness. The crude material was purified by column chromatography (SiO$_2$, 10-20% EtOAc in heptane) to give the title compound (869 mg, 78%) as a white solid. LCMS Method 3 (ES+) 491 (M+H)$^+$, RT 3.55 minutes.

Intermediate 23

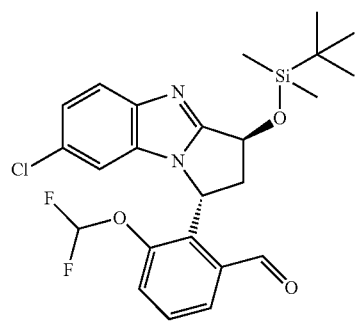 [SMILES: CC(C)(C)[Si](C)(C)O[C@H]1C[C@H](c2c(C=O)cccc2OC(F)F)n2c1nc1ccc(Cl)cc12]

2-{(1R,3S)-3-[tert-Butyl(dimethyl)silyl]oxy-7-chloro-2,3-dihydro-1H-pyrrolo[1,2-a]benzimidazol-1-yl]-3-(difluoromethoxy)benzaldehyde To a solution of Intermediate 22 (869 mg, 1.77 mmol) in 1,4-dioxane (16 mL) and water (4 mL) at 0° C. were added sodium periodate (1.15 g, 5.31 mmol) and osmium tetroxide (0.89 mL, 0.071 mmol). The reaction mixture was stirred for 3 h at r.t. The reaction mixture was diluted with EtOAc and washed with water, Na$_2$S$_2$O$_3$ (saturated aqueous solution) and brine, then dried over anhydrous magnesium sulphate, filtered and concentrated in vacuo. The crude residue was purified by column chromatography (SiO$_2$, 30% EtOAc in heptane) to give the title compound (336 mg, 36%). LCMS Method 3 (ES+) 493 (M+H)$^+$, RT 3.32 minutes.

Intermediate 24

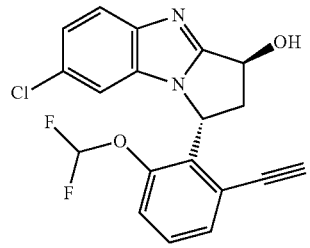 [SMILES: C#Cc1cccc(OC(F)F)c1[C@H]1C[C@H](O)c2nc3ccc(Cl)cc3n21]

(1R,3S)-7-Chloro-1-[2-(difluoromethoxy)-6-ethynylphenyl]-2,3-dihydro-1H-pyrrolo[1,2-a]benzimidazol-3-ol To a stirred solution of Intermediate 23 (336 mg, 0.68 mmol) in methanol (4 mL) was added potassium carbonate (190 mg, 1.36 mmol), followed by dimethyl (1-diazo-2- oxopropyl)phosphonate (0.20 mL, 0.82 mmol). The reaction mixture was stirred overnight at ambient temperature, then concentrated and dissolved in EtOAc. The organic phase was washed with water and dried over anhydrous magnesium sulphate, then filtered and evaporated in vacuo. The crude residue was purified by preparative LCMS (basic, Method 2) to give the title compound (67 mg, 26%). LCMS Method 3 (ES+) 375 (M+H)$^+$, RT 2.42 minutes.

Intermediate 25

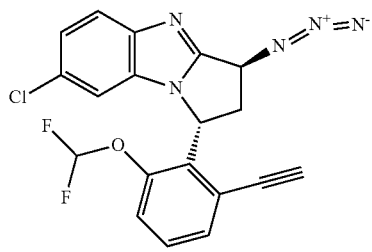 [SMILES: C#Cc1cccc(OC(F)F)c1[C@H]1C[C@H](N=[N+]=[N-])c2nc3ccc(Cl)cc3n21]

(1R)-3-Azido-7-chloro-1-[2-(difluoromethoxy)-6-ethynylphenyl]-2,3-dihydro-1H-pyrrolo[1,2-a]benzimidazole To a stirred solution of Intermediate 24 (67 mg, 0.18 mmol) in THF (0.67 mL) at 0° C. were added diphenyl phosphoryl azide (0.09 mL, 0.23 mmol) and 1,8-diazabicyclo[5.4.0]undec-7-ene (0.037 mL, 0.25 mmol). The reaction mixture was stirred overnight at 50° C., then partitioned between EtOAc (5 mL) and water (5 mL). The layers were separated and the organic phase was washed with saturated aqueous NaHCO$_3$ solution and brine, then dried over anhydrous magnesium sulphate, filtered and concentrated to dryness. The crude residue was purified by preparative LCMS (basic, Method 2) to give the title compound (49 mg, 69%). LCMS Method 3 (ES+) 400 (M+H)$^+$, RT 2.67 minutes.

Intermediate 26

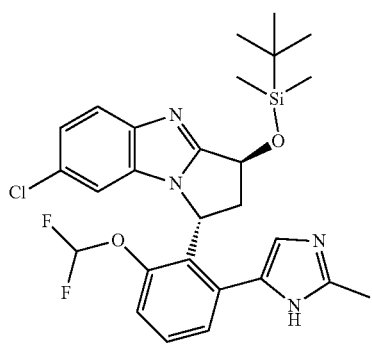 [SMILES: Cc1ncc(-c2cccc(OC(F)F)c2[C@H]2C[C@H](O[Si](C)(C)C(C)(C)C)c3nc4ccc(Cl)cc4n32)[nH]1]

tert-Butyl({(1R,3S)-7-chloro-1-[2-(difluoromethoxy)-6-(2-methyl-1H-imidazol-5-yl)phenyl]-2,3-dihydro-1H-pyrrolo[1,2-a]benzimidazol-3-yl}oxy)(dimethyl)silane To a solution of Intermediate 21 (800 mg, 1.47 mmol) in 1,4-dioxane (3.0 mL) were added [1,1'-bis(diphenylphosphino)ferrocene]dichloropalladium(II) (75 mg, 0.102 mmol), bis(pinacolato)diboron (457 mg, 1.76 mmol) and potassium acetate (437 mg, 4.4 mmol). The slurry was heated at 100° C. overnight. After cooling to ambient temperature, 4-bromo-1-(tert-butoxycarbonyl)-2-methylimidazole (374 mg, 1.77 mmol), [1,1'-bis(diphenylphosphino)ferrocene]dichloropalladium(II) (42 mg, 0.073 mmol), cesium carbonate (560 mg, 2.20 mmol), cesium fluoride (355 mg, 2.94 mmol) and water (0.22 mL) were added. The reaction mixture was degassed with nitrogen and stirred at 95° C. overnight. The crude reaction mixture was partially concentrated and purified by column chromatography (SiO$_2$, 75-100% EtOAc/heptane) to give the title compound (362 mg, 45%) as a beige solid. LCMS Method 3 (ES+) 545.1 [M+H]$^+$, RT 3.05 minutes.

Intermediate 27

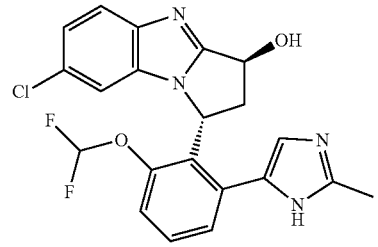 [SMILES: Cc1ncc(-c2cccc(OC(F)F)c2[C@H]2C[C@H](O)c3nc4ccc(Cl)cc4n32)[nH]1]

(1R,3S)-7-Chloro-1-[2-(difluoromethoxy)-6-(2-methyl-1H-imidazol-5-yl)phenyl]-2,3-dihydro-1H-pyrrolo[1,2-a]benzimidazol-3-ol To a solution of Intermediate 26 (175 mg, 0.32 mmol) in dry THF (1.75 mL) was added dropwise tetrabutylammonium fluoride solution (1M in THF, 0.48 mL, 0.48 mmol). The reaction mixture was stirred at ambient temperature for 2.5 h, then quenched by the addition of water and extracted with EtOAc (3×5 mL). The combined organic layers were dried over anhydrous magnesium sulphate, filtered and concentrated in vacuo to give the title compound (122 mg, 88%) as a yellow glass. LCMS Method 3 (ES+) 431 (M+H)$^+$, RT 2.10 minutes.

Intermediate 28

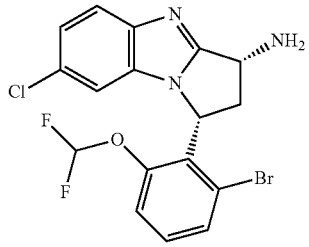 [SMILES: N[C@@H]1C[C@H](c2c(Br)cccc2OC(F)F)n2c1nc1ccc(Cl)cc12]

(1R,3R)-1-[2-Bromo-6-(difluoromethoxy)phenyl]-7-chloro-2,3-dihydro-1H-pyrrolo[1,2-a]benzimidazol-3-amine Intermediate 20 (5 g, 11.64 mmol) was suspended in toluene (22 mL) and cooled to 0° C. before the addition of diphenyl phosphoryl azide (3.4 mL, 15 mmol) and 1,8-diazabicyclo[5.4.0]undec-7-ene (2.5 mL, 16 mmol). The mixture was allowed to warm to r.t. and stirred for 2 h, and subsequently at 45° C. overnight, then diluted with EtOAc (150 mL). The organic phase was washed with saturated aqueous ammonium chloride solution (50 mL) and saturated aqueous sodium bicarbonate solution (50 mL), then concentrated in vacuo. The crude residue was dissolved in THF (100 mL) and water (10 mL), then trimethylphosphine (1M solution in toluene, 17.46 mL, 17.46 mmol) was added and the reaction mixture was stirred overnight. The mixture was concentrated in vacuo, then partitioned between EtOAc (200 mL) and water (150 mL). The organic layer was extracted with 0.2M aqueous HCl (3×200 mL). The combined acid layer was stirred in an ice bath, whilst 10% aqueous NaOH solution was added with stirring until the pH increased to 10. The stirring was continued for a further 15 minutes to complete precipitation. The precipitate was filtered and rinsed with water (20 mL), then dried under suction for 10 minutes before drying under high vacuum overnight, to afford the title compound (3.92 g, 78%) as an off-white solid. LCMS Method 1 (ES+) 428/430 (M+H)$^+$, RT 1.96 minutes.

Intermediate 29

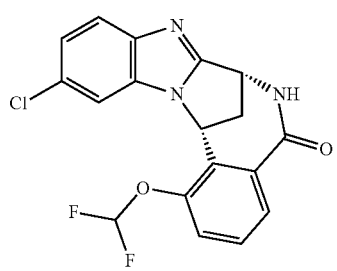 [SMILES: O=C1N[C@@H]2C[C@H](c3c(OC(F)F)cccc31)n1c2nc2ccc(Cl)cc21]

(7R,14R)-11-Chloro-1-(difluoromethoxy)-6,7-dihydro-7,14-methanobenzimidazo[1,2-b][2,5]benzodiazocin-5(14H)-one Intermediate 28 (3.7 g, 8.6 mmol), activated 4 Å molecular sieve powder (1.2 g) and potassium carbonate (13 mmol), followed by dichloro[9,9-dimethyl-4,5-bis(diphenylphosphino)xanthene]palladium(II) (0.35 mmol), were placed into a 100 mL Glass Parr reaction vessel. The reactor was evacuated and refilled with argon 3 times before anhydrous DMSO (35 mL) was added, followed by a solution of phenol (5M in DMSO, 9.5 mmol). The solution was degassed by 3 vacuum/argon cycles, followed by 3 cycles of vacuum/CO, resulting in a final CO pressure of 1 bar. The mixture was stirred and heated overnight at 100° C. under the CO atmosphere. The reaction mixture was cooled to 30° C., then the reactor vessel was opened and EtOAc (40 mL) was added. The resulting mixture was filtered through a pad of Celite and washed through with additional EtOAc (100 mL). The filtrate was evaporated in vacuo. The resulting green oil was taken up in EtOAc (100 mL). The organic layer was washed with water, saturated aqueous potassium carbonate solution and brine. The aqueous layer was re-extracted with EtOAc (50 mL). The combined organic layers were dried over anhydrous magnesium sulphate, then filtered and evaporated to dryness. The resulting green solid (3.65 g) was triturated with EtOAc, then filtered and rinsed with diethyl ether, to afford the title compound (1.06 g, 33%) as a grey solid. $\delta_H$ (300 MHz, DMSO-d$_6$) 9.12 (d, J 6.7 Hz, 1H), 8.23 (dd, J 7.0, 2.4 Hz, 1H), 7.60 (m, 5H), 7.20 (dd, J 8.7, 2.1 Hz, 1H), 6.29 (d, J 7.1 Hz, 1H), 4.87 (dd, J 6.7, 6.7 Hz, 1H), 3.46 (m, 1H), 2.72 (d, J 13.4 Hz, 1H). LCMS Method 1 MH$^+$ m/z 376, RT 1.90 minutes.

Intermediate 30

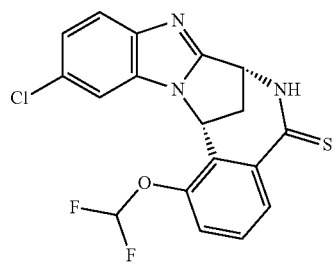 [SMILES: FC(F)Oc1cccc2c1[C@H]1C[C@@H](NC2=S)c2nc3ccc(Cl)cc3n21]

(7R,14R)-11-Chloro-1-(difluoromethoxy)-6,7-dihydro-7,14-methanobenzimidazo[1,2-b][2,5]benzodiazocin-5(14H)-thione To a suspension of Intermediate 29 (1 g, 2.66 mmol) in toluene (50 mL) was added Lawesson's reagent (1.2 g, 2.9 mmol). The slurry was stirred overnight at 110° C. The reaction mixture was evaporated and diluted in a minimum amount of EtOAc. The precipitate was filtered and rinsed with diethyl ether (2×10 mL), then the filtrate was concentrated in vacuo, to afford the title compound (1.0 g, 96%) as a yellow solid, which was utilised without further purification. LCMS Method 3 (ES+) 392 (M+H)$^+$, RT 2.48 minutes.

Intermediate 31

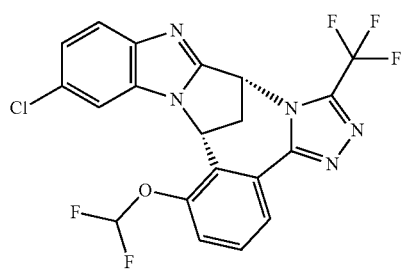 [SMILES: FC(F)Oc1cccc2c1[C@H]1C[C@H](c3nc4ccc(Cl)cc4n31)n1c-2nnc1C(F)(F)F]

(8R,15R)-11-Chloro-7-(difluoromethoxy)-1-(trifluoromethyl)-8H,15H-8,15-methanobenzimidazo[2,1-d][1,2,4]triazolo[3,4-a][2,5]benzodiazocine To a suspension of Intermediate 30 (930 mg, 2.37 mmol) and 4 Å molecular sieves (350 mg) in 1-butanol (6.5 mL) was added trifluoroacetic acid hydrazide (3 g, 23.4 mmol). The reaction mixture was stirred at 140° C. overnight, then diluted with DCM (10 mL) and water (5 mL). The two layers were separated and the organic layer was further washed with 0.1N HC (5 mL), saturated aqueous NaHCO$_3$ solution (5 mL) and brine, then dried over anhydrous magnesium sulphate, filtered and concentrated under reduced pressure. The crude material was purified by basic reverse phase LCMS, yielding the title compound (301 mg, 27%) as a white solid. LCMS Method 3 (ES+) 468 (M+H)+, RT 2.67 minutes.

Intermediate 32

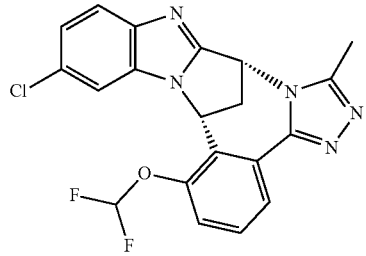 [SMILES: Cc1nnc2n1[C@@H]1C[C@H](c3c(OC(F)F)cccc3-2)n2c1nc1ccc(Cl)cc12]

(8R,15R)-11-Chloro-7-(difluoromethoxy)-1-methyl-8H,15H-8,15-methanobenzimidazo[2,1-d][1,2,4]triazolo[3,4-a][2,5]benzodiazocine Prepared from Intermediate 30 (662 mg, 1.690 mmol) following the procedure described for Intermediate 17. The crude material was purified by preparative LCMS (basic, Method 2) to give the title compound (220 mg, 31%). LCMS Method 3 (ES+) 414/416 (M+H)+, RT 3.61 minutes.

Intermediate 33

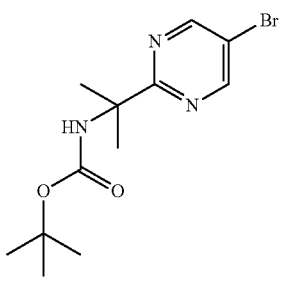 [SMILES: CC(C)(C)OC(=O)NC(C)(C)c1ncc(Br)cn1]

tert-Butyl N-[1-(5-bromopyrimidin-2-yl)-1-methylethyl]carbamate 2-(5-Bromopyrimidin-2-yl)propan-2-amine (200 mg, 0.92 mmol) was dissolved in THF (5 mL) and di-tert-butyl dicarbonate solution (1.0M in THF, 1.3 mL, 1.3 mmol) was added. After 2 h, the solvents were removed in vacuo, to afford the title compound (300 mg, 92%) as an orange gum. LCMS Method 3 (ES+) 338.0/340.0 (M+Na)+, RT 1.88 minutes.

Intermediate 34

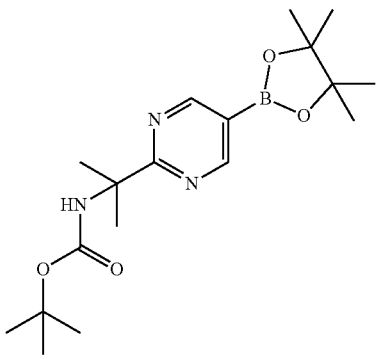 [SMILES: CC(C)(C)OC(=O)NC(C)(C)c1ncc(B2OC(C)(C)C(C)(C)O2)cn1]

tert-Butyl N-{1-methyl-1-[5-(4,4,5,5-tetramethyl-1,3,2-dioxaborolan-2-yl)pyrimidin-2-yl]ethyl}carbamate Bis(pinacolato)diboron (4.55 g, 17.6 mmol), Intermediate 33 (3.70 g, 11.7 mmol), potassium acetate (4.64 g, 46.8 mmol), [1,1'-bis(diphenylphosphino)ferrocene]-palladium (II) dichloride dichloromethane complex (1.0 g, 1.22 mmol) and 1,4-dioxane (35 mL) were placed in a reaction vessel and degassed with nitrogen. The mixture was heated at 105° C. for 1 h before being allowed to cool to ambient temperature. The reaction mixture was diluted with water and extracted with EtOAc (3×100 mL). The organic phases were combined and dried over anhydrous magnesium sulphate, then filtered and evaporated in vacuo, to afford the title compound (3.6 g, 80% crude), which was utilised without further purification. LCMS Method 3 364 (M+Na)+, RT 1.04 minutes.

Intermediate 35

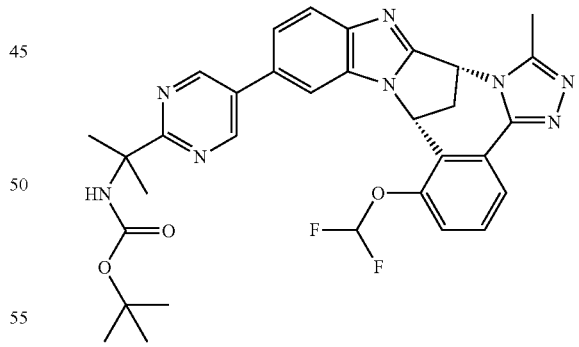

tert-Butyl N-(2-{5-[(8R,15R)-7-(Difluoromethoxy)-1-methyl-8H,15H-8,15-methanobenzimidazo[2,1-d][1,2,4]triazolo[3,4-a][2,5]benzodiazocin-11-yl]pyrimidin-2-yl}propan-2-yl)carbamate To a suspension of Intermediate 32 (40 mg, 0.097 mmol), tricyclohexylphosphonium tetrafluoroborate (8.63 mg, 0.023 mmol), potassium phosphate tribasic (42.3 mg, 0.19 mmol) and tris(dibenzylideneacetone)dipalladium(0) (8.9 mg, 0.01 mmol) in degassed (nitrogen) 1,4-dioxane (0.35 mL) and water (0.035 mL) was added Intermediate 34 (70.2 mg, 0.19 mmol) in degassed 1,4-dioxane (1 mL). The reaction mixture was heated at 135° C. overnight, then allowed to cool to ambient temperature, filtered through a pad of anhydrous magnesium sulphate, and rinsed with 1,4-dioxane (3×2 mL). The filtrate was evaporated in vacuo and the crude residue was utilised without further purification. LCMS Method 2 615.29 (M+H)+, RT 2.41 minutes.

Intermediate 36

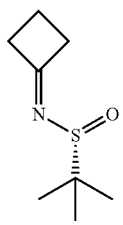

(R)-N-Cyclobutylidene-2-methylpropane-2-sulfinamide

To a solution of cyclobutanone (50 g, 713 mmol) and (R)-2-methylpropane-2-sulfinamide (82 g, 679 mmol) in anhydrous THF (1400 mL) was added titanium(IV) ethoxide (215 mL, 1019 mmol) at r.t. under a N₂ atmosphere. The reaction mixture was stirred at r.t. over the weekend, then concentrated in vacuo. The residue was dissolved in EtOAc (1 L), then saturated aqueous sodium hydrogen carbonate solution was added to the solution. The resulting thick suspension was filtered over celite, and the solids were washed with EtOAc (~1 L). The filtrate was washed with brine and dried over anhydrous sodium sulfate, then filtered and concentrated in vacuo. The crude residue (104 g) was purified by flash chromatography (SiO₂, eluting with hexanes:EtOAc, from 3:1 to 1:1 ratio) to provide the title compound (83.5 g). LCMS Method 3 (ES+) 117.1 (M-ᵗBu), RT 4.15 minutes.

Intermediate 37

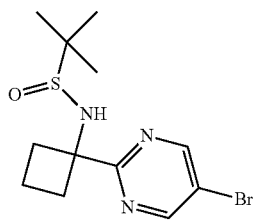 [SMILES: CC(C)(C)S(=O)NC1(c2ncc(Br)cn2)CCC1]

(R)-N-[1-(5-Bromopyrimidin-2-yl)cyclobutyl]-2-methylpropane-2-sulfinamide n-Butyllithium (2.5M in hexanes) (182 mL, 456 mmol) was added dropwise over 15 minutes to a solution of 5-bromo-2-iodopyrimidine (129 g, 452 mmol) in DCM (3000 mL) under an atmosphere of N₂ at −78° C. After 20 minutes at −78° C., a solution of Intermediate 36 (77.5 g, 447 mmol) in DCM (300 mL) was added dropwise over 30 minutes. The reaction mixture was stirred at −78° C. and allowed to warm to −20° C. overnight. The mixture was poured into ice/water (1 L) and the layers were separated. The aqueous layer was washed with DCM (2×1 L). The combined organic layers were dried over sodium sulphate, filtered and concentrated in vacuo. The crude material was purified by chromatography on silica gel (2 kg), eluting with 15-60% EtOAc in heptanes, to give the title compound (39.2 g, 26%). LCMS Method 4 (ES+) 332/334 (M+H), RT 1.86 minutes.

Intermediate 38

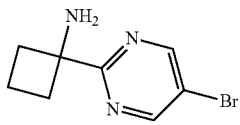 [SMILES: NC1(c2ncc(Br)cn2)CCC1]

1-(5-Bromopyrimidin-2-yl)cyclobutylamine hydrochloride

Intermediate 37 (5.66 g, 17 mmol) was dissolved in HCl (3M in MeOH, 100 mL). The mixture was stirred at r.t. for 4 h, then concentrated in vacuo. The residue was sonicated with diethyl ether/MeOH (20:1, 100 mL). A precipitate formed, then the mixture was filtered and rinsed with diethyl ether (2×15 mL). The solid was dried in vacuo to give the title compound (4.1 g, 91%) as a light yellow solid. δ$_H$ (400 MHz, DMSO-d₆) 9.15 (s, 2H), 9.00 (s, 3H), 2.69-2.54 (m, 4H), 2.27-2.01 (m, 2H).

Intermediate 39

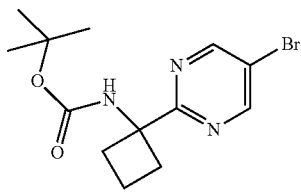 [SMILES: CC(C)(C)OC(=O)NC1(c2ncc(Br)cn2)CCC1]

tert-Butyl N-[1-(5-bromopyrimidin-2-yl)cyclobutyl]carbamate

To a suspension of Intermediate 38 (8.17 g, 35.8 mmol) in 2-methyltetrahydrofuran (80 mL) were added di-tert-butyl dicarbonate (7.40 g, 34 mmol) and triethylamine (5.2 mL, 37 mmol). The mixture was stirred at 0-5° C. for 30 minutes, then allowed to reach ambient temperature and stirred for 2.5 h. The mixture was partitioned between EtOAc (200 mL) and water (200 mL), then the layers were separated. The organic phase was washed with 25% brine (5×50 mL), water (50 mL) and brine (50 mL), then dried over anhydrous sodium sulfate, filtered and concentrated in vacuo. Purification of the crude solid by column chromatography (SiO₂, 0-20% EtOAc in hexane) gave the title compound (9.24 g, 79%) as an off-white solid. δ$_H$ (400 MHz, CDCl₃) 8.78 (s, 2H), 5.80-5.63 (m, 1H), 2.76-2.67 (m, 2H), 2.66-2.53 (m, 2H), 2.21-2.04 (m, 2H), 1.43 (s, 9H). LCMS Method 1 (ES+) 350/352 (M+Na), RT 2.20 minutes.

Intermediate 40

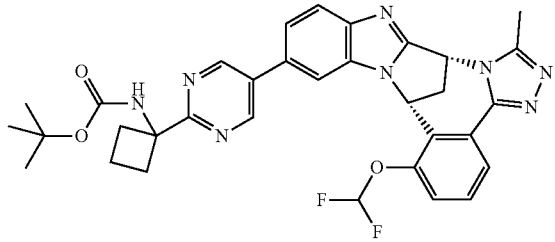 [SMILES: Cc1nnc2n1[C@@H]1C[C@H](c3c(OC(F)F)cccc3-2)n2c1nc1ccc(-c3cnc(C4(NC(=O)OC(C)(C)C)CCC4)nc3)cc12]

tert-Butyl (1-{5-[(8R,15R)-7-(difluoromethoxy)-1-methyl-8H,15H-8,15-methanobenzimidazo[2,1-d][1,2,4]triazolo[3,4-a][2,5]benzodiazocin-11-yl]pyrimidin-2-yl}cyclobutyl)carbamate Intermediate 32 (185 mg, 0.45 mmol) in 1,4-dioxane (2 mL) was added to a microwave tube together with bis(pinacolato)diboron (170 mg, 0.67 mmol), potassium acetate (132 mg, 1.34 mmol), tricyclohexylphosphonium tetrafluoroborate (17.0 mg, 0.044 mmol) and tris(dibenzylideneacetone)dipalladium(0) (16 mg, 0.022 mmol). The reaction mixture was degassed for 10 minutes, then heated at 140° C. under microwave irradiation for 3 h. Water and EtOAc were added, then the reaction mixture was extracted with further EtOAc. The combined organic layers were filtered through a separation phase filter and the solvent was evaporated. The crude material was treated with Intermediate 39 (130 mg, 0.40 mmol), K$_3$PO$_4$ (240 mg, 1.09 mmol) and tricyclohexylphosphonium tetrafluoroborate (13.8 mg, 0.036 mmol), then suspended in 1,4-dioxane (1.3 mL) and water (0.19 mL) and degassed. Tris(dibenzylideneacetone)dipalladium(0) (16.7 mg, 0.018 mmol) was added. The reaction mixture was heated at 105° C. for 3 h, then cooled to ambient temperature. The crude mixture was extracted with EtOAc (3×10 mL). The combined organic phases were washed with saturated brine (2×10 mL), then dried by passage through a separation phase filter. The solvents were removed in vacuo. Purification by column chromatography on silica gel (hexane:EtOAc from 0 to 100%, then DCM:MeOH from 0 to 15%) gave the title compound (130 mg, 43%) as a yellow solid. LCMS Method 1 627 (M+H)$^+$, RT 1.17 minutes.

Intermediate 41

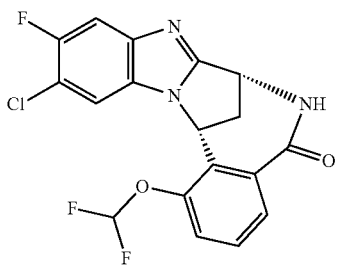 [SMILES: O=C1N[C@@H]2C[C@H](c3c(OC(F)F)cccc31)n1c2nc2cc(F)c(Cl)cc21]

(7R,14R)-11-Chloro-1-(difluoromethoxy)-10-fluoro-6,7-dihydro-7,14-methanobenzimidazo[1,2-b][2,5]benzodiazocin-5(14H)-one A mixture of (1R,3R)-1-[2-bromo-6-(difluoromethoxy)phenyl]-7-chloro-6-fluoro-2,3-dihydro-1H-pyrrolo[1,2-a]benzimidazol-3-amine (WO 2016/050975, Intermediate 41) (2.0 g, 4.5 mmol), potassium carbonate (2.5 g, 18 mmol), palladium(II) acetate (50 mg, 0.22 mmol) and 4,5-bis(diphenylphosphino)-9,9-dimethylxanthene (130 mg, 0.22 mmol, 0.13 mL) in degassed 1,4-dioxane (45 mL) in a glass lined stainless steel Parr vessel was vacuum purged and refilled three times with nitrogen, then three times with carbon monoxide, to provide a head space pressure of 25 psi. The vessel was heated to 110° C. and the reaction mixture was stirred overnight, then partitioned between EtOAc (100 mL) and water (50 mL). The aqueous phase was separated, then the organic phase was washed with water (2×50 mL) and brine (50 mL). The aqueous phase was extracted with EtOAc (100 mL), then the combined organic phases were dried (Na$_2$SO$_4$), filtered and concentrated in vacuo. The resulting green solid was washed with diethyl ether to afford the title compound as a pale solid. The filtrate was concentrated in vacuo and the precipitate was washed with diethyl ether to yield a second crop of the title compound (total yield 1.4 g, 79%). LCMS (ES+) 394.0 (M+H)$^+$, RT 1.96 minutes (Method 5).

Intermediate 42

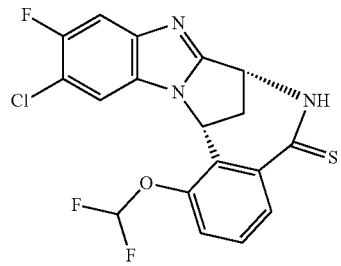 [SMILES: Fc1cc2nc3n(c2cc1Cl)[C@@H]1C[C@H]3NC(=S)c2cccc(OC(F)F)c21]

(7R,14R)-11-Chloro-1-(difluoromethoxy)-10-fluoro-6,7-dihydro-7,14-methanobenzimidazo[1,2-b][2,5]benzodiazocine-5(14H)-thione To a solution of Intermediate 41 (1.0 g, 2.54 mmol) in toluene (50 mL) was added Lawesson's reagent (1.2 g, 2.9 mmol). The reaction mixture was stirred at 110° C. overnight, then concentrated in vacuo. The crude residue was purified by flash column chromatography on silica (gradient elution with 0-100% ethyl acetate in hexane) to afford the title compound (1.5 g, 91%). LCMS (ES+) 410.0 (M+H)$^+$, RT 1.19 minutes (Method 6).

Intermediate 43

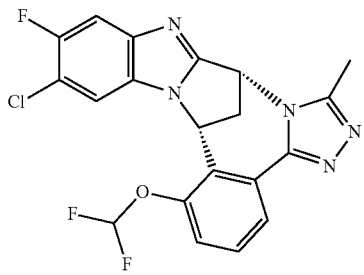 [SMILES: Cc1nnc2n1[C@@H]1C[C@H](c3c(OC(F)F)cccc3-2)n2c1nc1cc(F)c(Cl)cc12]

(8R,15R)-11-Chloro-7-(difluoromethoxy)-12-fluoro-1-methyl-8H,15H-8,15-methanobenzimidazo[2,1-d][1,2,4]triazolo[3,4-a][2,5]benzodiazocine Intermediate 42 (1.5 g, 2.20 mmol, 60% purity), N-acetylhydrazine (11.7 g, 151.6 mmol) and 4 Å molecular sieves (400 mg) in 1-butanol (11 mL) were stirred at 140° C. overnight. The reaction mixture was filtered, then the solvent was removed in vacuo. The crude residue was purified by flash column chromatography on silica (gradient elution with 0-100% EtOAc:hexanes, followed by 0-20% MeOH:DCM) to afford the title compound (160 mg, 17%). LCMS (ES+) 432.0 (M+H)+, RT 1.09 minutes (Method 6).

Intermediate 44

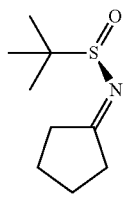

(R)-N-Cyclopentylidene-2-methylpropane-2-sulfinamide

To cyclopentanone (3.4 mL, 38 mmol) dissolved in THF (76 mL) was added titanium(IV) ethoxide (13 mL, 61.8 mmol), followed by (R)-(+)-2-methyl-2-propane-sulfinamide (3.81 g, 30.5 mmol). The reaction mixture was heated to 50° C. with stirring under nitrogen overnight, then cooled to r.t. and quenched with saturated aqueous sodium bicarbonate solution (50 mL). The white precipitate which formed was broken up and filtered through a pad of Celite, washing with EtOAc. The filtrate was separated, then the organic phase was washed sequentially with water (100 mL) and brine (100 mL). The organic phase was separated and filtered through a phase separation cartridge, then concentrated in vacuo. The resulting orange-brown oil was purified by flash column chromatography on silica (gradient elution with 100% isohexane to 70% EtOAc/isohexane) to afford the title compound (4.37 g, 77%) as a brown oil. LCMS (ES+) 188.2 (M+H)+, RT 0.781 minutes (Method 6).

Intermediate 45

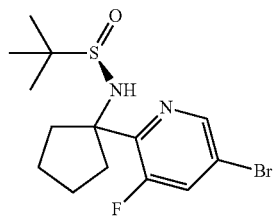 [SMILES: CC(C)(C)[S@@](=O)NC1(c2ncc(Br)cc2F)CCCC1]

(R)-N-[1-(5-Bromo-3-fluoropyridin-2-yl)cyclopentyl]-2-methylpropane-2-sulfinamide 2,5-Dibromo-3-fluoropyridine (840 mg, 3.23 mmol) dissolved in DCM (7 mL) was cooled to −65° C. and the mixture was stirred under nitrogen. To the reaction mixture was added 2.5M n-butyllithium in hexanes (1.3 mL, 3.3 mmol) dropwise. The solution was stirred at −65° C. for 15 minutes prior to dropwise addition of Intermediate 44 (505 mg, 2.70 mmol) dissolved in DCM (1 mL). The mixture was stirred at −65° C. for 1 h before warming to −45° C. for 1 h. The reaction mixture was warmed to r.t. and stirred under nitrogen for 1 h. The reaction mixture was cooled to 0° C. in an ice-bath, then quenched with saturated aqueous ammonium chloride solution (25 mL). The two phases were left to stir for 3 h. To the mixture was added DCM (25 mL). The organic phase was separated, then the aqueous phase was extracted with DCM (25 mL). The organic phases were combined and filtered through a phase separation cartridge, then concentrated in vacuo. The resulting dark brown oil was purified by flash column chromatography on silica (gradient elution with 100% isohexane to 80% EtOAc/isohexane) to afford the title compound (517 mg, 50%). LCMS (ES+) 363.0 (M+H)+, RT 1.27 minutes (Method 6).

Intermediate 46

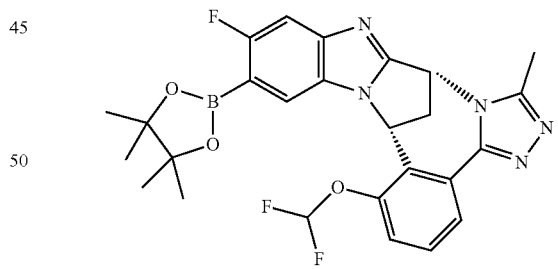

(8R,15R)-7-(Difluoromethoxy)-12-fluoro-1-methyl-11-(4,4,5,5-tetramethyl-1,3,2-dioxaborolan-2-yl)-8H,15H-8,15-methanobenzimidazo[2,1-d][1,2,4]triazolo[3,4-a][2,5]benzodiazocine Intermediate 43 (160 mg, 0.371 mmol) in 1,4-dioxane (1.3 mL) was added to bis(pinacolato)diboron (141 mg, 0.556 mmol), then potassium acetate (109 mg, 1.112 mmol), tricyclohexylphosphonium tetrafluoroborate (14.1 mg, 0.0371 mmol) and tris(dibenzylideneacetone)dipalladium (0) (17.5 mg, 0.019 mmol) were added. The reaction mixture was purged with nitrogen for 10 minutes, then heated at 140° C. in a sealed tube for 3 h under microwave irradiation. EtOAc and water was added. The two phases were separated, then the aqueous phase was extracted twice with further EtOAc. The combined organic phases were filtered through a phase separator, then the mixture was concentrated in vacuo, to afford the title compound (160 mg, 83%). LCMS (ES+) 524.2 (M+H)⁺, RT 1.94 minutes (Method 7).

Intermediate 47

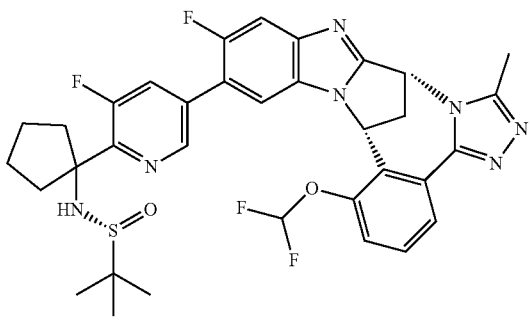

(R)-N-(1-{5-[(8R,15R)-7-(Difluoromethoxy)-12-fluoro-1-methyl-8H,15H-8,15-methanobenzimidazo[2,1-d][1,2,4]triazolo[3,4-a][2,5]benzodiazocin-11-yl]-3-fluoropyridin-2-yl}cyclopentyl)-2-methylpropane-2-sulfinamide To a mixture of Intermediate 46 (160 mg, 0.306 mmol), tris(dibenzylideneacetone)dipalladium(0) (14.0 mg, 0.0153 mmol), tricyclohexylphosphonium tetrafluoroborate (11.6 mg, 0.031 mmol) and Intermediate 45 (122 mg, 0.336 mmol) in 1,4-dioxane (1.3 mL) was added potassium phosphate tribasic (201 mg, 0.917 mmol) in water (0.13 mL). The reaction mixture was heated at 110° C. for 1.5 h. To the reaction mixture were added water and EtOAc. The phases were separated, then the aqueous phase was extracted twice with EtOAc. The combined organic phases were filtered through a phase separation cartridge and the filtrate was concentrated in vacuo. The crude residue was purified by flash column chromatography on silica (gradient elution with 0-100% EtOAc:hexanes, followed by 0-12% MeOH:DCM) to afford the title compound (115 mg, 55%). LCMS (ES+) 680.2 (M+H)⁺, RT 1.26 minutes (Method 6).

Intermediate 48

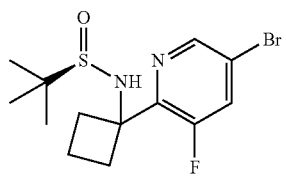 [SMILES: CC(C)(C)[S@@](=O)NC1(c2ncc(Br)cc2F)CCC1]

(R)-N-[1-(5-Bromo-3-fluoropyridin-2-yl)cyclobutyl]-2-methylpropane-2-sulfinamide 2,5-Dibromo-3-fluoropyridine (2.44 g, 9.20 mmol) was dissolved in DCM (100 mL) and cooled to −78° C. under nitrogen, then 2.5M n-butyllithium in hexanes (3.7 mL, 9.3 mmol) was added. The reaction mixture was stirred for 10 minutes prior to the addition of Intermediate 36 (1.45 g, 8.37 mmol) dissolved in DCM (2 mL). The reaction mixture was stirred at −78° C. for 1 h, then warmed to r.t. and stirred for 1 h. The reaction mixture was quenched with saturated aqueous ammonium chloride solution (50 mL), then the organic phase was separated, dried (Na₂SO₄), filtered and concentrated in vacuo. The crude residue was purified by flash column chromatography on silica (gradient elution with 30-60% EtOAc in isohexanes) to afford the title compound (1.79 g, 61%) as a colourless oil. LCMS (ES+) 349.0/351.0 (M+H)⁺, RT 1.99 minutes (Method 5).

Intermediate 49

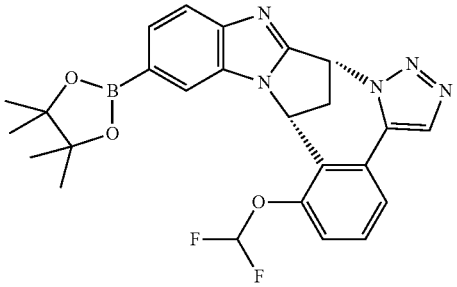

(8R,15R)-7-(Difluoromethoxy)-11-(4,4,5,5-tetramethyl-1,3,2-dioxaborolan-2-yl)-8H,15H-8,15-methanobenzimidazo[2,1-d][1,2,3]triazolo[5,1-a][2,5]benzodiazocine Example 6 (89 mg, 0.13 mmol), bis(pinacolato)diboron (48 mg, 0.19 mmol) and potassium acetate (37 mg, 0.38 mmol) were combined in 1,4-dioxane (1.2 mL) and degassed with a stream of nitrogen for 5 minutes. Tricyclohexylphosphonium tetrafluoroborate (4.6 mg, 0.01 mmol) and (1E,4E)-1,5-diphenylpenta-1,4-dien-3-one:palladium (3:2) (5.8 mg, 0.01 mmol) were added, then the mixture was heated at 140° C. in a sealed tube for 2 h. The reaction mixture was cooled to r.t., then water (5 mL) was added and the mixture was extracted with EtOAc (3×5 mL). The organic phases were combined, washed with brine (5 mL) and dried (Na₂SO₄), then filtered and concentrated in vacuo, to afford the title compound as a brown oil. LCMS (ESI) 492.3 (M+H)⁺, RT 1.77 minutes (Method 8).

Intermediate 50

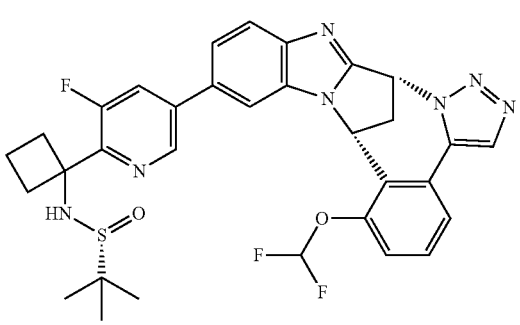

83

(R)-N-(1-{5-[(8R,15R)-7-(Difluoromethoxy)-8H,15H-8,15-methanobenzimidazo[2,1-d][1,2,3]triazolo[5,1-a][2,5]benzodiazocin-11-yl]-3-fluoropyridin-2-yl}cyclobutyl)-2-methylpropane-2-sulfinamide A mixture of Intermediate 49 (123 mg, 0.14 mmol, 57% purity) and Intermediate 48 (54.8 mg, 0.16 mmol) was dissolved in 1,4-dioxane (1.4 mL), then 2M aqueous potassium carbonate solution (208 µL) was added. The mixture was degassed with a stream of nitrogen for 5 minutes, then XPhos (6.8 mg, 0.01 mmol) and 2nd generation XPhos precatalyst (11.2 mg, 0.01 mmol) were added. The reaction mixture was stirred at 100° C. in a sealed tube for 3 h, then cooled to r.t., diluted with water (5 mL) and extracted with EtOAc (3×5 mL). The organic phases were combined and dried (Na$_2$SO$_4$), then filtered and concentrated in vacuo. The residue was purified by flash column chromatography on silica (gradient elution with 0-10% MeOH in tert-butyl methyl ether), followed by preparative HPLC (high pH, Method 6), to afford the title compound (35 mg, 28%) as a viscous oil. LCMS (ESI) 634.3 (M+H)$^+$, RT 4.39 minutes (Method 9).

Intermediates 51 & 52

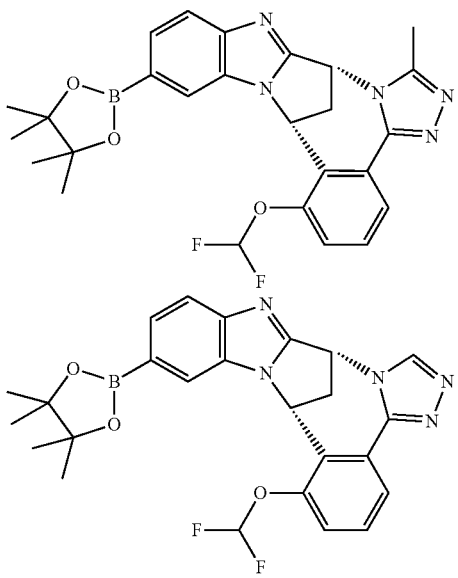

Intermediate 51

(8R,15R)-7-(Difluoromethoxy)-1-methyl-11-(4,4,5,5-tetramethyl-1,3,2-dioxaborolan-2-yl)-8H,15H-8,15-methanobenzimidazo[2,1-d][1,2,4]triazolo[3,4-a][2,5]benzodiazocine Intermediate 52

(8R,15R)-7-(Difluoromethoxy)-11-(4,4,5,5-tetramethyl-1,3,2-dioxaborolan-2-yl)-8H,15H-8,15-methanobenzimidazo[2,1-d][1,2,4]triazolo[3,4-a][2,5]benzodiazocine Tricyclohexylphosphonium tetrafluoroborate (6.6 mg, 0.017 mmol), tris-(dibenzylideneacetone)dipalladium(0) (7.2 mg, 0.0076 mmol), bis(pinacolato)diboron (51.9 mg, 0.204 mmol), potassium acetate (39.7 mg, 0.404 mmol) and Intermediate 32 (56.6 mg, 0.112 mmol) in degassed 1,4-dioxane (2 mL) were placed in a sealed tube and heated at 140° C. for 6 h, then left to stand overnight at r.t. The reaction mixture was diluted with EtOAc (20 mL) and washed with water (20 mL), followed by brine (20 mL). The organic phases were separated and dried (Na$_2$SO$_4$), then filtered under reduced pressure. The mixture was concentrated in vacuo. The resulting crude dark brown oil was purified by flash column chromatography on silica (gradient elution with 100% isohexane to 100% EtOAc, followed by 100% DCM to 25% MeOH/DCM) to afford Intermediate 51 (61.0 mg), together with a small quantity of Intermediate 52. Intermediate 51: LCMS 506.2 (M+H)$^+$, RT 1.11 minutes (Method 6).

Intermediates 53 & 54

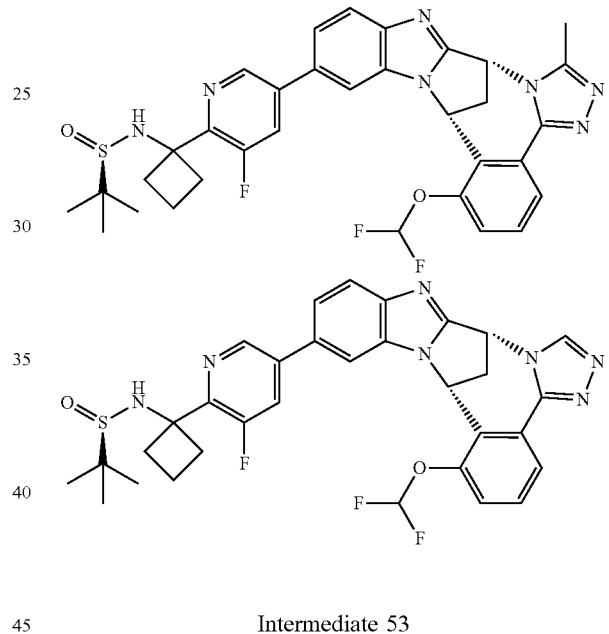

Intermediate 53

(R)-N-(1-{5-[(8R,15R)-7-(Difluoromethoxy)-1-methyl-8H,15H-8,15-methanobenzimidazo[2,1-d][1,2,4]triazolo[3,4-a][2,5]benzodiazocin-11-yl]-3-fluoropyridin-2-yl}cyclobutyl)-2-methylpropane-2-sulfinamide Intermediate 54

(R)-N-(1-{5-[(8R,15R)-7-(Difluoromethoxy)-8H,15H-8,15-methanobenzimidazo[2,1-d][1,2,4]triazolo[3,4-a][2,5]benzodiazocin-11-yl]-3-fluoropyridin-2-yl}cyclobutyl)-2-methylpropane-2-sulfinamide To a mixture of potassium phosphate tribasic (257 mg, 1.210 mmol), tricyclohexylphosphonium tetrafluoroborate (18.0 mg, 0.0474 mmol), tris(dibenzylideneacetone)dipalladium(0) (31 mg, 0.0327 mmol), Intermediate 51 and Intermediate 52 (mixture) (224 mg, 0.443 mmol) and Intermediate 48 (140 mg, 0.401 mmol) were added water (0.2 mL, degassed) and 1,4-dioxane (2 mL, degassed). The reaction mixture was heated at 110° C. in a sealed tube for 3 h, then left to cool overnight. The reaction mixture was diluted with EtOAc (20 mL) and washed with water (20 mL). The aqueous phase was separated and the organic phase was washed with brine (20 mL). To the gel which formed were added water and 10% MeOH/DCM (~30 mL), in order to provide two phases. The organic phase was separated. The aqueous phases were combined and treated with with saturated aqueous ammonium chloride solution, then extracted with 10% MeOH/DCM (25 mL). The organic phases were combined, dried (Na$_2$SO$_4$) and filtered. The solvent was removed in vacuo. The resulting brown viscous oil was purified by flash column chromatography on silica to afford Intermediate 53 and Intermediate 54 (292 mg combined). Intermediate 53: LCMS (ES+) 648.0 (M+H)$^+$, RT 2.16 minutes (Method 7); LCMS (ES+) 648.0 (M+H)$^+$, RT 2.13 minutes (Method 10). Intermediate 54: 634.0 (M+H)$^+$, RT 2.16 minutes (Method 7); 634.1 (M+H)$^+$, RT 2.13 minutes (Method 10).

Example 1

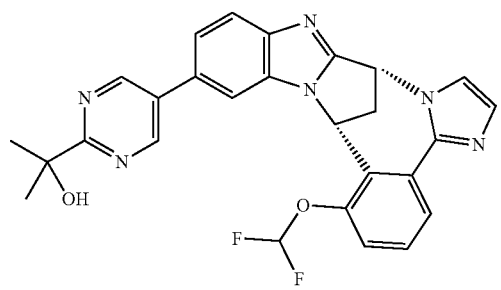

2-{5-[(8R,15R)-7-(Difluoromethoxy)-8H,15H-8,15-methanobenzimidazo[2,1-d]imidazo[2,1-a][2,5]benzodiazocin-11-yl]pyrimidin-2-yl}propan-2-ol Intermediate 16 (10 mg, 0.016 mmol) was dissolved in MeOH (1 mL) and p-toluenesulfonic acid monohydrate (15 mg, 0.079 mmol) was added. The slurry was stirred overnight at r.t. The reaction mixture was diluted with DCM (2 mL) and saturated aqueous NaHCO$_3$ solution (1 mL). The two phases were separated and the aqueous layer was further extracted with DCM (2×1 mL). The combined organic layers were dried over anhydrous magnesium sulphate, filtered and concentrated under reduced pressure. The crude residue was purified by preparative LCMS (basic, Method 2) to afford the title compound (4 mg, 49%). δ$_H$ (400 MHz, CDCl$_3$) 8.87 (d, J 8.4 Hz, 1H), 8.84 (s, 2H), 7.76 (m, 1H), 7.63 (d, J 1.1 Hz, 1H), 7.54 (s, 1H), 7.50 (t, J 8.3 Hz, 1H), 7.42 (d, J 1.5 Hz, 1H), 7.40 (m, 1H), 7.26 (d, J 8.2 Hz, 1H), 6.87 (m, 1H), 6.52 (d, J 7.4 Hz, 1H), 5.92 (d, J 6.1 Hz, 1H), 3.67 (m, 1H), 3.05 (m, 1H), 1.58 (s, 6H). LCMS Method 3 (ES+) 501 (M+H)$^+$, RT 2.08 minutes. LCMS Method 4 (ES+) 501 (M+H)$^+$, RT 1.89 minutes.

Example 2

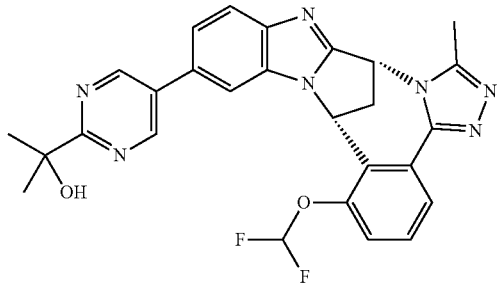

2-{5-[(8R,15R)-7-(Difluoromethoxy)-1-methyl-8H,15H-8,15-methanobenzimidazo[2,1-d][1,2,4]triazolo[3,4-a][2,5]benzodiazocin-11-yl]pyrimidin-2-yl}propan-2-ol Prepared from Intermediate 17 (42 mg, 0.067 mmol) following the procedure described for Example 1. The crude material was purified by preparative LCMS (basic, Method 2) to give the title compound (4 mg, 12%). LCMS Method 3 (ES+) 516 (M+H)$^+$, RT 1.96 minutes. LCMS Method 4 (ES+) 516 (M+H)$^+$, RT 2.13 minutes.

Example 3

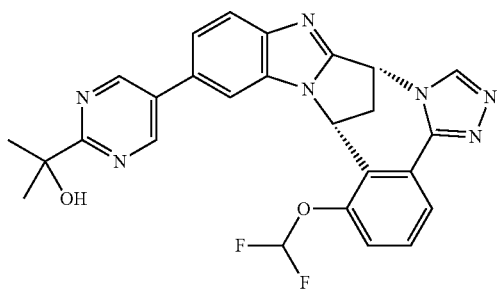

2-{5-[(8R,15R)-7-(Difluoromethoxy)-8H,15H-8,15-methanobenzimidazo[2,1-d][1,2,4]triazolo[3,4-a][2,5]benzodiazocin-11-yl]pyrimidin-2-yl}propan-2-ol Prepared from Intermediate 18 (94 mg, 0.15 mmol) following the procedure described for Example 1. The crude material was purified by preparative LCMS (basic, Method 2) to give the title compound (31 mg, 40%). δ$_H$ (400 MHz, CDCl$_3$) 8.92 (s, 2H), 8.81 (d, J 8.2 Hz, 1H), 8.57 (s, 1H), 7.82 (d, J 8.5 Hz, 1H), 7.70 (s, 1H), 7.48 (m, 2H), 7.30 (d, J 8.2 Hz, 1H), 6.92 (m, 1H), 6.56 (d, J 7.5 Hz, 1H), 5.96 (m, 1H), 4.67 (s, 1H), 3.70 (m, 1H), 3.00 (d, J 13.8 Hz, 1H), 1.66 (s, 6H). LCMS Method 3 (ES+) 502 (M+H)$^+$, RT 1.96 minutes. LCMS Method 4 (ES+) 502 (M+H)$^+$, RT 2.14 minutes.

Example 4

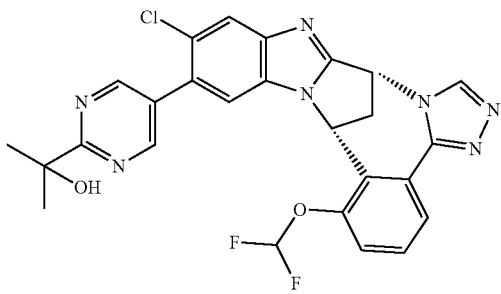

2-{5-[(8R,15R)-12-Chloro-7-(difluoromethoxy)-8H,
15H-8,15-methanobenzimidazo[2,1-d][1,2,4]triazolo
[3,4-a][2,5]benzodiazocin-11-yl]pyrimidin-2-
yl}propan-2-ol Example 3 (16 mg, 0.031 mmol) was dissolved in DMF (0.5 mL), then N-chlorosuccinimide (4.8 mg, 0.035 mmol) was added. The slurry was stirred overnight at ambient temperature. The reaction mixture was diluted with EtOAc (4 mL) and water (2 mL). The two layers were separated and the aqueous layer was further extracted with EtOAc (2×2 mL). The combined organic layers were washed with brine and dried over anhydrous magnesium sulphate, then filtered and concentrated under reduced pressure. The crude residue was purified by preparative LCMS (basic, Method 2), yielding the title compound (13 mg, 77%). $\delta_H$ (400 MHz, CDCl$_3$) 8.82 (m, 1H), 8.79 (s, 2H), 8.57 (s, 1H), 7.86 (s, 1H), 7.49 (m, 1H), 7.44 (s, 1H), 7.29 (d, J 8.1 Hz, 1H), 6.84 (m, 1H), 6.51 (d, J 7.5 Hz, 1H), 5.95 (d, J 6.1 Hz, 1H), 4.64 (s, 1H), 3.69 (m, 1H), 3.00 (m, 1H), 1.68 (s, 6H). LCMS Method 3 (ES+) 536/538 (M+H)$^+$, RT 3.67 minutes. LCMS Method 4 (ES+) 536/538 (M+H)$^+$, RT 3.95 minutes.

Example 5

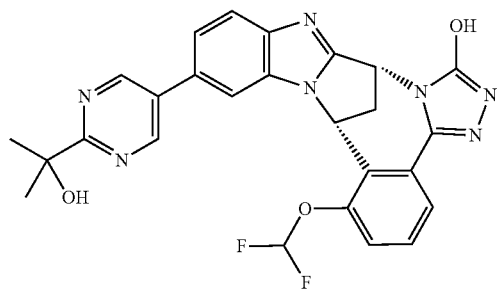

(8R,15R)-7-(Difluoromethoxy)-11-[2-(2-hydroxy-
propan-2-yl)pyrimidin-5-yl]-8H, 15H-8,15-metha-
nobenzimidazo[2,1-d][1,2,4]triazolo[3,4-a][2,5]ben-
zodiazocin-1-ol Prepared from Intermediate 19 (19 mg, 0.030 mmol) following the procedure described for Example 1. The crude residue was purified by preparative LCMS (acidic, Method 1). The resulting material was dissolved in EtOAc (2 mL) and washed with saturated aqueous NaHCO$_3$ solution. The aqueous layer was extracted with EtOAc (2×2 mL). The combined organic layers were dried over anhydrous magnesium sulphate, then filtered and concentrated in vacuo, to afford the title compound (9.9 mg, 64%) as a white solid. $\delta_H$ (400 MHz, CD$_3$OD) 9.02 (m, 2H), 8.31 (m, 1H), 7.84 (d, J 1.1 Hz, 1H), 7.77 (m, 1H), 7.59 (dd, J 8.5, 1.5 Hz, 1H), 7.44 (m, 2H), 7.36 (m, 1H), 6.62 (m, 1H), 5.96 (m, 1H), 5.88 (m, 1H), 3.76 (m, 1H), 2.96 (m, 1H), 1.65 (s, 6H). LCMS Method 3 (ES+) 518 (M+H)$^+$, RT 2.01 minutes. LCMS Method 4 (ES+) 518 (M+H)$^+$, RT 2.09 minutes.

Example 6

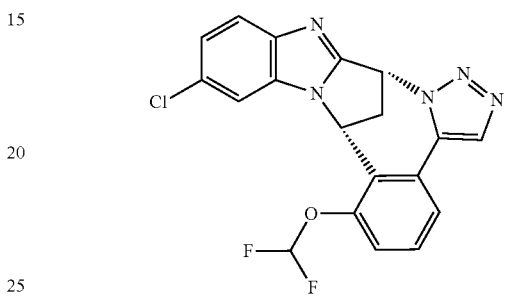

(8R,15R)-11-Chloro-7-(difluoromethoxy)-8H,15H-8,
15-methanobenzimidazo[2,1-d][1,2,3]triazolo[5,1-a]
[2,5]benzodiazocine Intermediate 25 (49 mg, 0.12 mmol) was dissolved in 1,4-dioxane (2 mL). Cuprous iodide (23 mg, 0.12 mmol) was added and the reaction mixture was stirred at 80° C. overnight. The mixture was filtered through celite, eluting with EtOAc, and the filtrate was evaporated in vacuo. The crude residue was purified by preparative LCMS (basic, Method 2) to afford the title compound (11 mg, 22%) as a white solid. $\delta_H$ (400 MHz, DMSO-d$_6$) 8.59 (s, 1H), 8.03 (d, J 8.1 Hz, 1H), 7.66 (d, J 6.3 Hz, 1H), 7.66 (m, 1H), 7.53 (t, J 8.2 Hz, 1H), 7.41 (m, 2H), 7.24 (dd, J 8.7, 1.9 Hz, 1H), 6.66 (d, J 6.1 Hz, 1H), 6.48 (d, J 7.4 Hz, 1H), 3.72 (m, 1H), 1.07 (d, J 14.1 Hz, 1H). LCMS Method 3 (ES+) 400 (M+H)$^+$, RT 2.43 minutes.

Example 7

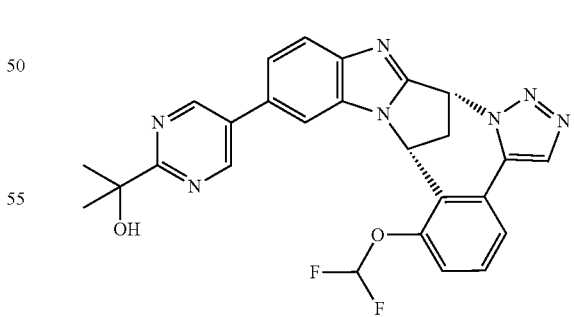

2-{5-[(8R,15R)-7-(Difluoromethoxy)-8H,15H-8,15-
methanobenzimidazo[2,1-d][1,2,3]triazolo[5,1-a][2,
5]benzodiazocin-11-yl]pyrimidin-2-yl}propan-2-ol A mixture of Example 6 (6 mg, 0.015 mmol), [2-(1-hydroxy-1-methylethyl)-pyrimidin-5-yl]boronic acid (8 mg, 0.030 mmol), tricyclohexylphosphonium tetrafluoroborate (1.3 mg, 0.0036 mmol), potassium phosphate tribasic (6.4 mg, 0.030 mmol) and 1-butanol (3.6 mL/g) was degassed with nitrogen and tris(dibenzylideneacetone)dipalladium(0) (1.4 mg, 0.0015 mmol) was added. The mixture was heated for 10 minutes at 140° C. under microwave irradiation. The reaction mixture was filtered through celite, eluting with EtOAc, and the filtrate was concentrated to dryness. The crude residue was purified by preparative LCMS (basic, Method 2) to afford the title compound (1.2 mg, 16%) as an off-white solid. LCMS Method 3 (ES+) 502 (M+H)$^+$, RT 2.10 minutes. LCMS Method 4 (ES+) 502 (M+H)$^+$, RT 2.31 minutes.

Example 8

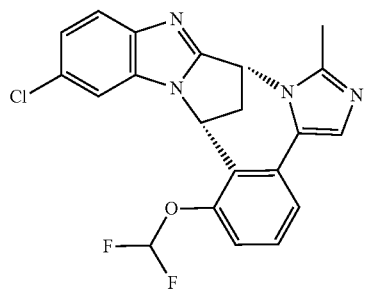

(8R,15R)-11-Chloro-7-(difluoromethoxy)-1-methyl-8H,15H-8,15-methanobenzimidazo[2,1-d]imidazo[5,1-a][2,5]benzodiazocine To a cold solution of Intermediate 27 (120 mg, 0.28 mmol) and triphenylphosphine (185 mg, 0.70 mmol) in THF (3.6 mL) was added diisopropyl azodicarboxylate (0.11 mL, 0.56 mmol) diluted in THF (0.3 mL). The reaction mixture was stirred at 0° C. for 4 h, then at ambient temperature. The reaction mixture was diluted with water (1 mL) and extracted with EtOAc (3×1 mL). The combined organic layers were dried over anhydrous magnesium sulphate, filtered and concentrated in vacuo. The crude material was purified by column chromatography (SiO$_2$, 50-100% EtOAc/heptane, then 5-10% EtOH/DCM) to give the title compound (42 mg, 36%) as a beige solid, together with (8R,15S)-11-chloro-7-(difluoromethoxy)-2-methyl-8,15-dihydro-3H-8,15-methanobenzimidazo[1,2-b]imidazo[4,5-e][2]benzazocine (86:14 mixture, as determined by NMR). LCMS Method 3 (ES+) 413 (M+H)$^+$, RT 4.20 minutes.

Examples 9 & 10

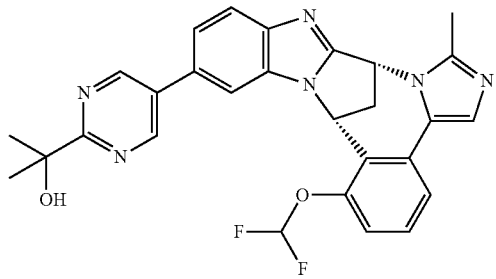

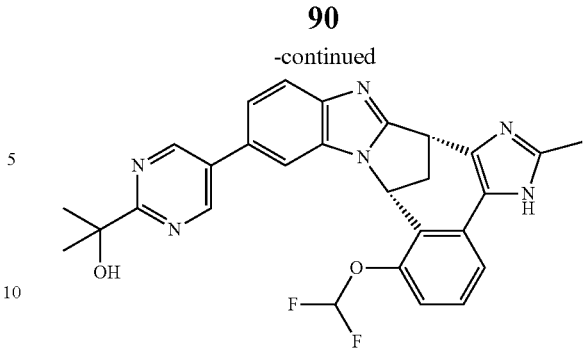

Example 9

2-{5-[(8R,15R)-7-(Difluoromethoxy)-1-methyl-8H,15H-8,15-methanobenzimidazo[2,1-d]imidazo[5,1-a][2,5]benzodiazocin-11-yl]pyrimidin-2-yl}propan-2-ol Example 10

2-{5-[(8R,15S)-7-(Difluoromethoxy)-2-methyl-8,15-dihydro-3H-8,15-methanobenzimidazo[1,2-b]imidazo[4,5-e][2]benzazocin-11-yl]pyrimidin-2-yl}propan-2-ol Example 8 (24 mg, 0.058 mmol), [2-(1-hydroxy-1-methylethyl)pyrimidin-5-yl]boronic acid (32 mg, 0.12 mmol), tricyclohexylphosphonium tetrafluoroborate (5.2 mg, 0.014 mmol), tris(dibenzenylideneacetone)dipaladium(0) (5.3 mg, 0.0058 mmol), potassium phosphate tribasic (26 mg, 0.12 mmol) and water (8.6 µL) were added to degassed 1-butanol (100 µL). The reaction mixture was stirred at 140° C. under microwave irradiation for 25 minutes. The crude reaction mixture was filtered, diluted with heptane (1 mL) and concentrated. The residue was purified by basic reverse phase preparative LCMS (basic, Method 2).

Example 9 (6 mg, 20%) was obtained as an off-white solid. δ$_H$ (400 MHz, CD$_3$OD) 9.01 (s, 2H), 7.85 (s, 1H), 7.84 (d, J 10.0 Hz, 1H), 7.76 (d, J 8.5 Hz, 1H), 7.64 (s, 1H), 7.59 (d, J 7.7 Hz, 1H), 7.34 (t, J 8.3 Hz, 1H), 7.33 (t, J 73.0 Hz, 1H), 7.18 (d, J 8.1 Hz, 1H), 6.62 (d, J 7.5 Hz, 1H), 6.16 (d, J 6.4 Hz, 1H), 4.63 (br s, 1H), 3.74 (m, 1H), 2.98 (d, J 13.9 Hz, 1H), 2.81 (s, 3H), 1.66 (s, 6H). LCMS Method 3 (ES+) 515 (M+H)$^+$, RT 2.09 minutes.

Example 10 (2.4 mg, 10%) was obtained as an off-white solid. δ$_H$ (400 MHz, CDCl$_3$) 8.96 (s, 2H), 8.95 (d, J 4.8 Hz, 1H), 8.46 (d, J 8.1 Hz, 1H), 7.97 (d, J 8.6 Hz, 1H), 7.85 (s, 1H), 7.62 (d, J 7.9 Hz, 1H), 7.46 (t, J 8.4 Hz, 1H), 7.17 (d, J 7.8 Hz, 1H), 6.91 (t, J 72.8 Hz, 1H), 6.66 (d, J 8.0 Hz, 1H), 6.24 (d, J 7.3 Hz, 1H), 3.77 (m, 1H), 3.08 (d, J 13.7 Hz, 1H), 3.01 (s, 3H), 1.70 (s, 6H). LCMS Method 3 (ES+) 515 (M+H)$^+$, RT 2.10 minutes.

Example 11

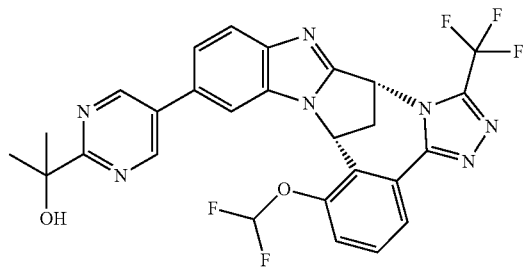 [SMILES: CC(C)(O)c1ncc(-c2ccc3nc4n(c3c2)[C@@H]2C[C@H]4n3c(nnc3C(F)(F)F)-c3cccc(OC(F)F)c32)cn1]

2-{5-[(8R,15R)-7-(Difluoromethoxy)-1-(trifluoromethyl)-8H,15H-8,15-methanobenzimidazo[2,1-d][1,2,4]triazolo[3,4-a][2,5]benzodiazocin-11-yl]pyrimidin-2-yl}propan-2-ol Intermediate 31 (150 mg, 0.32 mmol), 2-[5-(4,4,5,5-tetramethyl-1,3,2-dioxaborolan-2-yl)pyrimidin-2-yl]propan-2-ol (169 mg, 0.64 mmol), potassium phosphate tribasic (175 mg, 0.80 mmol), tricyclohexylphosphonium tetrafluoroborate (14 mg, 0.038 mmol) and tris(dibenzylideneacetone)dipalladium(0) (15 mg, 0.016 mmol) were placed in a tube under argon. Degassed 1,4 dioxane (3 mL) and water (0.3 mL) were added and the resulting slurry was stirred overnight at 120° C. The reaction mixture was cooled to r.t. before the addition of EtOAc (2 mL) and water (1 mL). The two layers were separated and the aqueous layer was further extracted with EtOAc (2×2 mL). The combined organic layers were dried over anhydrous magnesium sulphate, filtered and concentrated under reduced pressure. The crude material was purified by preparative LCMS (basic, Method 2), yielding the title compound (81 mg, 44%). $\delta_H$ (400 MHz, CDCl$_3$) 8.92 (s, 2H), 8.88 (d, J 8.1 Hz, 1H), 7.89 (d, J 8.5 Hz, 1H), 7.70 (d, J 1.2 Hz, 1H), 7.52 (m, 1H), 7.47 (dd, J 8.5, 1.7 Hz, 1H), 7.36 (m, 1H), 6.92 (m, 1H), 6.56 (d, J 7.5 Hz, 1H), 6.08 (m, 1H), 4.64 (m, 1H), 3.76 (m, 1H), 3.05 (m, 1H), 1.66 (s, 6H). LCMS Method 3 (ES+) 570 (M+H)$^+$ RT 4.01 minutes. LCMS Method 4 (ES+) 570 (M+H)$^+$, RT 4.40 minutes.

Example 12

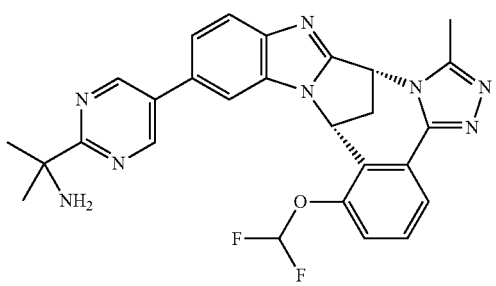 [SMILES: Cc1nnc2n1[C@@H]1C[C@H](c3c(OC(F)F)cccc3-2)n2c1nc1ccc(-c3cnc(C(C)(C)N)nc3)cc12]

2-{5-[(8R,15R)-7-(Difluoromethoxy)-1-methyl-8H,15H-8,15-methanobenzimidazo[2,1-d][1,2,4]triazolo[3,4-a][2,5]benzodiazocin-11-yl]pyrimidin-2-yl}propan-2-amine To a solution of Intermediate 35 (59.4 mg, 0.097 mmol) in DCM (1 mL) at 0° C. was added trifluoroacetic acid (1 mL) slowly. The reaction mixture was stirred at 0° C. for 1.5 h, then slowly poured onto ice-cold saturated aqueous NaHCO$_3$ solution (2 mL). The aqueous layer was extracted with DCM (3×5 mL). The combined organic layers were dried over anhydrous sodium sulfate, filtered and concentrated in vacuo. The residue was purified by basic reverse phase preparative LCMS (basic, Method 2) to afford the title compound (25 mg, 50%) as a white solid. $\delta_H$ (400 MHz, CD$_3$OD) 8.89 (s, 2H), 8.45 (d, J 8.0 Hz, 1H), 7.75 (s, 1H), 7.65 (d, J 8.5 Hz, 1H), 7.48 (m, 1H), 7.36 (m, 2H), 7.28 (t, J 73.3 Hz, 1H), 6.57 (d, J 7.4 Hz, 1H), 6.06 (d, J 6.2 Hz, 1H), 3.70 (m, 1H), 3.21 (s, 3H), 2.95 (d, J 14.1 Hz, 1H), 1.49 (s, 6H). LCMS Method 3 (ES+) 515 (M+H)$^+$, RT 3.10 minutes. LCMS Method 4 (ES+) 515.21 (M+H)$^+$, RT 2.87 minutes.

Example 13

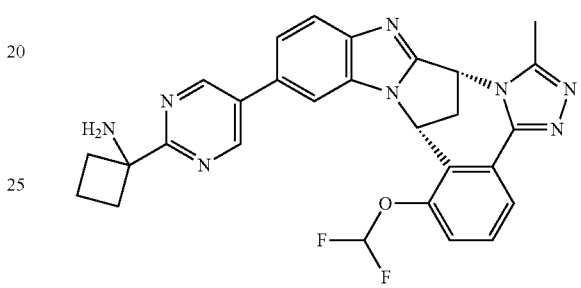

1-{5-[(8R,15R)-7-(Difluoromethoxy)-1-methyl-8H,15H-8,15-methanobenzimidazo[2,1-d][1,2,4]triazolo[3,4-a][2,5]benzodiazocin-11-yl]pyrimidin-2-yl}cyclobutanamine HCl (4N in MeOH, 2.0 mL, 8.0 mmol) was added to a suspension of Intermediate 40 (34 mg, 0.054 mmol) in 1,4 dioxane (2 mL) at room temperature. The reaction mixture was stirred at ambient temperature for 1 h, then dissolved in water and DCM was added. The aqueous layer was extracted twice with further dichloromethane, then the aqueous phase was freeze-dried, to give the hydrochloride salt of the title compound (29 mg, 89%) as a white solid. $\delta_H$ (400 MHz, DMSO-d$_6$) 9.22 (s, 2H), 8.90 (br s, 3H), 8.53 (dd, J 8.2, 1.2 Hz, 1H), 7.87-7.66 (m, 3H), 7.75 (t, J 73.20 Hz, 1H), 7.61-7.47 (m, 1H), 7.43 (d, J 7.7 Hz, 1H), 6.51 (d, J 7.4 Hz, 1H), 6.23 (d, J 6.3 Hz, 1H), 3.82-3.65 (m, 1H), 3.02 (d, J 14.1 Hz, 1H), 2.77 (s, 3H), 2.75-2.57 (m, 4H), 2.19 (dd, J 16.4, 6.8 Hz, 2H). LCMS Method 1 527 (M+H)$^+$, RT 0.98 minutes.

Example 14

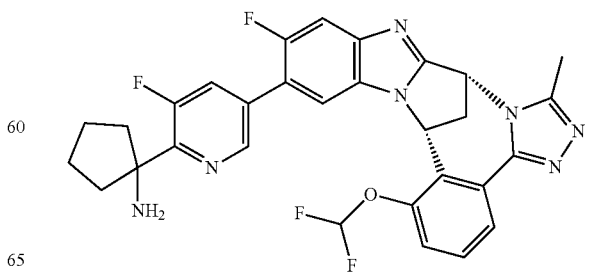

1-{5-[(8R,15R)-7-(Difluoromethoxy)-12-fluoro-1-methyl-8H,15H-8,15-methanobenzimidazo[2,1-d][1,2,4]triazolo[3,4-a][2,5]benzodiazocin-11-yl]-3-fluoropyridin-2-yl}cyclopentanamine hydrochloride (1:1)

To a suspension of Intermediate 47 (70 mg, 0.103 mmol) in 4M hydrochloric acid in 1,4-dioxane (2 mL, 8 mmol) was added 4M hydrochloric acid in MeOH (2 mL, 8 mmol). The reaction mixture was stirred overnight, then diluted with DCM (10 mL) and water (20 mL). The two phases were separated and the aqueous phase was washed twice with DCM. The organic phases were discarded. The aqueous phase was concentrated in vacuo and freeze-dried to afford the title compound (40 mg, 67%). $\delta_H$ (300 MHz, DMSO-$d_6$) 8.65-8.51 (m, 5H), 8.12-8.01 (m, 1H), 7.93-7.36 (m, 5H), 6.47 (d, J 7.3 Hz, 1H), 6.20 (d, J 6.2 Hz, 1H), 3.00 (d, J 14.0 Hz, 1H), 2.73 (s, 3H), 2.40-1.83 (m, 9H). LCMS (ES+) 576.0 (M+H)$^+$, RT 1.83 minutes (Method 5). LCMS (ES+) 576.0 (M+H)$^+$, RT 1.54 minutes (Method 10).

Example 15

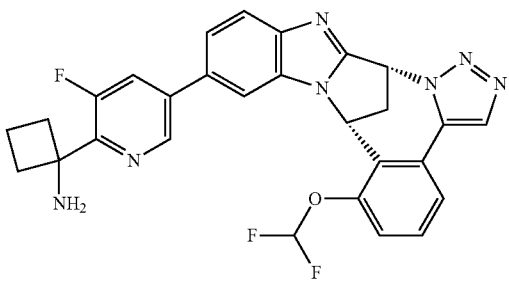 [SMILES: NC1(c2ncc(-c3ccc4nc5n(c4c3)[C@@H]3C[C@H]5n4nncc4-c4cccc(OC(F)F)c43)cc2F)CCC1]

1-{5-[(8R,15R)-7-(Difluoromethoxy)-8H,15H-8,15-methanobenzimidazo[2,1-d][1,2,3]triazolo[5,1-a][2,5]benzodiazocin-11-yl]-3-fluoropyridin-2-yl}cyclobutanamine hydrochloride (1:1)

To a solution of Intermediate 50 (35 mg, 0.055 mmol) in 1,4-dioxane (1 mL) was added 4M hydrogen chloride in 1,4-dioxane (0.07 mL) at r.t. The reaction mixture was stirred for 1 h, then concentrated in vacuo. The residue was purified by SCX column chromatography (MeOH, then 2N ammonia/MeOH). The residue was dissolved in 1:1 acetonitrile/water (2 mL), then 1M aqueous hydrochloric acid solution (1 equivalent) was added. The solution was freeze-dried to afford the title compound (10 mg, 32%) as a colourless solid. $\delta_H$ (500 MHz, CD$_3$OD) 8.73 (t, J 1.7 Hz, 1H), 8.43 (s, 1H), 8.03-7.94 (m, 2H), 7.90 (d, J 1.3 Hz, 1H), 7.76 (d, J 8.5 Hz, 1H), 7.65 (dd, J 8.6, 1.8 Hz, 1H), 7.54-7.48 (m, 1H), 7.39 (d, J 8.2 Hz, 1H), 7.38 (d, J 2.7 Hz, 1H), 6.73 (dd, J 16.2, 6.8 Hz, 2H), 3.89-3.80 (m, 1H), 3.12-3.01 (m, 3H), 2.65-2.57 (m, 2H), 2.43-2.32 (m, 1H), 2.31-2.19 (m, 1H), no NH$_3^+$ peak observed. LCMS (ESI) 530.2 (M+H)$^+$, RT 3.96 minutes (Method 11).

Example 16

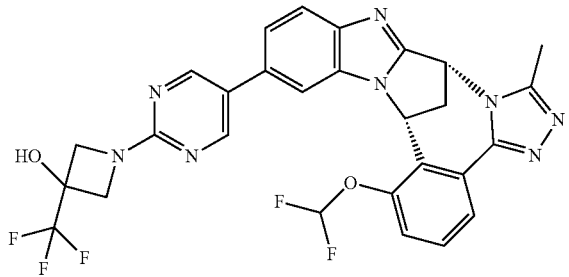 [SMILES: Cc1nnc2n1[C@@H]1C[C@H](c3c(OC(F)F)cccc3-2)n2c1nc1ccc(-c3cnc(N4CC(O)(C(F)(F)F)C4)nc3)cc12]

1-{5-[(8R,15R)-7-(Difluoromethoxy)-1-methyl-8H,15H-8,15-methanobenzimidazo[2,1-d][1,2,4]triazolo[3,4-a][2,5]benzodiazocin-11-yl]pyrimidin-2-yl}-3-(trifluoromethyl)azetidin-3-ol To potassium phosphate tribasic (114 mg, 0.54 mmol) were added tricyclohexylphosphonium tetrafluoroborate (13.0 mg, 0.034 mmol), tris(dibenzylideneacetone)dipalladium(0) (14 mg, 0.015 mmol), Intermediate 32 (145 mg, 0.165 mmol) and 1-[5-(4,4,5,5-tetramethyl-1,3,2-dioxaborolan-2-yl)pyrimidin-2-yl]-3-(trifluoromethyl)azetidin-3-ol (WO 2016/050975, Intermediate 100) (74.2 mg, 0.215 mmol) in 1,4-dioxane (3 mL) and water (1 mL). The reagents were heated at 110° C. for 3 h in a sealed tube. The reaction mixture was diluted with EtOAc (20 mL) and washed with water (20 mL), followed by brine (20 mL). The organic phase was separated and dried (Na$_2$SO$_4$), then filtered under reduced pressure. The solvent was removed in vacuo. The resulting crude brown oil was purified by flash column chromatography on silica (gradient elution with 100% isohexane to 100% EtOAc, followed by 100% DCM to 25% MeOH/DCM). The residue was further purified by preparative HPLC (high pH, Method 3) to afford the title compound (29 mg, 29%) as an off-white solid. $\delta_H$ (300 MHz, DMSO-$d_6$) 8.69 (s, 2H), 8.53 (dd, J 8.2, 1.1 Hz, 1H), 8.00-7.34 (m, 7H), 6.47 (d, J 7.4 Hz, 1H), 6.15 (d, J 6.1 Hz, 1H), 4.34 (d, J 10.3 Hz, 2H), 4.11 (d, J 10.2 Hz, 2H), 3.70 (p, J 7.0 Hz, 1H), 2.97 (d, J 14.0 Hz, 1H), 2.72 (s, 3H). LCMS 597.0 (M+H)$^+$, RT 1.81 minutes (Method 10). LCMS 597.0 (M+H)$^+$, RT 1.83 minutes (Method 5).

Examples 17 & 18

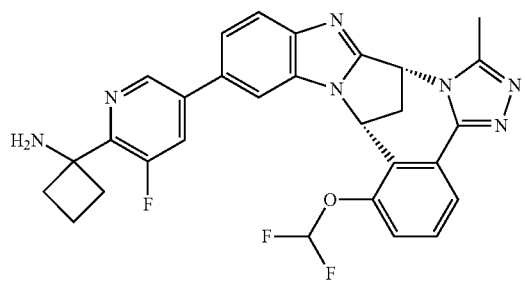

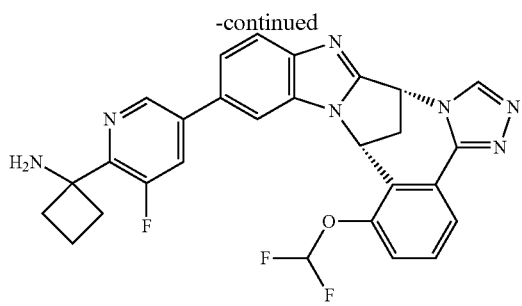

Example 17

1-{5-[(8R,15R)-7-(Difluoromethoxy)-1-methyl-8H,15H-8,15-methanobenzimidazo[2,1-d][1,2,4]triazolo[3,4-a][2,5]benzodiazocin-11-yl]-3-fluoropyridin-2-yl}cyclobutanamine Example 18

1-{5-[(8R,15R)-7-(Difluoromethoxy)-8H,15H-8,15-methanobenzimidazo[2,1-d][1,2,4]triazolo[3,4-a][2,5]benzodiazocin-11-yl]-3-fluoropyridin-2-yl}cyclobutanamine To Intermediate 53 and Intermediate 54 (mixture) (292 mg, 0.451 mmol) dissolved in MeOH (9 mL) was added 4M hydrogen chloride in 1,4-dioxane (0.6 mL). The reaction mixture was stirred at r.t. for 1.5 h, then the solvent was removed in vacuo. The resulting yellow solid was purified by preparative HPLC (polar organic preparative HPLC, Method 4) to afford Example 17 (55 mg, 22%) as a white solid, together with Example 18 (24 mg, 9.3%) as a white solid mixed with 7% of Example 17.

Example 17 (major component): $\delta_H$ (300 MHz, DMSO-$d_6$) 8.61 (t, J 1.8 Hz, 1H), 8.54 (dd, J 8.2, 1.2 Hz, 1H), 8.00-7.37 (m, 7H), 6.49 (d, J 7.5 Hz, 1H), 6.17 (d, J 6.2 Hz, 1H), 3.71 (p, J 7.0 Hz, 1H), 2.98 (d, J 14.1 Hz, 1H), 2.73 (s, 3H), 2.71-2.59 (m, 2H), 2.19-2.01 (m, 5H), 1.72-1.56 (m, 1H). LCMS 544.37 (M+H)$^+$, RT 1.55 minutes (Method 12). LCMS 544.37 (M+H)$^+$, RT 1.91 minutes (Method 13).

Example 18 (minor component): $\delta_H$ (300 MHz, DMSO-$d_6$) 9.07 (s, 1H), 8.60 (t, J 1.9 Hz, 1H), 8.57 (dd, J 8.1, 1.2 Hz, 1H), 8.00-7.39 (m, 7H), 6.52 (d, J 7.5 Hz, 1H), 6.34 (d, J 6.1 Hz, 1H), 3.73 (p, J 7.0 Hz, 1H), 2.99 (d, J 14.0 Hz, 1H), 2.75-2.57 (m, 2H), 2.20-2.00 (m, 5H), 1.77-1.56 (m, 1H). LCMS 530.3 (M+H)$^+$, RT 1.52 minutes (Method 12). LCMS 530.3 (M+H)$^+$, RT 1.90 minutes (Method 13).

Example 19

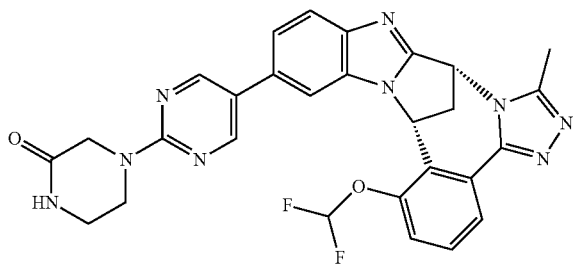 [SMILES: Cc1nnc2n1[C@@H]1C[C@H](c3c(OC(F)F)cccc3-2)n2c1nc1ccc(-c3cnc(N4CCNC(=O)C4)nc3)cc12]

4-{5-[(8R,15R)-7-(Difluoromethoxy)-1-methyl-8H,15H-8,15-methanobenzimidazo[2,1-d][1,2,4]triazolo[3,4-a][2,5]benzodiazocin-11-yl]pyrimidin-2-yl}piperazin-2-one To potassium phosphate tribasic (164 mg, 0.77 mmol), tricyclohexylphosphonium tetrafluoroborate (15 mg, 0.04 mmol), tris(dibenzylideneacetone)dipalladium(0) (30 mg, 0.0316 mmol), Intermediate 32 (106 mg, 0.257 mmol) and [2-(3-oxopiperazin-1-yl)-pyrimidin-5-yl]boronic acid (74 mg, 0.334 mmol) were added water (0.12 mL, degassed) and 1,4-dioxane (3 mL, degassed). The reaction mixture was heated at 110° C. in a sealed tube for 3 h, then cooled to r.t. and partitioned between water (25 mL) and EtOAc (25 mL). The organic phase was separated and the aqueous phase was extracted with further EtOAc (25 mL). The organic phases were combined, washed with brine (25 mL) and separated, then dried (Na$_2$SO$_4$) and filtered under reduced pressure. The solvent was removed in vacuo. The resulting crude yellow oil was purified by flash column chromatography on silica (gradient elution with 100% isohexane to 100% EtOAc, followed by 100% DCM to 20% MeOH/DCM). The resulting off-white solid (11.2 mg) was further purified by preparative HPLC (pH 10, Method 5) to afford the title compound (2 mg, 1.4%) as an off-white solid. $\delta_H$ (300 MHz, CD$_3$OD) 8.64 (s, 2H), 8.57 (dd, J 8.0, 1.4 Hz, 1H), 7.73-7.12 (m, 6H), 6.64 (d, J 7.5 Hz, 1H), 6.14 (d, J 6.3 Hz, 1H), 4.42 (s, 2H), 4.12-4.05 (m, 2H), 3.86-3.73 (m, 1H), 3.46 (t, J 5.4 Hz, 2H), 3.04 (d, J 14.1 Hz, 1H), 2.86 (s, 3H). LCMS 556.0 (M+H)$^+$, RT 1.44 minutes (Method 5). LCMS 556.2 (M+H)$^+$, RT 1.41 minutes (Method 10).

The invention claimed is:

1. A compound of formula (I) or an N-oxide thereof, or a pharmaceutically acceptable salt thereof:

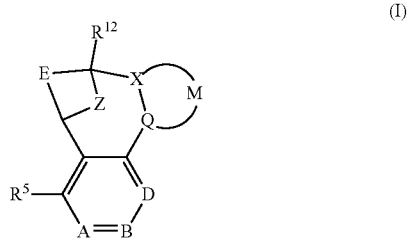

wherein

A represents C—R$^6$;

B represents C—R$^7$;

D represents C—R$^8$;

—(X-M-Q)— represents an optionally substituted five-membered heteroaromatic ring selected from pyrrolyl, pyrazolyl, imidazolyl, triazolyl and tetrazolyl optionally substituted by one, two or three substituents selected from C$_{1-6}$ alkyl, trifluoromethyl, hydroxy and oxo;

Z represents methylene;

E represents a fused heteroaromatic ring system of formula (Ea)

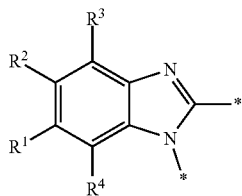

(Ea)

wherein the asterisks (*) represent the site of attachment of E to the remainder of the molecule;

R¹ represents chloro; or R¹ represents pyrimidinyl, cyclobutylpyridinyl, cyclopentylpyridinyl, cyclobutylpyrimidinyl, azetidinylpyrimidinyl or piperazinylpyrimidinyl, any of which groups may be optionally substituted by one two or three substituents independently selected from halogen, trifluoromethyl, hydroxy, hydroxy($C_{1-6}$)alkyl, oxo, amino and amino($C_{1-6}$)alkyl;
R² represents hydrogen or halogen;
R³ and R⁴ independently represent hydrogen, halogen or or $C_{1-6}$ alkyl;
R⁵ represents difluoro-methoxy or methoxy;
R⁶ represents hydrogen, halogen or trifluoromethyl;
R⁷ represents hydrogen or trifluoromethyl;
R⁸ represents hydrogen or trifluoromethyl; and
R¹² represents hydrogen or $C_{1-6}$ alkyl.

2. The compound as claimed in claim 1 represented by formula (IIA) or an N-oxide thereof, or a pharmaceutically acceptable salt thereof:

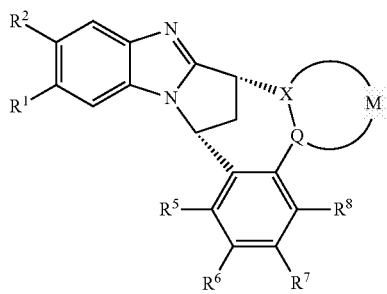

(IIA)

wherein —(X-M-Q)-, R¹, R², R⁵, R⁶, R⁷ and R⁸ are as defined in claim 1.

3. The compound as claimed in claim 2 represented by formula (IIA-1) or an N-oxide thereof, or a pharmaceutically acceptable salt thereof:

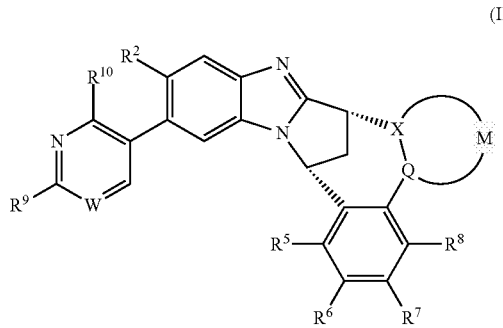

(IIA-1)

wherein
W represents N, CH or CF;
R⁹ represents hydroxy($C_{1-6}$)alkyl or amino($C_{1-6}$)alkyl;
R¹⁰ represents hydrogen or $C_{1-6}$ alkyl.

4. The compound as claimed in claim 1 selected from
2-{5-[(8R,15R)-7-(Difluoromethoxy)-8H,15H-8,15-methanobenzimidazo[2,1-d]imidazo-[2,1-a][2,5]benzodiazocin-11-yl]pyrimidin-2-yl}propan-2-ol;
2-{5-[(8R,15R)-7-(Difluoromethoxy)-1-methyl-8H,15H-8,15-methanobenzimidazo[2,1-d][1,2,4]triazolo[3,4-a][2,5]benzodiazocin-11-yl]pyrimidin-2-yl}propan-2-ol;
2-{5-[(8R,15R)-7-(Difluoromethoxy)-8H,15H-8,15-methanobenzimidazo[2,1-d][1,2,4]-triazolo[3,4-a][2,5]benzodiazocin-11-yl]pyrimidin-2-yl}propan-2-ol;
2-{5-[(8R,15R)-12-Chloro-7-(difluoromethoxy)-8H,15H-8,15-methanobenzimidazo[2,1-d][1,2,4]triazolo[3,4-a][2,5]benzodiazocin-11-yl]pyrimidin-2-yl}propan-2-ol;
(8R,15R)-7-(Difluoromethoxy)-11-[2-(2-hydroxypropan-2-yl)pyrimidin-5-yl]-8H,15H-8,15-methanobenzimidazo[2,1-d][1,2,4]triazolo[3,4-a][2,5]-benzodiazocin-1-ol;
(8R,15R)-11-Chloro-7-(difluoromethoxy)-8H,15H-8,15-methanobenzimidazo[2,1-d]-[1,2,3]triazolo[5,1-a][2,5]benzodiazocine;
2-{5-[(8R,15R)-7-(Difluoromethoxy)-8H,15H-8,15-methanobenzimidazo[2,1-d][1,2,3]-triazolo[5,1-a][2,5]benzodiazocin-11-yl]pyrimidin-2-yl}propan-2-ol;
(8R,15R)-11-Chloro-7-(difluoromethoxy)-1-methyl-8H,15H-8,15-methanobenzimidazo-[2,1-d]imidazo[5,1-a][2,5]benzodiazocine;
2-{5-[(8R,15R)-7-(Difluoromethoxy)-1-methyl-8H,15H-8,15-methanobenzimidazo[2,1-d]imidazo[5,1-a][2,5]benzodiazocin-11-yl]pyrimidin-2-yl}propan-2-ol;
2-{5-[(8R,15S)-7-(Difluoromethoxy)-2-methyl-8,15-dihydro-3H-8,15-methanobenzimidazo[1,2-b]imidazo[4,5-e][2]benzazocin-11-yl]pyrimidin-2-yl}propan-2-ol;
2-{5-[(8R,15R)-7-(Difluoromethoxy)-1-(trifluoromethyl)-8H,15H-8,15-methanobenzimidazo[2,1-d][1,2,4]triazolo[3,4-a][2,5]benzodiazocin-11-yl]pyrimidin-2-yl}-propan-2-ol;
2-{5-[(8R,15R)-7-(Difluoromethoxy)-1-methyl-8H,15H-8,15-methanobenzimidazo[2,1-d][1,2,4]triazolo[3,4-a][2,5]benzodiazocin-11-yl]pyrimidin-2-yl}propan-2-amine;
1-{5-[(8R,15R)-7-(Difluoromethoxy)-1-methyl-8H,15H-8,15-methanobenzimidazo[2,1-d][1,2,4]triazolo[3,4-a][2,5]benzodiazocin-11-yl]pyrimidin-2-yl}cyclobutanamine;
1-{5-[(8R,15R)-7-(Difluoromethoxy)-12-fluoro-1-methyl-8H,15H-8,15-methanobenzimidazo[2,1-d][1,2,4]triazolo[3,4-a][2,5]benzodiazocin-11-yl]-3-fluoropyridin-2-yl}-cyclopentanamine hydrochloride;
1-{5-[(8R,15R)-7-(Difluoromethoxy)-8H,15H-8,15-methanobenzimidazo[2,1-d][1,2,3]-triazolo[5,1-a][2,5]benzodiazocin-11-yl]-3-fluoropyridin-2-yl}cyclobutanamine hydrochloride;
1-{5-[(8R,15R)-7-(Difluoromethoxy)-1-methyl-8H,15H-8,15-methanobenzimidazo[2,1-d][1,2,4]triazolo[3,4-a][2,5]benzodiazocin-11-yl]pyrimidin-2-yl}-3-(trifluoromethyl)-azetidin-3-ol;
1-{5-[(8R,15R)-7-(Difluoromethoxy)-1-methyl-8H,15H-8,15-methanobenzimidazo[2,1-d][1,2,4]triazolo[3,4-a][2,5]benzodiazocin-11-yl]-3-fluoropyridin-2-yl}cyclobutanamine;

1-{5-[(8R,15R)-7-(Difluoromethoxy)-8H,15H-8,15-methanobenzimidazo[2,1-d][1,2,4]-triazolo[3,4-a][2,5]benzodiazocin-11-yl]-3-fluoropyridin-2-yl}cyclobutanamine; and 4-{5-[(8R,15R)-7-(Difluoromethoxy)-1-methyl-8H,15H-8,15-methanobenzimidazo[2,1-d][1,2,4]triazolo[3,4-a][2,5]benzodiazocin-11-yl]pyrimidin-2-yl}piperazin-2-one.

5. A pharmaceutical composition comprising a compound of formula (I) as defined in claim 1 or an N-oxide thereof, or a pharmaceutically acceptable salt thereof, in association with a pharmaceutically acceptable carrier.

* * * * *